US012649953B2

(12) United States Patent
Pardee et al.

(10) Patent No.: US 12,649,953 B2
(45) Date of Patent: Jun. 9, 2026

(54) PAPER-BASED SYNTHETIC GENE NETWORKS

(71) Applicant: PRESIDENT AND FELLOWS OF HARVARD COLLEGE, Cambridge, MA (US)

(72) Inventors: Keith Pardee, Boston, MA (US); James J. Collins, Newton, MA (US)

(73) Assignees: PRESIDENT AND FELLOWS OF HARVARD COLLEGE, Cambridge (US);, TRUSTEES OF BOSTON UNIVERSITY

( * ) Notice: Subject to any disclaimer, the term of this patent is extended or adjusted under 35 U.S.C. 154(b) by 335 days.

(21) Appl. No.: 17/487,610

(22) Filed: Sep. 28, 2021

(65) Prior Publication Data

US 2022/0081729 A1     Mar. 17, 2022

Related U.S. Application Data

(62) Division of application No. 15/102,213, filed as application No. PCT/US2014/068861 on Dec. 5, 2014.

(60) Provisional application No. 62/066,966, filed on Oct. 22, 2014, provisional application No. 61/913,110, filed on Dec. 6, 2013.

(51) Int. Cl.
*C12Q 1/68* (2018.01)
*C12Q 1/6806* (2018.01)
*C12Q 1/6897* (2018.01)

(52) U.S. Cl.
CPC ......... *C12Q 1/6897* (2013.01); *C12Q 1/6806* (2013.01)

(58) Field of Classification Search
USPC ...... 435/6.1, 6.11, 91.1, 320.1; 436/94, 501; 536/23.1, 24.3, 24.33
See application file for complete search history.

(56) References Cited

U.S. PATENT DOCUMENTS

| 4,446,232 A | 5/1984 | Liotta |
| 5,496,562 A | 3/1996 | Burgoyne |
| 5,593,824 A | 1/1997 | Treml |
| 5,861,251 A | 1/1999 | Park et al. |

(Continued)

FOREIGN PATENT DOCUMENTS

| JP | 2005535311 A | 11/2005 |
| WO | 2003033675 A2 | 4/2003 |

OTHER PUBLICATIONS

Green et al., Toehold switches: de-novo-designed regulators of gene expression. Cell, 159, 925-939, 2014.*

(Continued)

*Primary Examiner* — Frank W Lu
(74) *Attorney, Agent, or Firm* — NIXON PEABODY LLP; David S. Resnick; Mark J. Fitzgerald

(57) ABSTRACT

Disclosed herein are shelf-stable compositions based on synthetic gene networks and/or cell-free systems that are lyophilized on a solid support. The compositions can be easily transported and stored for a period of time, and activation can be done by simply adding water. Methods of use are also disclosed herein, including, but are not limited to, sensing and a variety of logic functions. The invention permits straightforward, sterile and abiotic distribution of synthetic biology-based technology to clinical settings, food processing and industry, the military and consumer products.

13 Claims, 74 Drawing Sheets

(56) References Cited

U.S. PATENT DOCUMENTS

| | | |
|---|---|---|
| 6,512,580 B1 | 1/2003 | Behringer et al. |
| 6,737,269 B2 | 5/2004 | Gardner et al. |
| 7,048,915 B2 | 5/2006 | Kuroita et al. |
| 2002/0142318 A1 | 10/2002 | Cattell et al. |
| 2004/0101851 A1 | 5/2004 | White et al. |
| 2004/0130715 A1 | 7/2004 | Dosaka et al. |
| 2005/0069898 A1 | 3/2005 | Moon et al. |
| 2005/0153390 A1 | 7/2005 | Endo et al. |
| 2005/0201898 A1 | 9/2005 | Borich et al. |
| 2005/0202429 A1 | 9/2005 | Trau et al. |
| 2005/0243321 A1 | 11/2005 | Cohen et al. |
| 2006/0134074 A1 | 6/2006 | Naughton |
| 2007/0117094 A1 | 5/2007 | Hayashizaki et al. |
| 2007/0259348 A1 | 11/2007 | Phadke et al. |
| 2008/0182312 A1 | 7/2008 | Pack et al. |
| 2010/0056381 A1 | 3/2010 | Kurt et al. |
| 2010/0174141 A1 | 7/2010 | Gilad et al. |
| 2011/0076695 A1 | 3/2011 | Ohshiro |
| 2012/0003630 A1 | 1/2012 | Collins et al. |
| 2012/0207653 A1 | 8/2012 | Nakagawa et al. |
| 2013/0009799 A1 | 1/2013 | Collins et al. |
| 2013/0034907 A1 | 2/2013 | Collins et al. |
| 2014/0295533 A1 | 10/2014 | Faghri et al. |

OTHER PUBLICATIONS

Pardee et al., Paper-based synthetic gene networks. Cell, 159, 940-954, 2014.*
RTS 100 *E coli* HY Kit Manual, pp. 1-30, published on Sep. 2009 by 5 Primer.*
The Basics: in Vitro Translation from ThermoFisher Scientific, "Reporter Gene" from Wikipedia, and Fluorescent β Galactosidase Assay and β-Galactosidase Assay (CPRG) from G-Biosciences. Printed on Mar. 12, 2021.*
"Luciferase" from Wikipedia. Printed on Jan. 11, 2025.*
"Ribosome-binding site" from Wikipedia. Printed on Sep. 30, 2025.*

* cited by examiner

Ts/Tl reactions contained within a hydrophobic ring.

Paper

Quartz Microfiber

Constitutive

Inducible

Print hydrophobic        Spot reagents         Add trigger RNAs
barrier                  and freeze dry        and incubate

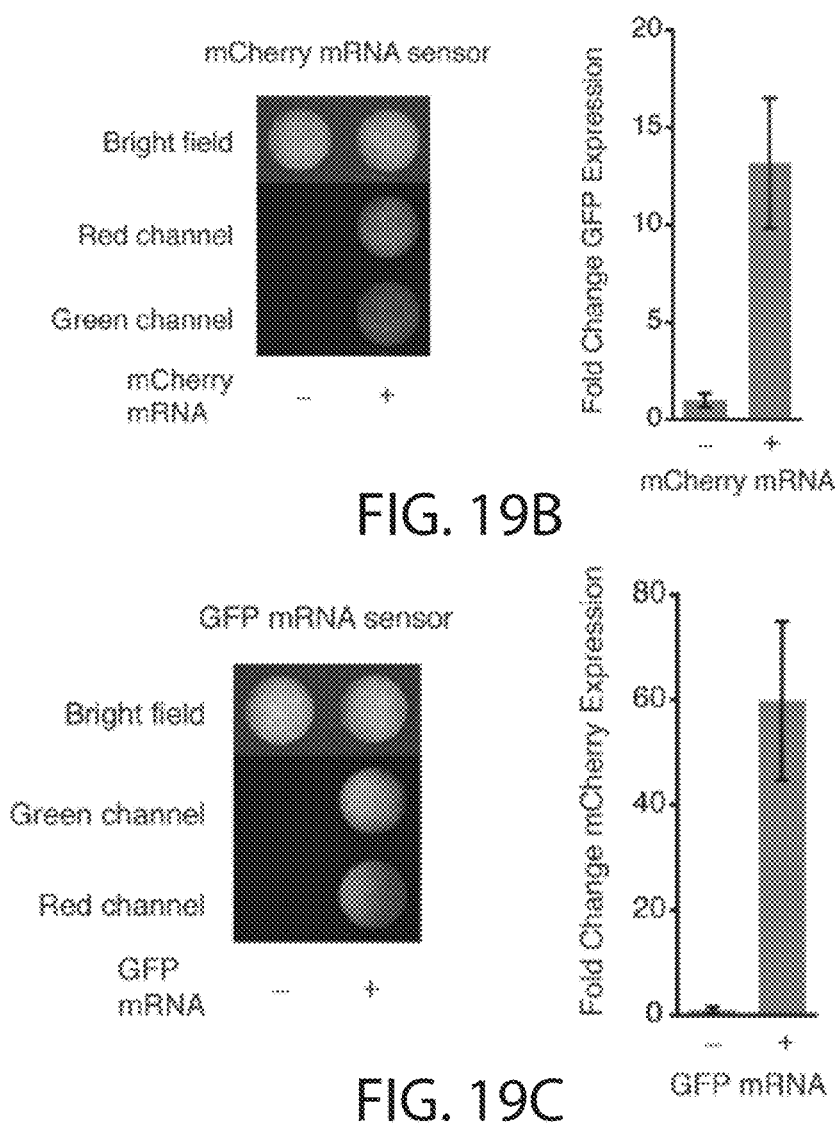
FIG. 19B
FIG. 19C
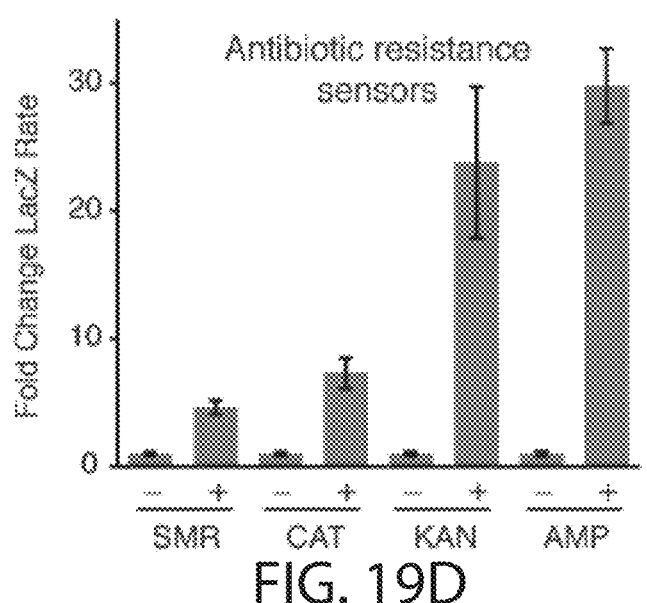
FIG. 19D

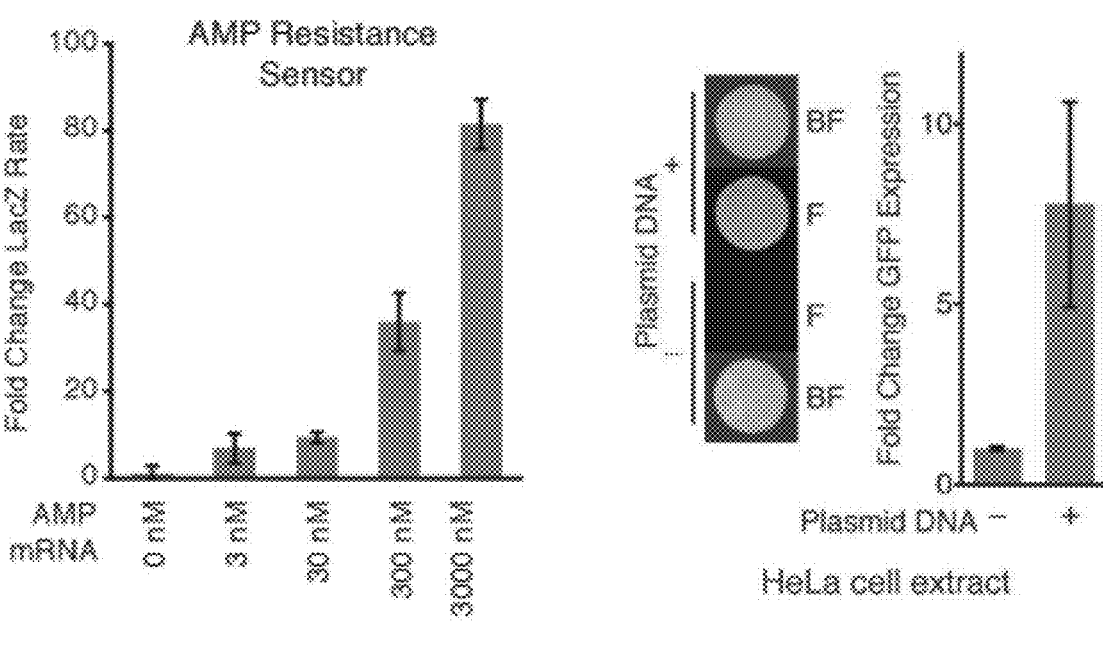
FIG. 19E
FIG. 19F
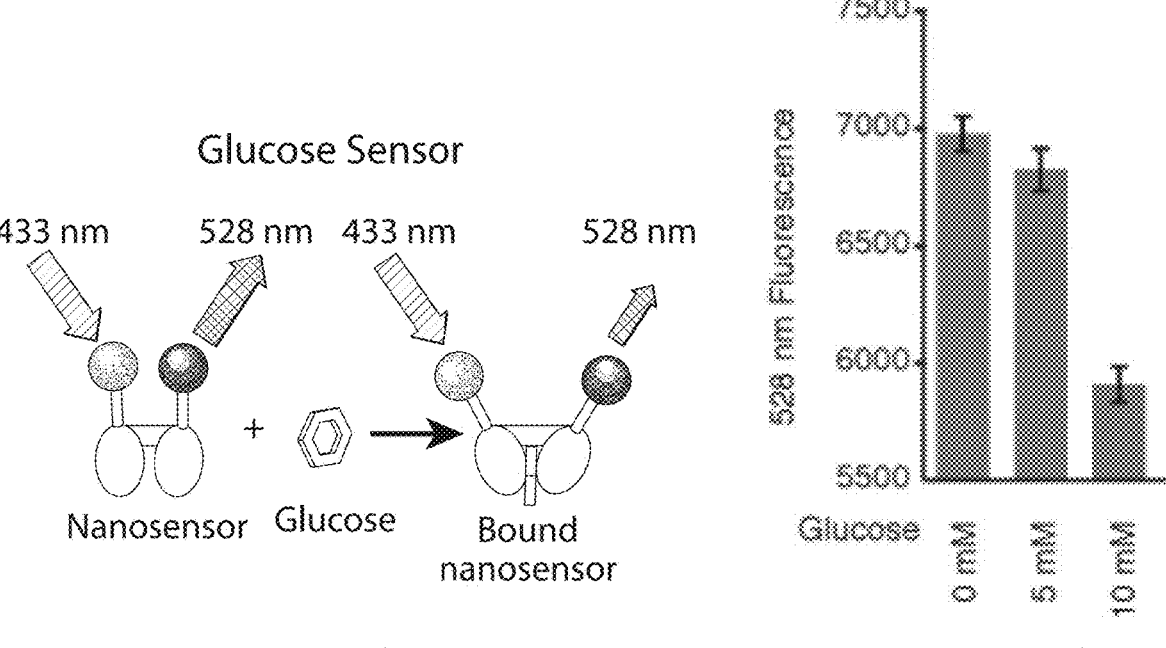
FIG. 19G
FIG. 19H

PAPER-BASED SYNTHETIC GENE NETWORKS

CROSS-REFERENCE TO RELATED APPLICATION

This application is a Divisional Application of U.S. application Ser. No. 15/102,213 filed Jun. 6, 2016, which is a 35 U.S.C. § 371 National Phase Entry Application of International Patent Application No. PCT/US2014/068861 filed Dec. 5, 2014, which claims benefit under 35 U.S.C. § 119(e) of U.S. Provisional Application No. 61/913,110 filed Dec. 6, 2013, and 62/066,966, filed Oct. 22, 2014, the contents of each of which are incorporated herein by reference in their entirety.

TECHNICAL FIELD

The present disclosure relates generally to shelf-stable compositions and methods for sensing and performing logic functions based on synthetic gene networks.

BACKGROUND

The field of synthetic biology aims to re-engineer the components of natural systems to solve global challenges like lowering the cost of drug production or green energy and chemistry. In doing so, synthetic biologists are creating whole-cell biosensors, synthetic probiotics, and new sources of drugs, green energy and novel chemistries. At the heart of these technologies are synthetic gene networks (Lu et al., Nat. Biotechnol. 2009, 27, 1139-1150) that control the cellular factories responsible for manufacturing. Hosting these engineered pathways in living cells has meant, primarily, that synthetic biology has been confined to the lab and large commercial operations.

Ongoing research has been attempting to move synthetic gene networks outside living cells. For example, liposomes have been explored to host synthetic gene networks (Shin and Noireaux, ACS Synth. Biol. 2012, 1, 29-41). However, both living cells and synthetic liposomes impose serious drawbacks in practical issues such as storage and transportation, thus limiting the distribution of devices based on synthetic gene networks and their applications. Particularly, it has not been possible to use these devices for on-demand applications.

Considering the potential of synthetic gene networks and the challenges faced by a skilled artisan in the field, what is needed are novel compositions and/or methods to facilitate easy distribution and storage of devices based on synthetic gene networks.

SUMMARY

Aspects of the invention relate to the discovery that a lyophilized synthetic gene network and/or a cell-free system comprising components sufficient for a template-directed synthetic reaction, can retain its bioactivity when stored under room temperature for a period of time. One aspect of the invention relates to a shelf-stable composition comprising a cell-free system that comprises components for a template-directed synthetic reaction, wherein the cell-free system is lyophilized on a solid support. The cell-free system can become active for the template-directed synthetic reaction upon re-hydration.

In one embodiment, the shelf-stable composition further comprises a synthetic gene network. In one embodiment, the synthetic gene network comprises one or more nucleic acids. The nucleic acid can comprise for example DNA, RNA, an artificial nucleic acid analog, or a combination thereof.

In one embodiment, the template-directed synthetic reaction is a transcription reaction, and the components sufficient for the transcription reaction comprise promoter-containing DNA, RNA polymerase, ribonucleotides, and a buffer system.

In one embodiment, the template-directed synthetic reaction is a translation reaction, and the components sufficient for the translation reaction comprise ribosomes, aminoacyl transfer RNAs, translation factors, and a buffer system. The components can also comprise amino acids or amino acids and aminoacyl tRNA synthetases.

In one embodiment, the template-directed synthetic reaction is a coupled transcription and translation reaction, and the components sufficient for the coupled transcription and translation reaction comprise promoter-containing DNA, RNA polymerase, ribonucleotides, ribosomes, aminoacyl transfer RNAs, translation factors, and a buffer system. The components can also comprise amino acids or amino acids and aminoacyl tRNA synthetases.

In one embodiment, the solid support is a porous substrate, and the shelf-stable composition is partially or completely embedded in the porous substrate.

In one embodiment, the porous substrate comprises paper.

In one embodiment, the porous substrate comprises quartz microfiber, mixed esters of cellulose, porous aluminum oxide, or a patterned surface.

In one embodiment, the solid support is pre-treated with bovine serum albumin, polyethylene glycol, Tween-20, Triton-X, milk powder, casein, fish gelatin, or a combination of one or more thereof.

In one embodiment, the cell-free system comprises a whole cell extract or a recombinant protein transcription/translation system.

In one embodiment, the whole cell extract is selected from the group consisting of rabbit reticulocyte lysate, wheat germ extract, *E. coli* extract, and human cell extract.

In one embodiment, the recombinant protein transcription/translation system permits protein synthesis using recombinant elements (PURE) or PURExpress® (New England Biolabs, Ipswich, MA) (see Shimizu and Ueda, "Pure Technology," Cell-Free Protein Production: Methods and Protocols, Methods in Molecular Biology, Endo et al. (Eds), Humana 2010; and Shimizu et al., "Cell-free translation reconstituted with purified components," Nature Biotechnology 2001, 19, 751-755).

In one embodiment, the synthetic gene network functions as a sensor.

In one embodiment, the sensor can detect an analyte in an aqueous sample.

In one embodiment, the detection of the analyte can produce an optical signal or an electronic signal.

In one embodiment, the synthetic gene network comprises a logic circuit.

In one embodiment, the logic circuit comprises an AND gate, a NOT gate, an OR gate, a NOR gate, a NAND gate, a XOR gate, a XAND gate, or a combination thereof.

In one embodiment, the logic circuit is activated upon contacting with water and optionally a composition comprising a trigger.

In one embodiment, the trigger is selected from the group consisting of a chemical element, a small molecule, a peptide, a protein, a nucleic acid, an extract, and a combination thereof.

In one embodiment, the shelf-stable composition is shelf stable for at least two weeks.

A related aspect of the invention regards a shelf-stable composition comprising a cell-free system comprising components sufficient for a template-directed synthetic reaction, a synthetic gene network, and a solid support, wherein said shelf-stable composition is substantially free of water, and wherein said cell-free system is active for said template-directed synthetic reaction upon rehydration.

Yet another aspect of the invention regards a shelf-stable composition produced by a process, the process comprising contacting a solid support with an aqueous solution comprising a cell-free system and a synthetic gene network, and lyophilizing said solid support.

Another aspect of the invention regards a method of detecting an analyte, comprising providing a shelf-stable composition described herein, wherein the composition comprises a nucleic acid-based sensor, contacting the composition with the analyte in the presence of water under conditions permitting transcription and/or translation, and detecting a signal, wherein detection of the signal indicates the presence of the analyte.

In one embodiment, the method further comprises a step of contacting the composition with a barrier to water evaporation or enclosing the composition in an enclosure after the contacting step.

In one embodiment, the method can provide a measure of the amount of the analyte.

In one embodiment, the nucleic acid-based sensor comprises a reporter gene.

In one embodiment, the reporter gene encodes a fluorescence protein, an enzyme, or an antigen.

In one embodiment, the nucleic acid-based sensor comprises a catalytic nucleic acid.

In one embodiment, the method further comprises providing a fluorophore, whereby said fluorophore can couple to a nucleic acid to produce a change in fluorescence.

In one embodiment, the analyte is selected from the group consisting of a nucleic acid, a pathogen, a pathogen extract, a metabolite, an antibiotic drug, an explosive chemical, a toxic chemical, and an industrial chemical.

In one embodiment, the toxic chemical is a heavy metal or insecticide residue.

In one embodiment, the signal is luminescence.

In one embodiment, the signal is fluorescence.

In one embodiment, the signal is a visible color.

In one embodiment, the signal is electronic.

In one embodiment, the analyte is in an aqueous solution.

Another aspect of the invention regards a method of activating a synthetic gene network lyophilized on a solid support, comprising providing a shelf-stable composition described herein, wherein the composition comprises the synthetic gene network, and contacting the composition with water.

A related aspect of the invention regards a method of activating a lyophilized synthetic gene network, comprising providing a lyophilized cell-free system comprising components sufficient for a template-directed synthetic reaction, and contacting the lyophilized synthetic gene network with the lyophilized cell-free system in the presence of water.

Yet another aspect of the invention relates to a kit comprising the shelf-stable composition described herein and packaging materials thereof.

In one embodiment, the kit further comprises an enclosure, wherein said enclosure encloses the composition during a template-directed synthetic reaction to slow or prevent water evaporation.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise. The abbreviation, "e.g." is derived from the Latin exempli gratia, and is used herein to indicate a non-limiting example. Thus, the abbreviation "e.g." is synonymous with the term "for example."

The term "shelf-stable" as used herein refers to the bioactivity (e.g., gene expression level, enzyme activity, or biosynthetic activity upon re-hydration) of the compositions described herein changing no more than 30% upon storage at room temperature (i.e., about 20° C. to 24° C.) and relative humidity of no more than 10% for two weeks. Stated another way, if the bioactivity of the shelf-stable composition re-hydrated on the day it's lyophilized (referred to as the first-day bioactivity herein) is set as 100%, then after two-week storage, the bioactivity of the composition is no less than 70%. A shelf-stable composition can also mean a composition that can regain at least 3% of the first-day bioactivity after storage for about 3 months, preferably at least 5%, at least 10%, at least 12%, at least 15%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of the first-day bioactivity.

At a maximum, the shelf-stable composition is stored in an environment with relative humidity of 60%. Preferably, the shelf-stable composition is stored in an environment with relative humidity of less than 50%, less than 40%, less than 30%, less than 20%, less than 10%, less than 5%, less than 1%, or less than 0.1%. In one embodiment, the shelf-stable composition is stored in a humidity-controlled environment (e.g., a desiccator or a containing comprising a desiccant). Preferably, the shelf-stable composition is stored in a an environment comprising nitrogen gas greater than 79% by volume, greater than 85% by volume, greater than 90% by volume, or greater than 95% by volume.

In one embodiment, the shelf-stable composition is stored in a container that blocks natural light. The percentage of light being blocked can be more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, or more than 90%.

As used herein, the term "substantially free of water" means that the water content in a composition is no more than 5% by weight. The term encompasses, for example, a water content of no more than 4%, no more than 3%, no more than 2%, no more than 1%, no more than 0.5%, or no more than 0.1% by weight.

As used herein, the term "cell-free system" refers to a set of reagents capable of providing for or supporting a biosynthetic reaction (e.g., transcription reaction, translation reaction, or both) in vitro in the absence of cells. For example, to provide for a transcription reaction, a cell-free system comprises promoter-containing DNA, RNA polymerase, ribonucleotides, and a buffer system. Cell-free systems can be prepared using enzymes, coenzymes, and other subcellular components either isolated or purified from eukaryotic or prokaryotic cells, including recombinant cells, or prepared as extracts or fractions of such cells. A cell-free system can be derived from a variety of sources, including, but not limited to, eukaryotic and prokaryotic cells, such as bacteria including, but not limited to, *E. coli*, thermophilic bacteria and the like, wheat germ, rabbit reticulocytes, mouse L cells, Ehrlich's ascitic cancer cells, HeLa cells, CHO cells and budding yeast and the like.

The term "biosynthetic reaction" is used herein to refer to any reaction that results in the synthesis of one or more biological compounds (e.g., DNA, RNA, proteins, monosaccharides, polysaccharides, etc.). For example, a transcription reaction is a biosynthetic reaction because RNA is produced. Other examples of biosynthetic reactions include, but are not limited to, translation reactions, coupled transcription and translation reactions, DNA synthesis, and polymerase chain reactions.

As used herein, the term "in vitro" refers to activities that take place outside an organism. In some embodiments, "in vitro" refers to activities that occur in the absence of cells. As used herein, a reaction occurring on a porous solid substrate in the absence of viable cells is an in vitro reaction.

As used herein, the term "porous substrate" refers to a substrate that contain pores or interstices via which a liquid composition may penetrate the substrate surface. Paper is one example of a porous substrate.

The term "synthetic biological circuit" is used herein to refer to any engineered biological circuit where the biological components are designed to perform logical functions. In general, an input is needed to activate a synthetic biological circuit, which subsequently produces an output as a function of the input. In some embodiments, a synthetic biological circuit comprises at least one nucleic acid material or construct. In some embodiments, a synthetic biological circuit is substantially free of nucleic acids. A synthetic gene network is one kind of synthetic biological circuit. Other examples of synthetic biological circuits include, but are not limited to, an engineered signaling pathway, such as a pathway that amplifies input via kinase activity.

"Synthetic gene network" or "synthetic gene circuit" are used interchangeably herein to refer to an engineered composition that comprises at least one nucleic acid material or construct and can perform a function including, but not limited to, sensing, a logic function, and a regulatory function. The nucleic acid material or construct can be naturally occurring or synthetic. The nucleic acid material or construct can comprise DNA, RNA, or an artificial nucleic acid analog thereof. In some embodiments of a synthetic gene network comprising at least two nucleic acid materials or constructs, the nucleic acid materials or constructs can interact with each other directly or indirectly. An indirect interaction means that other molecules are required for or intermediate in the interaction. Some examples of synthetic gene networks comprise a nucleic acid operably linked to a promoter.

As used herein, the term "operably linked" indicates that a promoter is in a correct functional location and/or orientation in relation to a nucleic acid sequence it regulates to control transcriptional initiation and/or expression of that sequence.

As used herein, the terms "nucleic acid," "polynucleotide," and "oligonucleotide" are used interchangeably to generally refer to any polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides. The term "nucleic acid" embraces chemically, enzymatically or metabolically modified forms of polynucleotides, as well as the naturally occurring chemical forms of DNA and RNA found in or characteristic of viruses and cells, including for example, simple (prokaryotic) and complex (eukaryotic) cells. A nucleic acid polynucleotide or oligonucleotide as described herein retains the ability to hybridize to its cognate complimentary strand. An oligonucleotide is not necessarily physically derived from any existing or natural sequence, but can be generated in any manner, including chemical synthesis, DNA replication, DNA amplification, in vitro transcription, reverse transcription or any combination thereof.

As used herein, a "promoter" refers to a control region of a nucleic acid sequence at which initiation and rate of transcription of the remainder of a nucleic acid sequence are controlled. A promoter can also contain sub-regions at which regulatory proteins and molecules can bind, such as RNA polymerase and other transcription factors. Promoters can be constitutive, inducible, activatable, repressible, tissue-specific or any combination thereof. A promoter drives expression or drives transcription of the nucleic acid sequence that it regulates.

As used herein, the term "signaling pathway" refers, unless context dictates otherwise, to the components of a signaling pathway. Thus, reference to a "signaling pathway" lyophilized on a solid support refers to components necessary for the signaling pathway of interest, lyophilized on the solid support. Similarly, reference to a "gene network" lyophilized on a solid support is a reference to the components of such a network lyophilized on the support.

The term "template-directed synthetic reaction" is used herein to refer to a synthetic reaction for which a nucleic acid template guides the pattern of nucleic acid or amino acid addition to a nucleic acid or polypeptide polymer. DNA replication and transcription are template-directed synthetic reactions that produce DNA or RNA products, respectively using a DNA template. Reverse transcription produces a DNA product using an RNA template. Translation is a template-directed synthetic reaction that produces a polypeptide or protein using an RNA template.

The terms "active" or "activated" are used interchangeably herein to refer to the readiness of a shelf-stable composition described herein or a portion thereof to perform an innate function or task. Reaction components lyophilized on a solid support are "activated" by addition of water or an aqueous sample, regaining transcription and/or translation activities. In some embodiments, the composition or a portion thereof performs the function or task when it's active or activated. In other embodiments, the composition or a portion thereof does not perform the function or task when it's active or activated, but is ready to do so when an external factor (an analyte or trigger as non-limiting examples) is provided. At a minimum, a lyophilized reaction/component mixture that regains at least 3% of its original activity upon re-hydration is considered "active." Preferably the mixture regains at least 10%, at least 12%, at least 15%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more of its original activity (i.e., activity just prior to lyophilization). The regained activity is comparable to the original activity when the difference between the two is no more than 20%.

As used herein, the term "sample," means any sample comprising or being tested for the presence of one or more analytes. Such samples include, without limitation, those derived from or containing cells, organisms (bacteria, viruses), lysed cells or organisms, cellular extracts, nuclear extracts, components of cells or organisms, extracellular fluid, media in which cells or organisms are cultured in vitro, blood, plasma, serum, gastrointestinal secretions, ascites, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, pleural fluid, nipple aspirates, breast milk, external secretions of the skin, respiratory, intestinal, and genitourinary tracts, and prostatic fluid. A sample can be a viral or bacterial sample, a sample obtained from an environmental source, such as a body of polluted water, an air sample, or a soil sample, as well as a food industry sample. A sample can be a biological sample which refers to the fact that it is derived or obtained from a living organism. The organism can be in vivo (e.g. a whole organism) or can be in vitro (e.g., cells or organs grown in culture). A sample can be a biological product. In one embodiment, a "biological sample" also refers to a cell or population of cells or a quantity of tissue or fluid from a subject. Often, a "biological sample" will contain cells from a subject, but the term can also refer to non-cellular biological material, such as non-cellular fractions of blood, saliva, or urine, that can be used to measure analyte or enzyme activity levels, for example, upon rehydration. Biological samples also include explants and primary and/or transformed cell cultures derived from patient tissues. A biological sample can be provided by removing a sample of cells from subject, but can also be accomplished by using previously isolated cells or cellular extracts (e.g., isolated by another person, at another time, and/or for another purpose). Archival tissues, such as those having treatment or outcome history can also be used. Biological samples include, but are not limited to, tissue biopsies, scrapes (e.g. buccal scrapes), urine, or cell culture. Biological samples also include tissue biopsies, cell culture. The term "sample" also includes untreated or pretreated (or pre-processed) samples. For example, a sample can be pretreated to increase analyte concentration.

As used herein, the term "trigger" refers to a composition, molecule, or compound that can activate a synthetic gene network.

The term "analyte" is used herein to refer to a substance or chemical constituent in a sample (e.g., a biological or industrial fluid) that can be analyzed (e.g., detected and quantified) and monitored using the sensors described herein. Examples of an analyte include, but are not limited to, a small inorganic or organic molecule, an ion, a nucleic acid (e.g., DNA, RNA), a polypeptide, a peptide, a monosaccharide, a polysaccharide, a metabolic product, a hormone, an antigen, an antibody, a biological cell, a virus, and a liposome.

As used herein, the term "small molecule" refers to a natural or synthetic molecule having a molecular mass of less than about 5 kD, organic or inorganic compounds having a molecular mass of less than about 5 kD, less than about 2 kD, or less than about 1 kD.

As used herein, the term "portable" refers to a device that can be held by a person of ordinary strength in one or two hands, without the need for any special carriers. A portable device can be configured to be used outside of a laboratory setting. In certain embodiments, a portable device is, e.g., battery powered.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

BRIEF DESCRIPTION OF THE DRAWINGS

FIG. 1A shows time course experiments of constitutive GFP expression from DNA template using fresh and freeze-dried transcription and translation reactions. Freeze-dried reactions had expression activity comparable to fresh reactions. FIG. 1B shows that extracts stored at room temperature with desiccant pack and a nitrogen-rich environment appear to maintain stable transcription and translation activity (at least 120 days). GFP expression from DNA template using a T7 RNA polymerase based system.

FIG. 5A shows inducible expression of GFP or mCherry from pTetO—based DNA template using 11 uM aTc. Reactions were embedded into quartz microfiber. FIG. 5B shows inducible expression of fluorescent reporter proteins from Toe-hold switches using freeze-dried T7-based expression system embedded into paper discs. In the presence of the correct RNA trigger, expression is induced. FIG. 5C shows that using a freeze dried cell-free expression system embedded into paper, GFP expression is repressed from Toe-hold repressor in the presence of the correct RNA trigger.

FIG. 10A is a schematic of the toe-hold switch mechanism. Activation of the toe-hold switch by the trigger RNA leads to expression of the reporter gene, which can be for example, a fluorescent reporter protein, an enzyme or other functional protein. In the case of colorimetric reactions, in one example, the enzyme LacZ is expressed and cleaves the yellow chlorophenol Red-β-D-galactopyranoside (CPRG) substrate to produce the purple chlorophenol red product. FIG. 10B shows development of color on paper discs using this LacZ-based colorimetric output can be seen developing beginning around 25 min. Top row of discs are controls rehydrated with ddH2O; the lower row of discs was rehydrated with ddH₂O and the trigger RNA. FIG. 10C are images of colorimetric data from Toe-hold switches 56, 69 and 96 with and without RNA trigger induction. From a freeze-dried preparation on 2 mm paper discs.

FIG. 11A shows that paper-based reactions perform better when paper has been pre-treated, washed and then dried before reactions are added (without wishing to be bound by theory, it is thought that pre-treatment reduces adsorption of reactions components to cellulose fibers). Paper was tested for best treatment agent with BSA (column 2), PEG (column 3), Triton X-100 (column 1), skim milk, and tween-20 (column 4). Column 5 is the control. In the end, the best performer was determined to be 5% BSA. FIG. 11B shows that quartz-based reactions perform better when quartz has been pre-treated, washed and then dried before reactions are added (without wishing to be bound by theory, it is thought that pre-treatment reduces adsorption of reactions components to quartz fibers). The quartz microfiber was tested for best treatment agent with BSA (column 1), PEG (column 2), Triton X-100 (column 3), skim milk, and tween-20 (column 4). Column 5 is the control.

(FIG. 12A) In the presence of super-folder GFP (sfGFP) mRNA, the GFP mRNA sensor is activated and expresses mCherry (GFP is also expressed from target GFP mRNA). (FIG. 12B) In the presence of mCherry mRNA, the mCherry mRNA sensor is activated and expresses GFP (mCherry is also expressed from target mCherry mRNA). This was used as a proof of concept for sensing active full-length mRNA.

(FIG. 13A) Freeze dried reactions supported the detection of mRNA resistance genes in solution, using a plate reader to measure GFP output. (FIG. 13B) Freeze dried reaction supported the detection of mRNA resistance genes on paper discs, using the LacZ enzyme-mediated colorimetric output.

FIG. 14A is a graphic representation showing two sensors connected by a microfluidic channel. FIG. 14B is a demonstration of how plastic films can be used to create microfluidics for the delivery of sample to more than one disc. FIG. 14C is a graphic representation showing a cross section of a design for FIG. 14A. FIG. 14D is a graphic representation showing four sensors connected by microfluidic channels.

FIG. 17A is a set of images of paper-based GFP expression from eight toehold switches (A-H) in the PT7 cell-free system, +/− complementary trigger RNAs.

FIG. 17B is a set of plots showing maximum fold change measurement of GFP expression from toehold switches A-H during the first 90 minutes of incubation.

FIG. 17C is a set of images showing RNA-actuated expression of GFP, venus, mCherry and cerulean fluorescent proteins from toehold switch H on paper and quartz microfiber discs.

FIG. 18A is a schematic of modified, LacZ expressing toehold switches used to generate colorimetric outputs.

FIG. 18B is a set of images of paper-based, colorimetric output from toehold switches A-H, +/− complementary RNA triggers.

FIG. 18C is a set of plots showing maximum fold change measurements from LacZ toehold switches A-H during the first 90 minutes of incubation. Fold induction based on the rate of color change from LacZ toehold switches.

FIG. 18D is a set of images showing the paper-based development of color from LacZ toehold switch D over 60 minutes.

FIG. 18E is a plot where color intensities from FIG. 18D converted to blue and yellow (red+ green) channels and graphed over time.

FIG. 18F is a schematic describing the process of arraying synthetic gene networks on paper using printed arrays.

FIG. 18G is an image of a 25-reaction printed array, with positive and control reactions distributed in a checkerboard pattern.

FIG. 18H is a schematic of a low cost, electronic optical reader developed to read colorimetric output from paper-based synthetic gene networks. Paper-based reactions are held in a chip between an LED light source (570 nm) and electronic sensor.

FIG. 18I is a plot of time course date from the electronic optical reader of toehold switch G in the presence of 0, 30, 300 and 3000 nM trigger RNA. All data were generated from freeze-dried, cell-free reagents embedded into paper with their respective gene circuits.

FIG. 19B presents images and fold-change measurements of a paper-based mCherry mRNA sensor in the presence and absence of full-length target mRNA. GFP is produced in response to detection of mCherry mRNA.

FIG. 19C presents Images and fold-change measurements of a paper-based GFP mRNA sensor in the presence and absence of full-length target mRNA. mCherry is produced in response to detection of GFP mRNA.

FIG. 19D is a plot showing fold change of the LacZ-mediated color output rate from sensors for mRNAs encoding resistance to spectinomycin, chloramphenicol, ampicillin and kanamycin antibiotics.

FIG. 19E is a plot showing fold change of the color output rate from the ampicillin resistance sensor using the purpose-built electronic optical reader over a titration of mRNA concentrations.

FIG. 19F presents images and fold-change measurement of constitutive paper-based GFP expression from a freeze-dried Hela cell extract.

FIG. 19G is a schematic of the FRET-based mechanism used in the glucose nanosensor.

FIG. 19H is a plot showing that 528 nm fluorescence is reduced in response to glucose binding to the FRET-based glucose nanosensor expressed on paper. All data were generated from freeze-dried, cell-free reactions embedded into paper with their respective gene circuits.

(FIG. 20A) GFP expression from S30 cell extracts. (FIG. 20B) GFP expression from S30 T7 cell extracts.

FIGS. 21A-21B are plots showing time course expression of TetO-regulated mCherry and GFP.

FIGS. 21C-21D are plots showing the rate of fluorescent expression plotted as a portion of maximum fluorescence, where maximum=1.

FIGS. 21E-21F are plots showing fold change of fluorescence output from aTC induce TetO mCherry and GFP, relative to uninduced controls. RFU, relative fluorescence units. Error bars represent standard deviation.

FIG. 22A is a plot showing aTc induction of TetO GFP in the absence and presence of tetR supplementation prior to freeze drying.

FIG. 22B is a plot aTc induction of TetO mCherry in the absence and presence of tetR supplementation prior to freeze drying. Error bars represent standard deviation.

FIG. 28A a set of plots showing showing paper-based regulation of GFP, venus, mCherry and cerulean fluorescent proteins by toehold switch H over a time course.

FIG. 28B is a set of images of quartz microfiber discs each embedded with three toehold switches (switch H_GFP, switch A_cerulean and switch C_mCherry). The four discs carrying these switches were rehydrated and incubated with either water or trigger RNAs for H, A or C. The individual activation of these switches was imaged using the green, blue and red fluorescence channels. Values presented are the average of either triplicate or quadruplicate data. Error bars represent standard deviation.

FIG. 29A is a set of plots showing Maximum fold change measurement of venus, mCherry and cerulean expression from toehold switches H during the first 90 minutes of incubation.

FIG. 29B is a set of plots showing the rate of fluorescence expression plotted as a portion of maximum fluorescence, where maximum=1. The red dots indicate the time point from which fold change calculations reported in FIG. 29A were taken.

FIG. 29C is a set of plots showing fold change of fluorescence output from RNA induced toehold switch H, relative to uninduced controls. Values presented are the average of either triplicate or quadruplicate data. Error bars represent standard deviation.

FIG. 33A is a plot showing maximum fold change of the colorimetric TetO_chitinase output at 420 mins.

FIG. 33B is a set of bright field and 410 nm absorbance images of the TetO_chitinase system embedded into paper, +/− aTc induction. Chitinase expression leads to the cleavage of a colorless precursor to generate a yellow product, which was quantified by monitoring absorbance at 410 nm.

FIG. 33C is a plot of time course evolution of the paper-based colorimetric reaction as measure by 410 nm absorbance.

FIG. 33D is a plot of rate of the colorimetric reaction plotted as a portion of maximum 410 nm absorbance, where maximum=1.

(FIG. 37A) Toehold switch H_GFP reactions on 2 mm paper discs that have been blocked with 5% BSA, 5% Triton X-100, 5% PEG 8k, 5% Tween-20 or washed with water. (FIG. 37B) Toehold switch B_GFP on paper discs treated as above, (FIG. 37C) Toehold switch H_GFP on 2 mm quartz microfiber discs treated as above and (FIG. 37D) Toehold switch B_GFP on quartz microfiber discs treated as above.

(FIG. 38A) 570 nm LED light source and luminosity sensors are coordinated to the Arduino Micro through two multiplexers. (FIG. 38B) Line drawings used to cut the reader housing from black acrylic using a laser printer.

FIG. 39A is a schematic of the generation of Ebola RNA sensors. Sensors with the same letter were targeted to identical windows in the Ebola nucleoprotein mRNAs of their respective strains.

FIG. 39B is a plot showing twenty-four toehold switch-based RNA sensors were constructed and tested in a 12 h period. Based on the RNA segment windows (A-L), maximum fold change during the first 90 minutes at 37° C. is reported for both the Sudan and Zaire strains of the virus. Fold change rate is determined from the slope of absorbance at 570 nm over time (-control, +3000 nM RNA trigger).

FIG. 39C is a composite image of the 240 paper-based reactions used to test the 24 sensors. Control and untriggered toehold sensors remain yellow and activated toehold sensors have turned purple.

FIG. 39D is a plot showing sequence specificity tested for four Sudan and four Zaire sensors from the original set of 24. Each of the four sensors targeting Sudan sequences were treated with 3000 nM of OFF-target RNA sequence from the complementing Zaire RNA sequence, and vice versa.

FIG. 39E is a set of plots showing fold change of the color output rate of sensors SD and ZH over a titration of RNA concentrations.

FIG. 40A is a schematic of the genetically encoded components that convert transcription from *E. coli* RNAP into transcription from T3 RNAP and/or T7 RNAP. Expression of these new RNAPs drive the transcription of previously dormant GFP constructs with T3 or T7 promoters, as well as a toehold switch and trigger pair under the regulation of T7 and T3, respectively.

FIG. 40B present images and fold-change measurements of paper-based T3 GFP expression with and without T3 cascade module.

FIG. 40C present images and fold-change measurements of paper-based T7 GFP expression with and without T7 cascade module.

FIG. 40D present images and fold-change measurements of paper-based T3/T7-dependent GFP expression with and without T3 and T7 cascade modules. All data were generated from freeze-dried, cell-free reactions embedded into paper with their respective GFP expression constructs; cascade modules were added as DNA components at rehydration. Data were collected after an overnight incubation.

DETAILED DESCRIPTION

Figure 1A:
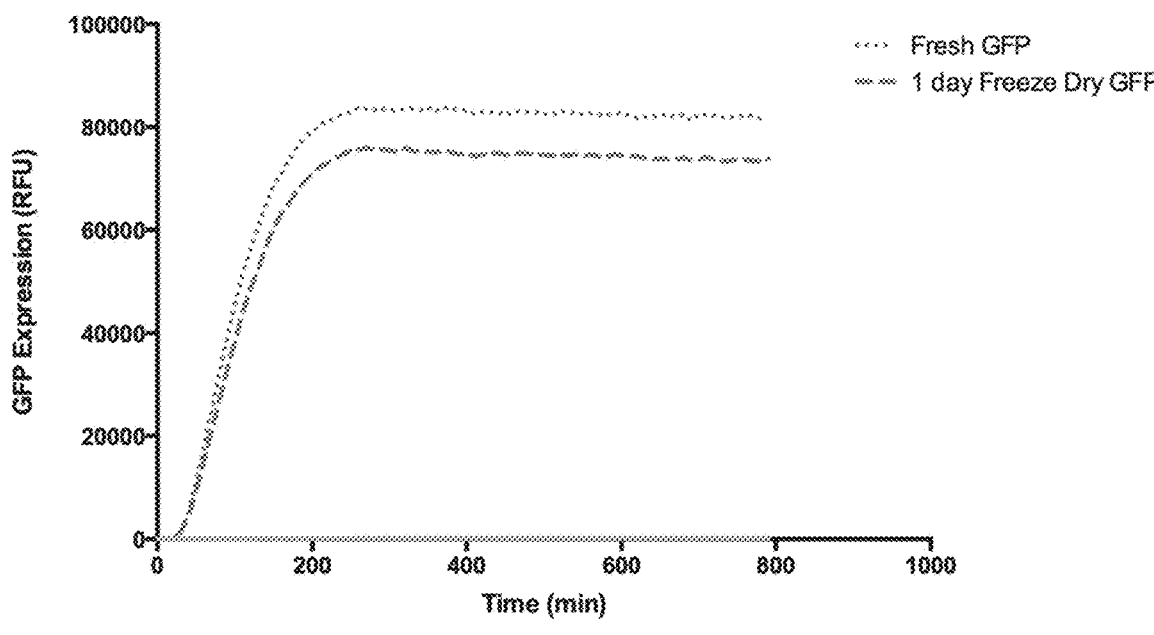
FIGS. 1A-1B show that freeze-dried cell-free systems can retain bioactivity and can be stored over a period of time.

Aspects of the technology described relate to the discovery that a lyophilized synthetic gene network and/or a cell-free system comprising components sufficient for a template-directed synthetic reaction, can retain its bioactivity when stored under room temperature for a period of time. Upon adding water, the synthetic gene network and/or the cell free system can become activated, and can perform in the same or similar manner compared to a counterpart that is hosted in a living cellular system. For example, as shown in FIG. 1A, green fluorescent protein (GFP) can be produced after a freeze-dried cell-free system is activated; and the GFP can emit green fluorescence, indicating that the protein is properly folded and active. This surprising discovery offers as yet unavailable methods for sterile and abiotic transportation, storage, and/or safe deployment of novel devices based on synthetic gene networks. The discovery has opened a new and significant avenue for synthetic biology applications. In the in vitro diagnostics space, this translates to the development of sensors and logic processing based on synthetic gene networks. In the research and education space, this translates to the safe distribution of synthetic gene networks for research or education purposes.

The described devices and methods were developed to exploit this discovery, and can be broadly applicable in areas including, but are not limited to, point-of-care diagnostics, clinical and industrial settings, and consumer goods.

Accordingly, one aspect of the technology described regards a method of stabilizing a synthetic gene network and/or a cell-free system comprising components sufficient for a template-directed synthetic reaction, the method comprising lyophilizing the synthetic gene network and/or the cell-free system. In one embodiment, the lyophilization step is done onto a solid support. The synthetic gene network or cell-free system regains bioactivity upon rehydration. In one embodiment, bioactivity is biosynthetic activity.

A related aspect of the technology disclosed herein regards a shelf-stable composition comprising a cell-free system that comprises components for a template-directed synthetic reaction, wherein the cell-free system is lyophilized on a solid support. The cell-free system can become active for the template-directed synthetic reaction upon re-hydration.

In one embodiment, a template-directed synthetic reaction is a transcription reaction, and the components sufficient for the transcription reaction comprise promoter-containing DNA, RNA polymerase, ribonucleotides, and a buffer system. Examples of RNA polymerases include, but are not limited to, T3 RNA polymerase, T7 RNA polymerase, and SP6 RNA polymerase.

In one embodiment, a template-directed synthetic reaction is a translation reaction, and the components sufficient for the translation reaction comprise ribosomes, aminoacyl transfer RNAs, translation factors, and a buffer system. Components of translation factors are disclosed in Shimizu and Ueda, "Pure Technology," Cell-Free Protein Production: Methods and Protocols, Methods in Molecular Biology, Endo et al. (Eds), Humana 2010; and Shimizu et al., "Cell-free translation reconstituted with purified components," Nature Biotechnology 2001, 19, 751-755. For example, in *E. coli*, the translation factors responsible for protein biosynthesis are three initiation factors (IF1, IF2, and IF3), three elongation factors (EF-G, EF-Tu, and EF-Ts), and three release factors (RF1, RF2, and RF3), as well as RRF for termination. Exemplary cell-free systems for synthesis of proteins are disclosed in U.S. Pat. Nos. 6,780,607, 8,445, 232, US20090317862, US20130053267, WO2013067523, WO2014122231, the contents of each of which are incorporated by reference in their entirety.

In one embodiment, a template-directed synthetic reaction is a coupled transcription and translation reaction, and the components sufficient for the coupled transcription and translation reaction comprise promoter-containing DNA, RNA polymerase, ribonucleotides, ribosomes, aminoacyl transfer RNAs, translation factors, and a buffer system. In a coupled transcription and translation reaction, DNA is transcribed into mRNA and the mRNA is subsequently translated into proteins, as described in Current Protocols in Molecular Biology (F. M. Ausubel et al. editors, Wiley Interscience, 2002), which is incorporated by reference herein.

In one embodiment, a template-directed synthetic reaction is DNA synthesis, and the components sufficient for the DNA synthesis comprise DNA polymerase, deoxyribonucleotides, and a buffer system. The DNA polymerase can be, but need not necessarily be, a thermostable DNA polymerase.

In one embodiment, a template-directed synthetic reaction is a polymerase chain reaction (PCR), and the components sufficient for PCR comprise a DNA template, primers, thermostable polymerase, deoxynucleoside triphosphates, and a buffer system.

In one embodiment, the cell-free system comprises a whole cell extract. The whole cell extract can be an extract from any cell type from any organism. For example, the whole cell extract can be rabbit reticulocyte lysate, rabbit oocyte lysate, wheat germ extract, *E. coli* extract, a mammalian cell extract (e.g., human cell extract). Eukaryotic extracts or lysates may be preferred when the resulting protein is glycosylated, phosphorylated or otherwise modified because many such modifications are only possible in eukaryotic systems. Commercial whole cell extracts are widely available through vendors such as Thermo Scientific, Life Technologies, New England Biolabs Inc., Sigma Aldrich, and Promega. Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3 (a or 0), elongation factor T (EF-Tu), or termination factors.

In one embodiment, the cell-free system comprises a recombinant protein transcription/translation system. In one embodiment, the recombinant protein transcription/translation system permits protein synthesis using recombinant elements (PURE) or PURExpress® (New England Biolabs, Ipswich, MA) cell-free transcription/translation system. PURExpress® is a cell-free transcription/translation system reconstituted from the purified components necessary for *E. coli* translation.

In one embodiment, the cell-free system can initiate a template-directed synthetic reaction simply upon rehydration (e.g., FIG. 1A).

In another embodiment, the cell-free system becomes activated for a template-directed synthetic reaction upon rehydration, but an input is needed to initiate the reaction.

In one embodiment, the cell-free system is embedded partially or completely in the solid support. In one embodiment, the cell-free system is on a surface of the solid support.

The solid support can be in any form including, but is not limited to, a well, a tube, a planar substrate (e.g., a chip or a plate), a sphere, a porous substrate (e.g., a mesh or a foam), a 3D scaffold, a patterned surface (e.g., nano-patterns, or micro-patterns, or both), a porous or solid bead, a hydrogel, a channel (e.g., a microfluidic channel), a smooth surface, and a rough surface. In a preferred embodiment, the solid support is hydrophilic and preferably porous.

A patterned surface can be physically or chemically patterned, or both. A physically patterned surface is textured, and can comprise nano-patterns, micro-patterns, or both. A chemically patterned surface typically comprises hydrophilic molecules and/or hydrophobic molecules attached to the surface in a desired pattern. For example, a hydrophobic surface can be patterned with hydrophilic molecules to render certain regions hydrophilic. Methods of producing physically or chemically patterned surfaces are known in the art.

In a preferred embodiment, the solid support comprises a matrix capable of high capillary action. High capillary action enables even distribution of a small volume of liquid over a large surface area without the use of a pump. Preferably, the matrix capable of high capillary action is porous and hydrophilic.

In preferred embodiments, the solid support comprises paper. Papers applicable in the technology described herein can include, but not limited to, printing paper, wrapping paper, writing paper, drawing paper, specialty paper (for example, chromatography paper, filter paper, e.g., Whatman™ filter paper), handmade paper, or blotting paper. The use of paper confers several advantages: low cost, light weight, and thin cross section. Additionally, white paper can act as a surface for displaying optical signals (e.g., fluorescence, luminescence, or visible color).

In one embodiment, the paper is hydrophilic and preferably porous.

In one embodiment, the paper is hydrophobic. For example, hydrophobic paper can become hydrophilic after treatment by a laser (Chitnis et al., Lab Chip 2011, 11, 1161), therefore one can create hydrophilic regions on hydrophobic paper by selective laser scanning.

In one embodiment, the solid support comprises quartz microfiber, mixed esters of cellulose, cellulose acetate, silk, porous aluminum oxide (e.g., anopore membrane), or regenerated membrane.

In one embodiment, the shelf-stable composition is lyophilized in a tube/micro-chamber and then transferred to a high capillary material upon re-hydration.

In one embodiment, the solid support comprises a sticky component, thereby allowing the shelf-stable composition to stay on surfaces.

Figure 4:
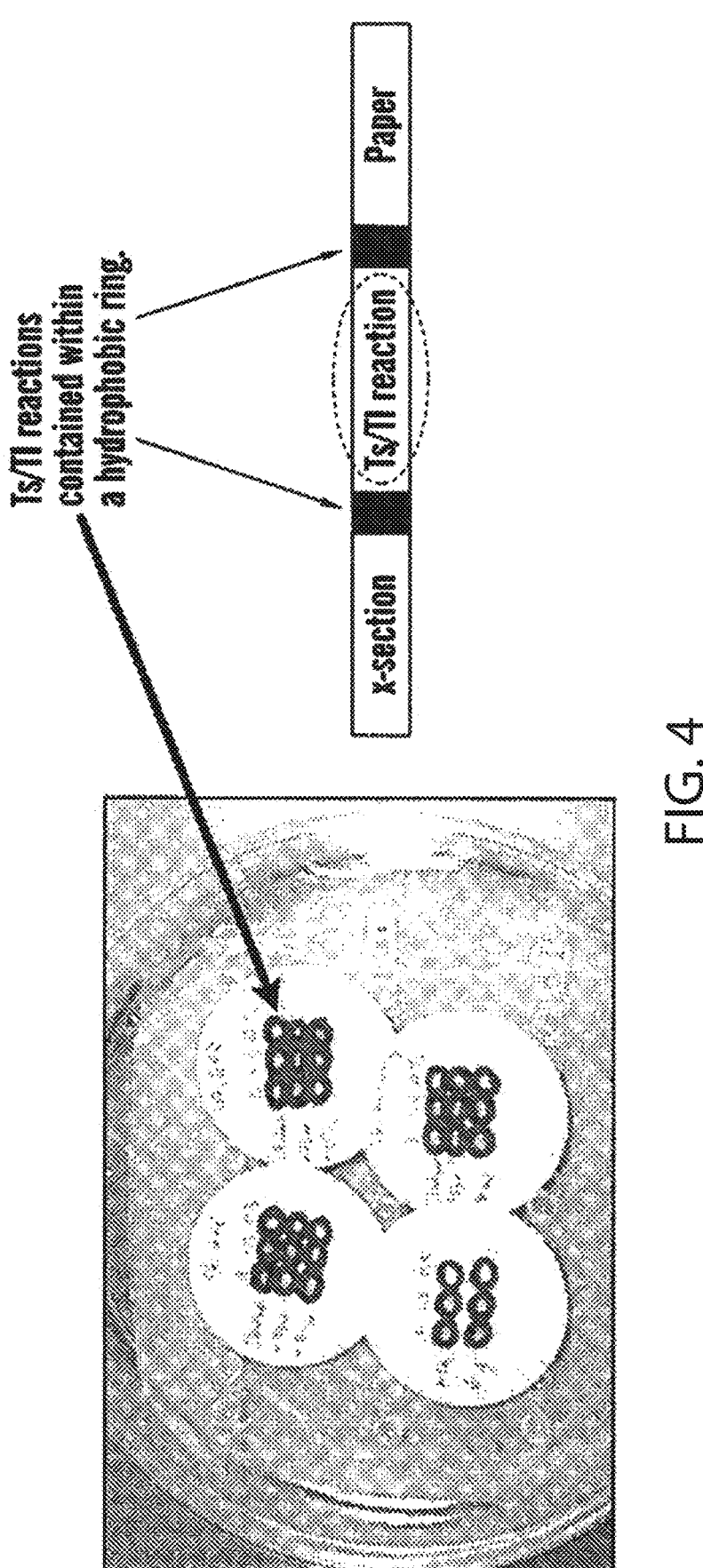
FIG. 4 shows that hydrophobic rings can be used to create reaction regions on a paper substrate. Hydrophobic ink was applied to paper, briefly heated to remove water and ensure ink fully spanned the thickness of the paper. Using a humid chamber, various expression constructs were tested at load volumes of 0.5, 1.5 and 3 uL.
Figure 18A:
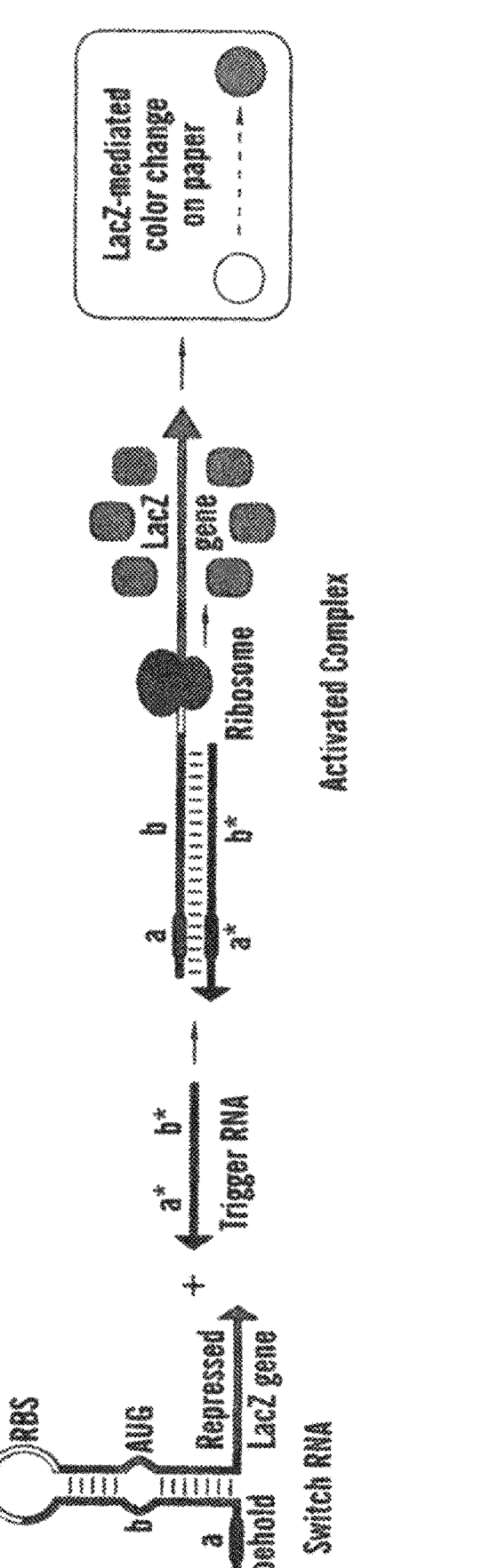
FIGS. 18A-18I demonstrate colorimetric output from paper-based synthetic gene networks.
Figure 18C:
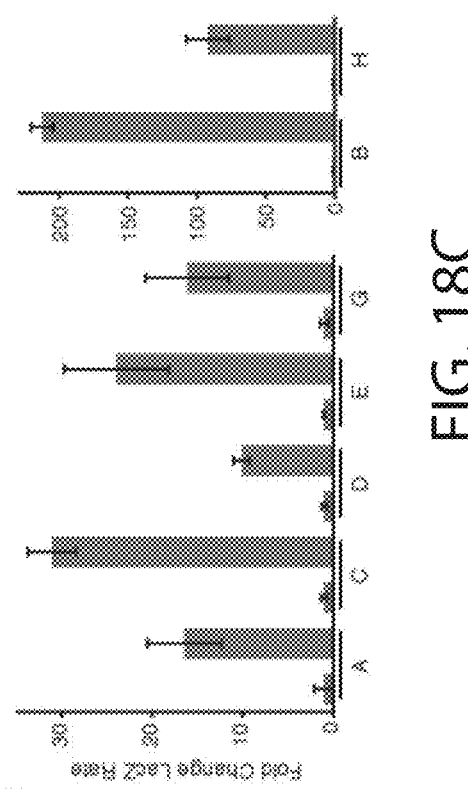
Figure 18B:
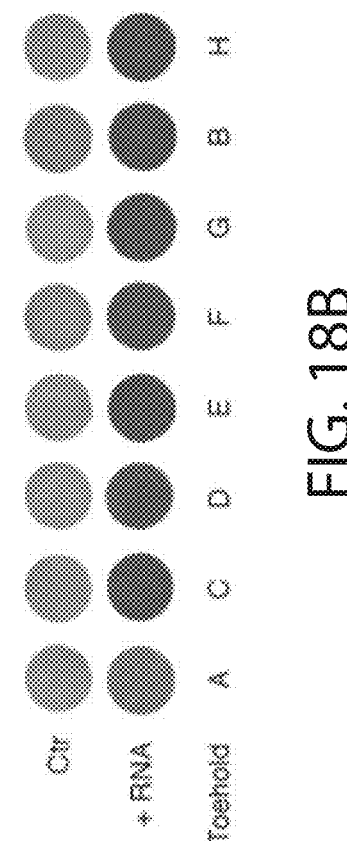

In one embodiment, the solid support comprises 1, 2, 3, 4, 5, 6, 7, 8, 9, 10, 20, or more spatially distinct reaction regions where the cell-free system is confined. The area that contains the cell-free system is herein referred to as "a reaction region." By way of example only, reaction regions can be created by a chemical process such as using hydrophobic barriers on a piece of paper (FIG. 4 or 18F). The hydrophobic barriers are minimally permeable by water. When an aqueous solution comprising the cell-free system is added to a reaction region, due to the presence of the hydrophobic barrier, the solution is confined within the reaction regions. The hydrophobic barrier can comprise hydrophobic materials such as hydrophobic polymer or wax. The hydrophobic barrier can be patterned by any existing patterning method (e.g., micro-contact printing, or dip pen lithography, photolithography, e-beam lithography, laser printing, inject printing, or a micro-arrayer). Methods of creating hydrophobic patterns on paper are known in the art; see for example, WO2009121041 and WO2008/049083, the contents of each of which are incorporated by reference for the hydrophobic patterning methods.

The reaction regions can be arranged in a random or pre-determined pattern (e.g., linear, periodic, or pseudo-periodic). The reaction regions can be patterned on the solid support using a patterning device (e.g., a laser printer, an inject printer or a micro-arrayer). The reaction regions can also be created by a physical process such as producing wells on the solid support.

In one embodiment, the solid support can be pre-treated with a protein source (e.g., bovine serum albumin, milk powder, casein, or fish gelatin), polyethylene glycol, a surfactant (e.g., polysorbate 20 or Triton-X), or a combination thereof. Without wishing to be bound by theory, this pre-treatment step can increase the signal-over-noise ratio for a fluorescent signal by limiting non-specific binding and/or irreversible binding of the reaction components. For example, see FIG. 37.

In one embodiment, the solid support comprises one or more fluidic channels (e.g., microfluidic channels) that connect reaction regions with an area for adding an aqueous sample. In this embodiment, when an aqueous sample is added to the area, the fluid is wicked away to the reaction regions, thereby a plurality of reaction regions can be activated by the same sample (for example, see FIGS. 14A-14D).

In one embodiment, the solid support can further comprise electrodes, thus allowing the solid support to interface with electronic devices. For example, electrodes can be patterned using methods including, but not limited to, photolithography, e-beam lithography, and masked evaporation. For example, methods of patterning electrodes on paper can be found in WO2009121041.

In one embodiment, the solid support is a reaction chip. The reaction chip can comprise a sample hosting layer, a light blocking layer, a hydration layer, a transparent layer, a humidity maintaining layer, and a water vapor permeable layer. The hydration layer can comprise a hydrated material or chamber that provides humidity during incubation and/or measurement. The humidity maintaining layer can be water impermeable. The water vapor permeable layer can regulate humidity for the sample.

In one embodiment, the shelf-stable composition further comprises a synthetic gene network. Synthetic gene networks have been largely confined to research laboratories due to its reliance on living cellular systems and a lack of means for long-term storage. The inventors' discovery overcame these challenges and provided a straightforward yet highly effective solution for storing and transporting devices based on synthetic gene networks. In addition, the shelf-stable composition described herein can be used in on-demand applications, which had not been achievable in the past.

Since the inception of synthetic biology, a wide variety of synthetic gene networks have been demonstrated, and any synthetic gene network can be applicable in the technology disclosed herein, including, but not limited to a sensor, a switch, a counter, a timer, a converter, a toggle, a logic gate (e.g., AND, NOT, OR, NOR, NAND, XOR, XAND, XNOR, A IMPLY B, A NIMPLY B, B IMPLY A, B NIMPLY A, or a combination thereof), or a memory device (e.g., volatile or non-volatile). Examples of synthetic gene networks can be found in U.S. Pat. No. 6,737,269, US20100175141, US20120003630, US20130009799, US20130034907, and WO2014093852, the contents of each of which are incorporated by reference in their entirety. For example, WO2014093852 describes 16 logic gates based on synthetic gene networks: AND, OR, NOT A, NOT B, NOR, NAND, XOR, XNOR, A IMPLY B, B IMPLY A, A NIMPLY B, B NIMPLY A, A, B, FALSE and TRUE. Methods of constructing synthetic gene networks are also disclosed, for example, in Synthetic Gene Networks, Weber and Fussenegger (Eds.) 2012, Humana Press, the contents of which are incorporated by reference in their entirety. The synthetic gene network is also lyophilized on the solid support, and resides in the same reaction region as the cell-free system. Similar to the cell-free system, the synthetic gene network becomes active upon rehydration.

Without wishing to be bound by theory, the relationship between the different components in the shelf-stable composition can be understood from an information flow point of view. In a straightforward scenario, an input (e.g., an analyte, a trigger, or a combination) from the environment provides upstream information to the synthetic gene network, which processes the information and relays it to the cell-free system. The cell-free system performs a template-directed synthetic reaction based on the information, and then generates downstream information in the form of an output (e.g., an optical signal, an electronic signal, or a combination) to the environment.

In one embodiment, the synthetic gene network comprises 1, 2, 3, 4, 5, 6, 7, 8, 9, 10, or more nucleic acids. The nucleic acid comprises DNA, RNA, an artificial nucleic acid analog, or a combination thereof.

In one aspect, the synthetic gene network functions as a sensor. In one embodiment, the sensor can detect an analyte. When the analyte contacts the shelf-stable composition in the presence of water, the analyte activates the sensor, which produces a signal, indicating the detection of the analyte. In some embodiments, the signal is optical. Without limitation, an optical signal can be fluorescence, luminescence, absorption or reflection of a given wavelength, ultraviolet, visible color, or infrared. In some embodiments, the signal is electronic (e.g., conductivity change or capacitance change).

In one embodiment, the sensor comprises a reporter component. The function of the reporter component is to produce a detectable signal when an analyte is detected. In one embodiment, a reporter component can be used to quantify the concentration, strength, or activity of the input received by the compositions of the invention. In one embodiment, the reporter component comprises a reporter gene. A reporter gene encoding any fluorescent protein can be applicable in the invention. The fluorescent protein includes, but is not limited to, for example, GFP, mCherry, Venus, and Cerulean. Examples of genes encoding fluorescent proteins that can be used in accordance with the compositions and methods described herein include, without limitation, those proteins provided in U.S. Patent Application No. 2012/0003630 (see Table 59), incorporated herein by reference.

Similarly, a reporter gene encoding any enzyme can be applicable as well. Enzymes that produce colored substrates ("colorimetric enzymes") can also be used for visualization and/or quantification. Enzymatic products can be quantified using spectrophotometers or other instruments that can take absorbance measurements including plate readers (for example, see FIG. 26). Examples of genes encoding colorimetric enzymes that can be used in accordance with the compositions and methods described herein include, without limitation, lacZ alpha fragment, lacZ (encoding beta-galactosidase, full-length), and xylE. An enzyme (e.g., glucose oxidase) can also change the conductivity of a reaction volume, permitting an electrical or electronic readout (Malitesta et al., Anal Chem 1990, 62, 2735-2740). In another example, a nuclease enzyme can cleave a nucleic acid sequence such that an electronic and optical signal is generated. In yet another example, an enzyme can separate a fluorescence resonance energy transfer (FRET) or quenching pair to induce a change in fluorescence.

A reporter gene encoding any antigen for which a specific antibody is available or can be made can also be applicable. By way of example only, as antigens are expressed by the reporter gene, the antigens bind to an electrode coated with complementary antibodies, which produces an electronic signal. Conversely, a reporter gene can encode an antibody, which when expressed, binds to an electrode coated with the complementary antigen. For non-limiting examples of reporter genes, see Reporter Genes: A Practical Guide, D. Anson (Ed.), 2007, Humana Press, the contents of which are incorporated by reference for examples on reporter genes.

A reporter gene encoding luciferases can also be used in the technology described herein. Luciferases produce luminescence, which can be readily quantified using a plate reader or luminescence counter. Examples of genes encoding luciferases for that can be used in accordance with the compositions and methods described herein include, without limitation, dmMyD88-linker-Rluc, dmMyD88-linker-Rluc-linker-PEST191, and firefly luciferase (from Photinus pyralis).

In one embodiment, the reporter component comprises a catalytic nucleic acid including, but not limited to, a ribozyme, an RNA-cleaving deoxyribozyme, a group I ribozyme, RNase P, a Hepatitis delta ribozyme, and DNA-zymes. The use of catalytic nucleic acid as reporters is described in WO1996027026.

In one embodiment, the reporter component comprises a fluorophore, a metabolite, or protein, wherein the fluorophore, metabolite, or protein can couple to a nucleic acid to produce a change in fluorescence. For example, RNA-fluorophore complexes have been reported and can be used in the compositions and methods described herein (see, e.g., Paige et al., Science 2011, 333, 642-646). RNA binding to metabolites or proteins can also lead to a change in fluorescence (see, e.g., Strack et al., Nature Protocols 2014, in press). In one embodiment, the nucleic acid can be the analyte. In another embodiment, the nucleic acid can be transcribed due to the detection of an analyte.

In one embodiment, the sensor or network comprises a gene that encodes a therapeutic peptide or protein, antibiotics or other therapeutic agent that is produced in response to a specific set of conditions, e.g., pathogen presence. For example, the sensor(s) or network (s) can be embedded into wound dressing/bandaids for infection monitoring and alert with colorimetric output and/or produce therapeutic agents.

In one embodiment, the sensor is an RNA sensor. The RNA sensor can detect a full-length RNA or a fragment thereof. In one embodiment, the RNA sensor can detect messenger RNA (mRNA).

Figure 10A:
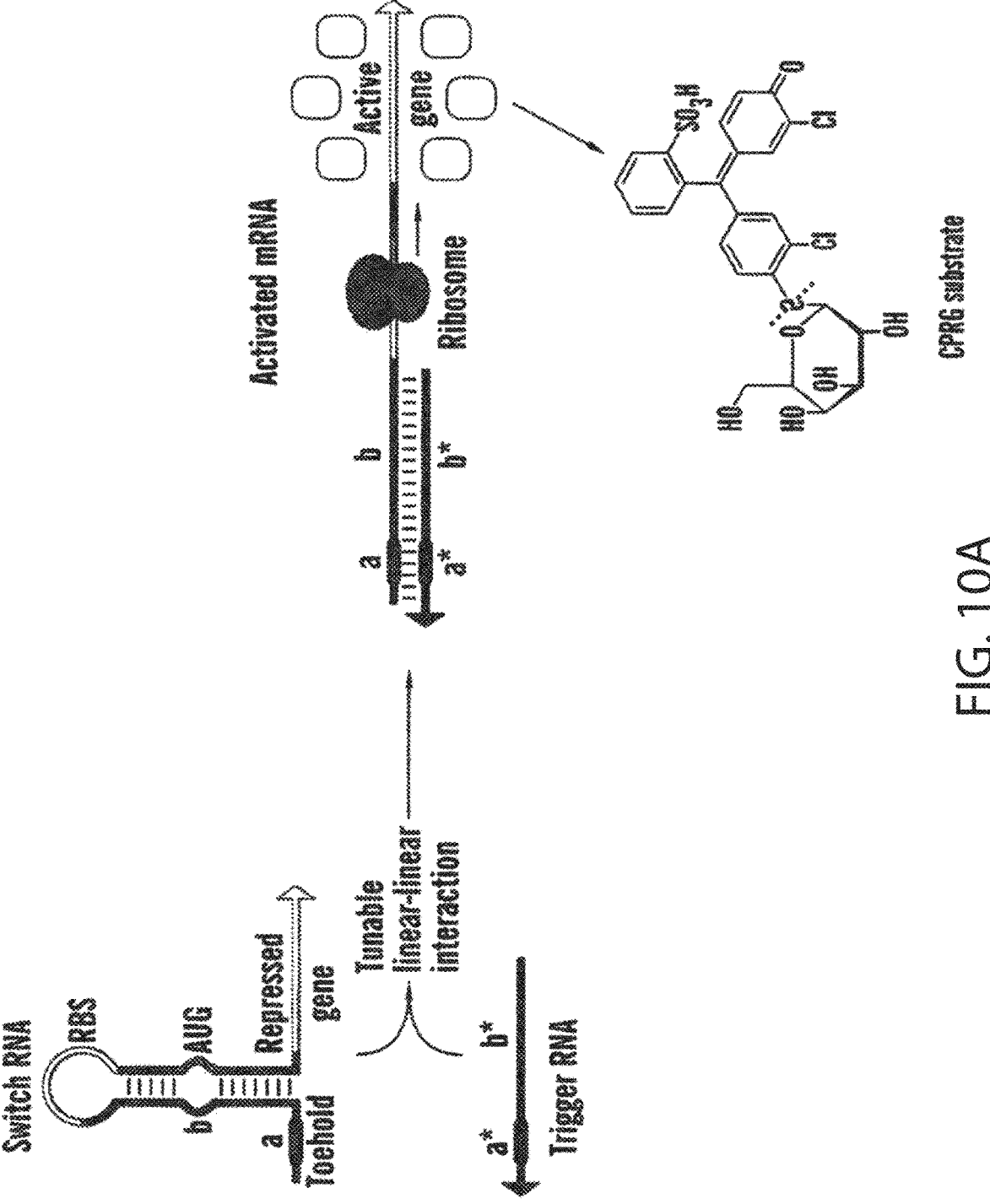
FIGS. 10A-10C show toe-hold switch mechanism and sensors based on toe-hold switches.

In one embodiment, an RNA sensor was created based on the principles of toe-hold switches (FIG. 10A). The rational programmability of toehold switches comes from their design. Riboregulators are composed of two cognate RNAs: a transducer RNA that encodes the output signal of the system (e.g. a GFP mRNA) and a trigger RNA that modu-lates the output signal. Conventional riboregulators have historically repressed translation by sequestering the ribo-somal binding site (RBS) of the transducer RNA within a hairpin. This hairpin is unwound upon binding of a cognate trigger RNA, exposing the RBS and enabling translation of the downstream protein. However, this design restricts the potential trigger RNAs to those that contain RBS sequences. Toehold switches have removed this constraint by moving the RBS to a loop region of the hairpin, leaving the trigger RNA binding site free to adopt virtually any sequence. The transducer or "switch" RNA of toehold switches also con-tains a single-stranded domain known as a toehold its 5' end. This toehold domain, first developed in in vitro molecular programming studies (Yurke, B., et al., Nature 2000, 406, 605-608), provides the initial reaction site for binding between the trigger and switch RNAs and greatly improves the ON/OFF ratio of the switches. Examples of RNA sensors based on toehold switches can be found, for example, in WO2014074648, the contents of which are incorporated by reference in their entirety.

Figure 9:
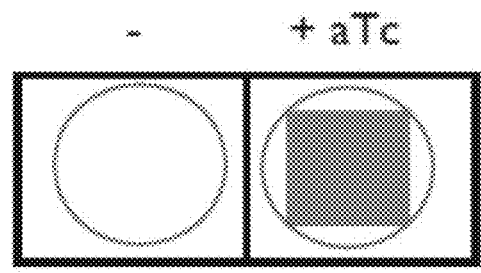
FIG. 9 is a colorimetric reporter system based on the expression of the enzyme chitinase. In this case, the fluorescent reporter protein gene from tetO_GFP has been removed and replaced with chitinase. Upon the addition of aTC inducer, expression of chitinase is activated. The enzyme cleaves the colorless 4-Nitrophenyl N,N'-diacetyl-beta-D-chitobioside substrate to yield a yellow p-nitrophenol product.
Figure 9:
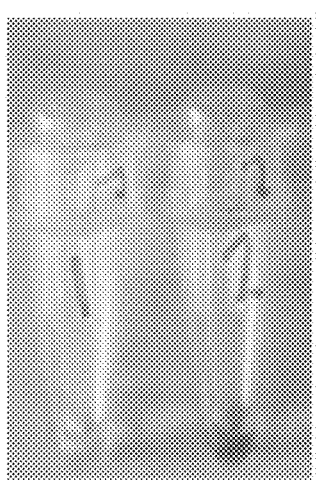
Figure 10B:
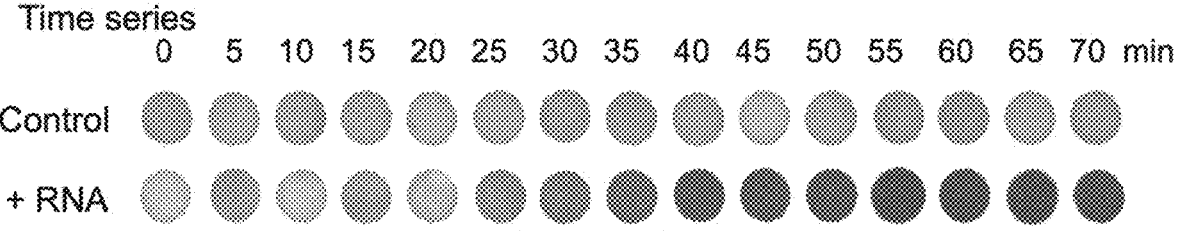
Figure 10C:
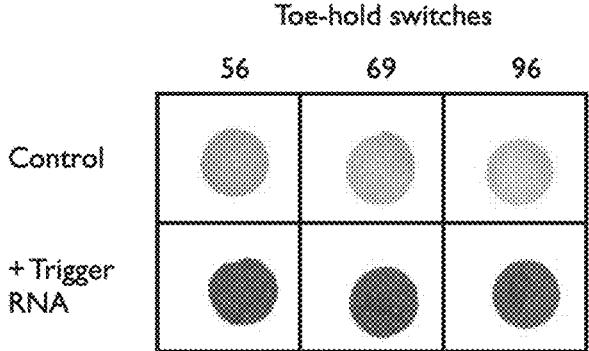

The inventor has demonstrated a wide range of fluores-cent or colorimetric sensors based on lyophilized synthetic gene networks. In one example of an RNA sensor, the reporter component comprises the gene that encodes the enzyme LacZ. The analyte being detected is a specific RNA molecule, which can activate the translation of LacZ in the presence of a cell-free system comprising components for the translation. LacZ is known in the art to cleave the yellow chlorophenol Red-β-D-galactopyranoside (CPRG) substrate to produce the purple chlorophenol red product. Because the RNA sensor also comprises the yellow chlorophenol Red-β-D-galactopyranoside (CPRG) substrate, a color change from yellow to purple can indicate the detection of the RNA (FIG. 10C). In another example of an RNA sensor, chitinase is used as an alternative colorimetric reporter enzyme, which cleaves the colorless 4-Nitrophenyl N,N'-diacetyl-beta-D-chitobioside substrate to a yellow p-nitrophenol product (FIG. 9)

RNA sensors can be used to detect RNAs of interest in a sample, and optionally quantitate the RNA level. RNAs of interest include, but are not limited to, antibiotic resistance genes, and mRNAs that encode proteins of interest.

In one embodiment, the reaction regions host the same sensors, and thus a plurality of samples can be tested for the same analyte.

In one embodiment, the reaction regions host different sensors, and thus a plurality of analytes can be detected on the same support or substrate.

In one embodiment, the same reaction region can host one or more different sensors.

The analyte can be a gas molecule, a small molecule, a nucleic acid, a protein, a peptide, a pathogen, a pathogen extract, a metabolite, an antibiotic drug, an explosive chemi-cal, a toxic chemical, or an industrial chemical. An industrial chemical can be a process by-product such as cellobiose, an intermediate in fuel production, or a bioreactor product such as vitamins. The analyte can be a solid, liquid or gas. In one embodiment, the analyte is a heavy metal. In one embodi-ment, the analyte is an insecticide residue. The analyte can be from a variety of samples, including, but not limited to, a biological sample, an environmental sample, a culture sample, an industry sample (e.g., biofuel production).

In some embodiments of sensors producing fluorescent signals, it would be apparent to a skilled artisan that any commercial or homemade device or system that can detect fluorescence can be used for the purpose of detecting the signals, including, but not limited to, a microscope, a fluorescence microplate reader, and a fluorescence spec-trometer.

In some embodiments of sensors producing colorimetric signals, human eyes can detect the signals within the visible spectrum, which is from about 390 nm to 700 nm. A commercial or homemade device that can detect colorimet-ric signals can be used as well, including, but not limited to a camera and a microscope.

In some embodiments of sensors producing electronic signals, it would be apparent to a skilled artisan that any commercial or homemade device or system that can measure electronic signals can be used for the purpose of detecting the signals. Exemplary devices or systems include a multi-meter, an ohmmeter, a voltmeter, an ammeter, and an oscilloscope.

For signal detection, an automatic device or system can permit continuous monitoring and significantly increase the detection throughput.

In one embodiment, the sensor can detect temperature, pressure, humidity, light intensity, light spectrum, or a combination thereof.

In another aspect, the synthetic gene network comprises a logic circuit, and thus can perform one or more logic functions upon activation. In the field of synthetic biology, significant progress has been made in designing and assem-bling biological components into logic circuits that can mimic or even outperform electronic circuits, resulting in the creation of a large variety of logic circuits. See WO2014093852 for examples.

In one embodiment, the logic circuit can be activated by contacting the logic circuit with water.

In one embodiment, the logic circuit can be activated by contacting the logic circuit with water and a composition comprising one or more triggers. By way of examples only, an AND gate is one of the most basic logic circuits, requiring the simultaneous presence of two appropriate triggers in order for the AND gate to turn on. If only one of the triggers is present, the AND gate would not turn on.

The trigger can comprise temperature, pressure, humidity, light intensity, light spectrum, an electrical current, a volt-age, a chemical element, an ion, a small molecule, a peptide, a protein, a nucleic acid, an extract, or a combination thereof.

In one embodiment, signal produced by a sensor described herein can serve as a component in a logic circuit.

In one embodiment, proteins lyophilized into the reaction regions or proteins expressed by a template-directed syn-thetic reaction can form a logic function or a portion thereof.

Protein doping can be a useful way to tailor the regulatory and enzymatic environment of cell-free applications. The shelf-stable composition can be doped by a variety of proteins. In one embodiment, the shelf-stable composition further comprises a repressor protein. Without wishing to be bound by theory, the repressor protein can improve the performance of some synthetic gene networks. For example, the repressor protein can prevent or reduce the probability of a reporter component producing a signal absent of an analyte. In one embodiment, the repressor protein is a transcription repressor.

In some embodiments, the shelf-stable composition further comprises an amplification system. The amplification system comprises, e.g., a set of reagents sufficient for the amplification of nucleic acids (e.g., RNA or DNA). For example, the target RNA can be amplified prior to its detection, thus resulting in better signal-over-noise ratio. In one embodiment, the amplification is isothermal amplification (see, e.g., Yan et al., Molecular BioSystems, 2014, 10, 970-1003). In one embodiment, the amplification system comprises the DNA polymerase Phi 29. Information regarding the use of Phi29 for amplification is disclosed, for example, in Dean et al., Genome Research, 2001, 11, 1095-1099.

Lyophilization, also known as freeze-drying, is a dehydration process that involves freezing a material and then reducing the surrounding pressure to allow water to sublimate. Parameters such as freezing temperature, rate of temperature change, and pressure are variables for different lyophilization process. Accordingly, the lyophilization processes used in the methods and compositions herein are not limited to a specific set of parameters. It should be apparent to a skilled artisan that preferred lyophilization processes would yield a shelf-stable composition with a long shelf life. Once the synthetic gene networks and/or cell-free systems are frozen, they should be kept frozen, i.e., prevented from thawing, until the application of low pressure (e.g., vacuum). This can present a challenge when time is needed to transport low-volume frozen synthetic gene networks and/or cell-free systems to the lyophilizer. This can be addressed, for example, by placing cold and dense materials (e.g., metal or acrylics that have been frozen at −80° C. or in liquid nitrogen) in contact with the synthetic gene networks and/or cell-free systems to serve as a cold source during transit to the lyophilizer. The material can have large heat capacity. In one embodiment, the frozen synthetic gene networks and/or cell-free systems are substantially shielded from light during the lyophilization process. This is particularly useful for protecting components sensitive to light.

Instruments for performing lyophilization are commercially available through vendors such as Cole-Parmer and Millrock Technology. In one embodiment, the shelf-stable composition is produced by a process comprising contacting a solid support with an aqueous solution comprising a cell-free system and a synthetic gene network, and lyophilizing said solid support.

In some embodiments, when stored at room temperature (i.e., about 20° C. to 24° C.) and relative humidity of no more than 10%, the composition has a shelf life of at least two weeks, at least one month, at least two months, or at least six months.

In one embodiment, the compositions described herein can function at room temperature. To increase the reaction efficiency of the compositions, in one embodiment, the temperature at which the compositions function is about 37° C. The use of thermostable enzymes permits the use of temperatures above 37° C.

In one embodiment, the compositions described herein can function when a certain temperature threshold is reached. In one embodiment, the temperature threshold is about 37° C. The use of thermostable enzymes permits the use of temperatures above 37° C.

It should be noted that the disclosed technology intends to also encompass any type of lyophilized synthetic biological circuits, such as those substantially free of template nucleic acids. For example, an engineered signaling pathway can be lyophilized on a solid support; a solution comprising a kinase can be used to activate the pathway and amplify input. There are two main types of engineered signaling pathway: those that rewire existing signal transduction pathways, and those that create artificial signaling modules. More details about engineered signaling pathways can be found, for example, in Kiel et al., Cell 2010, 140, 33-47, and Grubelnik et al., Biophysical Chemistry 2009, 143, 132-138, the contents of each of which are incorporated herein by reference in their entirety.

A related aspect of the methods and compositions described herein relates to a shelf-stable composition comprising a lyophilized synthetic gene network. In one embodiment, the shelf-stable composition is a powder, which can be in any of a variety of containers. For example, the lyophilized synthetic gene network can be in a container such as a tube, a bottle, or a vial. In one embodiment, the shelf-stable composition a lyophilized synthetic gene network can be rehydrated to form a solution.

The disclosed technology also intends to encompass any intermediate product produced in the lyophilization process. For example, the disclosed technology encompasses frozen cell-free systems and/or synthetic biological circuits (e.g., synthetic gene networks), which can become active upon thawing.

Other aspects of the disclosed technology relate to various applications of the shelf-stable compositions described herein. More specifically, one aspect regards a method of detecting an analyte, comprising providing a shelf-stable composition as described herein, wherein the composition comprises a sensor as described herein, contacting the composition with the analyte in the presence of water, and detecting a signal, wherein detection of the signal indicates the presence of the analyte. In one embodiment, the method further comprises a step of preventing or slowing water evaporation. In one embodiment, the step comprises contacting the composition with a barrier to water evaporation. The barrier is a physical barrier including, but not limited to, a tape, a film, a glass slide, a cover, and a solution that is immiscible with water (e.g., oil). In one embodiment, the step comprises enclosing the composition in an enclosure that limits evaporation of water.

In order to produce a detectable signal, the synthetic gene networks and cell-free systems generally require an incubation period. Incubation at a given temperature (often, e.g., 37° C.) can proceed on the order of seconds, minutes, or hours, depending upon the exact system. As noted in the Examples herein, in some embodiments, the reaction continues to generate a product or signal with continuing incubation, permitting the generation of a reaction curve for accumulation of signal.

In one embodiment, the method produces a qualitative output (e.g., positive or negative). For example, a positive output means that the analyte is detected, while a negative output means that the analyte is not detected.

In one embodiment, the method produces a quantitative output. The term "quantitative" is used herein to also encompass semi-quantitative. In one embodiment, quantification can be done by comparing a signal produced by a sensor against a negative control and then quantifying the signal intensity vs. time. In some embodiments, a control reaction or a set of control reactions with varying known amounts of analyte can serve to provide quantitation of analyte in an unknown sample. In one embodiment of RNA sensors, an inert RNA can be used to define a threshold for the RNA sensor.

Another aspect of the technology disclosed herein regards a method of activating a synthetic gene network lyophilized on a solid support, comprising providing a shelf-stable composition as described herein, wherein the composition comprises the synthetic gene network, and contacting the composition with water or an aqueous sample.

A related aspect of the technology disclosed herein regards a method of activating a lyophilized synthetic gene network, the method comprising providing a lyophilized cell-free system comprising components sufficient for a template-directed synthetic reaction, and contacting the lyophilized synthetic gene network with the lyophilized cell-free system in the presence of water.

Yet another aspect of the technology disclosed herein relates to a kit comprising a shelf-stable composition as described herein and packaging materials thereof. In one embodiment, the kit further comprises an enclosure, wherein said enclosure encloses the composition during a template-directed synthetic reaction to slow or prevent water evaporation.

In one embodiment, described herein is a paper-based synthetic gene network in a reader or a detection device, wherein the reader or detection device detects a signal produced by the synthetic gene network. In one embodiment, the paper-based synthetic gene network is disposed on a support during the detection.

Fields of Applications

In Vitro Diagnostics

For applications in the in vitro diagnostics space, paper-based transcription and/or translation reactions can be used to host nucleic acid-based sensor programs. In combination, these components are used to build devices that can detect, for example, the presence of pathogens and environmental contaminants, as well as measure other parameters of patient physiology, the chemical environment, and biological signals from the environment.

Synthetic Biology

As described herein, proteins synthesized using the compositions described herein are properly folded, as evidenced by fluorescent proteins that rely on their properly folded structure for fluorescence (e.g., GFP, mCherry, Cerulean, or Venus). In addition, the examples described herein demonstrate that proteins with enzymatic activity (e.g., Beta-galactosidase or Chitinase) can be synthesized using the compositions described herein and such proteins can be produced in sufficient quantity to modify substrates (e.g., CPRG or Chitin). The examples described herein also demonstrate that molecular tools capable of performing tasks (e.g., RNA toehold switches or the FRET-based nanosensor) can be synthesized using the compositions described herein.

Accordingly, the compositions and methods described herein also offer a new venue for synthetic biology at large. Beyond in vitro diagnostics, the compositions and methods described herein provide a much-needed medium for the commercialization of synthetic biology. This approach can permit the straightforward, sterile and abiotic distribution of synthetic biology-based technology to clinical settings, food processing and industry, the military and consumer products. This could encompass embedding sensors, counters and timers and other synthetic gene networks into products, as well as tools for molecular manufacturing. Examples of the latter include the on-demand, on-site manufacturing of pharmaceuticals, therapeutic proteins and other biomolecules or biomaterials. Much like 3-D printing technology, these applications can make scalable molecular synthesis available to anyone with the freeze-dried reagent and a library of "molecular programs." Molecular manufacturing using the compositions and/or methods described herein can be done in a portable manner for applications both in the lab and outside of the laboratory, and without the need of a cold chain.

In one embodiment of molecular manufacturing, a virus can be synthesized using the compositions and/or methods described herein. Preferably, the virus is a non-enveloped virus. Non-enveloped virus can come from families including, but not limited to, Adenoviridae (e.g., adenovirus, infectious canine hepatitis virus), Papovaviridae (e.g., papillomavirus, polyomaviridae, simian vacuolating virus), Parvoviridae (e.g., parvovirus B19, canine parvovirus), Anelloviridae (e.g., torque teno virus), Caulimoviridae (e.g., cauliflower mosaic virus), Myoviridae, Phycodnaviridae, Tectiviridae, Circoviridae, Reoviridae (e.g., Reovirus, rotavirus), Picornaviridae (e.g., Enterovirus, rhinovirus, hepatovirus, cardiovirus, aphthovirus, poliovirus, parechovirus, erbovirus, kobuvirus, teschovirus, coxsackie), Caliciviridae (e.g., Norwalk virus), Astroviridae (e.g., Astrovirus), Hepeviridae (e.g., Hepatitis E virus), Birnaviridae (e.g., Chicken proventricular necrosis virus), and Potyviridae.

For virus synthesis, a freeze-dried composition comprising a cell-free system and a set of nucleic acids encoding an appropriate set of proteins (e.g., capsids) of the virus of interest can be used. When the freeze-dried composition is activated, e.g., by the addition of water, proteins can be synthesized in vitro and then self-assemble to form the virus. When incorporated into a wound dressing, topical preparation, or implantable device or preparation, the virus would be assembled at the site of application. This can permit, e.g., viral vector production at the site of need or simply in an individual in an on-demand manner. The freeze-dried compositions and methods for virus synthesis can be used therapeutically, e.g., for transient gene therapy, e.g., delivery of adenovirus. For the production of viral vectors by the methods and compositions described herein, nucleic acids can encode the viral protein component(s) necessary for self-assembly/packing of a viral genome construct carrying a therapeutic or cargo coding sequence of interest. Upon assembly, the genomic construct is packaged and will be delivered to host cells upon infection. In some embodiments, the assembled virus particles may not be infective and, for instance, can be used as vaccine antigens, nanoparticles, or biomaterials.

The freeze-dried compositions and methods for virus synthesis can be used in a research setting, e.g., for the delivery of viral expression constructs to mammalian cells. Many small aliquots of viruses can be produced in this manner for high-throughput screening. The freeze-dried compositions and methods for virus synthesis can also be used in vaccine production for viruses or other microbial agents, such as rotavirus. Alternatively, viral proteins can be expressed simply as antigens without the formation of capsids, as in vaccines for HPV (Human papillomavirus), and DTaP (Diphtheria, Tetanus, and Pertussis), among a great many others.

In one embodiment of virus manufacturing, the virus is a bacteriophage. The freeze-dried compositions and methods for bacteriophage synthesis can be used in a research setting, e.g., for the delivery of genes to bacterial cells. The freeze-dried compositions and methods for bacteriophage synthesis can also be used in therapeutic applications, e.g., phage therapy. The freeze-dried compositions and methods for bacteriophage synthesis can also be used in diagnostic applications, e.g., for the detection of pathogens.

In one embodiment of molecular manufacturing, a therapeutic protein can be synthesized using the compositions and/or methods described herein. A freeze-dried composition comprising a cell-free system and a nucleic acid encoding the protein of interest can be used. The freeze-dried composition can further comprise a synthetic gene network that can actuate the protein synthesis in response to an input or stimulus (e.g., a pathogen, an oncoprotein, a cytokine, a hormone, etc.). Examples of therapeutic proteins include, but are not limited to human amylin, insulin, growth hormone (GH), mecasermin, erythropoietin, darbepoetin-α, granulocyte colony stimulating factor, pegfilgrastim, granulocyte-macrophage colony stimulating factor, human follicle-stimulating hormone, human chorionic gonadotropin, lutropin-α, cytokines (e.g., interferons such as interferon alfacon 1, interferon-α2a), aldesleukin, Hepatitis B surface antigen (HBsAg), HPV protein vaccine, OspA, and antimicrobial peptides. See Leader et al., Nature 2008, 7, 21-39 for more examples of therapeutic proteins that can be genetically expressed or produced according to the methods described herein.

In one embodiment, the therapeutic protein is an antibody or an antigen-binding fragment thereof. Non-limiting examples of therapeutic antibodies include, but are not limited to, bevacizumab, cetuximab, panitumumab, alemtuzumab, rituximab, trastuzumab, abatacept, infliximab, enfuvirtide, crotalidae, and ranibizumab. The antibody or fragment thereof can be linked to a drug (e.g., a chemotherapeutic drug) for targeted delivery. Production of antibodies or fragments thereof can also be used in a research setting.

In one embodiment, the therapeutic protein is an enzyme, e.g., phenylalanine hydroxylase for the treatment of phenylketonuria.

In one embodiment of molecular manufacturing, components for a drug synthesis pathway can be synthesized using the compositions and/or methods described herein. In one embodiment, the components for a drug synthesis pathway can convert an inactive bioprecursor pro-drug to a bioactive form. Indeed, even expression of a single enzyme in a spatially or temporally restricted manner permitted by the on-demand manufacture of proteins as described herein can be used to convert a pro-drug to an active drug in a user-regulated way. One example of a pro-drug is peptide-appended therapeutics, which can be activated by proteolytic cleavage of the peptide moiety. In such cases, therapeutics can be released from engineered materials in wound dressings by expressed proteases. In one embodiment, the drug synthesis pathway can be a pathway that converts a stable, inexpensive precursor to a drug, e.g., cholesterol to steroid, or amorphadiene to artemisinin, which is used to treat malaria.

In one embodiment of molecular manufacturing, nanoparticles can be synthesized using the compositions and/or methods described herein. A freeze-dried composition comprising a cell-free system and a nucleic acid encoding a metal-binding protein can be used. The metal-binding protein can facilitate the synthesis of nanoparticles of interest. See for example, Lee et al., ACS Nano 2012, 6, 6998-7008. Examples of nanoparticles include, but are not limited to, quantum dots, metal nanoparticles such as gold or iron nanoparticles.

In one embodiment of molecular manufacturing, oligonucleotides can be synthesized using the compositions and/or methods described herein. Preferably, the oligonucleotides synthesized undergo folding and/or self-assembling to form DNA (deoxyribonucleic acid) or RNA (ribonucleic acid) origami construct. DNA itself is normally unstable upon in vivo administration. However DNA origami constructs and new strategies increasing the in vivo stability of such constructs are being developed for their use in therapeutics. See, for example, Douglas et al., Science 2012, 335, 831-834.

For any of the molecular manufacturing aspects described herein, it is contemplated that the expression of the desired product can be made sensitive to the presence of another molecule or agent by integrating a synthetic gene network that acts as a sensor into the design. In such instances, the desired gene product is only made when the molecule or agent is present, and that agent can be, e.g., a pathogen, a metabolite, a protein, or even a small molecule administered separately.

Molecular Programming/Computing

The technology disclosed herein can provide an excellent platform for DNA/RNA-based computing and logic reactions. As a part of this, a paper/electronic interface was developed that can sense computational output and the response of embedded biosensors. This can permit automation and allow for multiplexed arrays of reactions. In some embodiments, transcription reactions can express RNAs that then interact with a network of catalytic nucleic acids, which can be used in signal amplification.

General Molecular Biology

Broader applications for this technology include its use in basic research for the assembly and testing of new genetic constructs and gene networks. In such usage, paper-based transcription and translation reactions would serve as a mock cell, allowing for linear PCR products to be screened directly for function without purification, sequencing or assembly into circularized plasmids. This approach is significantly less expensive than the current purification/sequencing methods and permits researchers to determine their best performing design in about one hour rather than having to wait overnight.

The cell extracts used to supply the transcription and translation machinery also offer a unique opportunity for molecular biologists to work with organisms that are difficult to culture. By generating cell extracts from mutant cell lines, pathogens or other specialized organisms (e.g., extremophiles, symbionts), the biology of otherwise inaccessible systems can be made available to the broader research community. Such accessibility could greatly increase the development of therapeutics and the application of biology in engineering.

Unlike the commercially available antibody-based rapid diagnostic tests (RDTs), nucleic acid-based sensors can be designed to directly detect one or more orthogonal, species-specific RNAs. This sequence-based method of detection means that tools can be designed rationally, lowering development costs and allowing for a short design to production cycle. The sequence-based sensors also permit the acquisition of other relevant clinical information, such as the presence of drug-resistance genes or other indicators of pathogenesis, such as biofilm-specific RNAs. Thresholding of the nucleic acid-based sensors also allows for semi-quantitative diagnostics, a much needed feature that is for the most part not available with RDTs (Michael S. Cordray and Rebecca R. Richards-Kortum, Am. J. Trop. Med. Hyg., 2012, 87, 223-230). In one embodiment, quantification can be done without thresholding. For example, see FIG. 26, where a linear relationship exists for RNA concentration in the range of 0-2 μM.

The sensors described herein are also less expensive than most of the standard of care options currently available. At the moment, the cost per sensor as described herein is between about 35 ¢-60 ¢ using commercial cell-free systems. However, these systems can be readily produced in house, reducing the cost to as little as 4 ¢ per sensor (which can be found on the world wide web at openwetware.org/wiki/Biomolecular_Breadboards:Protocols:cost_estimate). This compares to $0.45-$1.40 for a single RDT reaction and $1.50-$4.00 (reagents only) for PCR (Michael S. Cordray and Rebecca R. Richards-Kortum, Am. J. Trop. Med. Hyg. 2012, 87, 223-230). The compositions and methods described here are also competitive with regard to how long it takes to make a positive identification. The sensors described herein can yield positive results in as little as 25 minutes depending on the sensor format, with most sensors functioning with a reaction time of under an hour. This compares to RDTs, which can detect a single antigen in ~20 minutes or PCR, which can take 1.5 to 2 hours and is largely confined to laboratory settings.

Some embodiments of the invention are listed in the following numbered paragraphs:

paragraph 1. A shelf-stable composition comprising a cell-free system comprising components sufficient for a template-directed synthetic reaction, wherein said cell-free system is lyophilized on a porous substrate and is substantially free of water, and wherein said cell-free system is active for said template-directed synthetic reaction upon re-hydration.

paragraph 2. The shelf-stable composition of paragraph 1, further comprising a synthetic gene network.

paragraph 3. The shelf-stable composition of paragraph 2, wherein said synthetic gene network comprises nucleic acids.

paragraph 4. The shelf-stable composition of paragraph 3, wherein said nucleic acid comprises DNA, RNA, an artificial nucleic acid analog, or a combination thereof paragraph 5. The shelf-stable composition of any of paragraphs 1 to 4, wherein said template-directed synthetic reaction is a transcription reaction.

paragraph 6. The shelf-stable composition of any of paragraphs 1 to 4, wherein said template-directed synthetic reaction is a translation reaction.

paragraph 7. The shelf-stable composition of any of paragraphs 1 to 4, wherein said template-directed synthetic reaction is a coupled transcription and translation reaction.

paragraph 8. The shelf-stable composition of paragraph 1, wherein said components are sufficient for a transcription reaction, and comprise promoter-containing DNA, RNA polymerase, ribonucleotides, and a buffer system.

paragraph 9. The shelf-stable composition of paragraph 1, wherein said components are sufficient for a translation reaction, and comprise ribosomes, aminoacyl transfer RNAs, translation factors, and a buffer system.

paragraph 10. The shelf-stable composition of paragraph 1, wherein said components are sufficient for a coupled transcription and translation reaction, and comprise promoter-containing DNA, RNA polymerase, ribonucleotides, ribosomes, aminoacyl transfer RNAs, translation factors, and a buffer system.

paragraph 11. The shelf-stable composition of any of paragraphs 1 to 10, wherein said porous substrate comprises paper, quartz microfiber, mixed esters of cellulose, porous aluminum oxide, or a patterned surface.

paragraph 12. The shelf-stable composition of any of paragraphs 1 to 11, wherein said porous substrate is pre-treated with bovine serum albumin, polyethylene glycol, Tween-20, Triton-X, milk powder, casein, fish gelatin, or a combination thereof paragraph 13. The shelf-stable composition of any of paragraphs 1 to 12, wherein said cell-free system comprises a whole cell extract or a recombinant protein transcription/translation system.

paragraph 14. The shelf-stable composition of paragraph 13, wherein said whole cell extract is selected from the group consisting of rabbit reticulocyte lysate, wheat germ extract, *E. coli* extract, and human cell extract.

paragraph 15. The shelf-stable composition of paragraph 13, wherein the recombinant protein transcription/translation system is reconstituted from purified components necessary for *E. coli* translation.

paragraph 16. The shelf-stable composition of any of paragraphs 2 to 15, wherein said synthetic gene network functions as a sensor.

paragraph 17. The shelf-stable composition of paragraph 16, wherein said sensor can detect the presence of an analyte in an aqueous sample.

paragraph 18. The shelf-stable composition of paragraph 17, wherein detection of said analyte produces an optical signal.

paragraph 19. The shelf-stable composition of paragraph 17, wherein detection of said analyte produces an electronic signal.

paragraph 20. The shelf-stable composition of any of paragraphs 2 to 15, wherein said synthetic gene network comprises a logic circuit.

paragraph 21. The shelf-stable composition of paragraph 20, wherein said logic circuit comprises an AND gate, a NOT gate, an OR gate, a NOR gate, a NAND gate, a XOR gate, a XAND gate, or a combination thereof.

paragraph 22. The shelf-stable composition of paragraph 20 or 21, wherein said logic circuit is activated upon contacting said shelf-stable composition with water and a composition comprising a trigger.

paragraph 23. The shelf-stable composition of paragraph 22, wherein said trigger is selected from the group consisting of a chemical element, a small molecule, a peptide, a protein, a nucleic acid, an extract, and a combination thereof.

paragraph 24. The shelf-stable composition of any of paragraphs 1 to 23, characterized in that the shelf-stable composition is shelf stable for at least two weeks.

paragraph 25. A shelf-stable composition comprising a cell-free system comprising components sufficient for a template-directed synthetic reaction, a synthetic gene network, and a solid support, wherein said shelf-stable composition is substantially free of water, and wherein said cell-free system is active for said template-directed synthetic reaction upon rehydration.

paragraph 26. The shelf-stable composition of paragraph 25, wherein said synthetic gene network comprises nucleic acids.

paragraph 27. The shelf-stable composition of paragraph 26, wherein said nucleic acid comprises DNA, RNA, an artificial nucleic acid analog, or a combination thereof paragraph 28. The shelf-stable composition of any of paragraphs 25 to 27, wherein said template-directed synthetic reaction is a transcription reaction.

paragraph 29. The shelf-stable composition of any of paragraphs 25 to 27, wherein said template-directed synthetic reaction is a translation reaction.

paragraph 30. The shelf-stable composition of any of paragraphs 25 to 27, wherein said template-directed synthetic reaction is a coupled transcription and translation reaction.

paragraph 31. The shelf-stable composition of paragraph 25, wherein said components are sufficient for a transcription reaction, and comprise promoter-containing DNA, RNA polymerase, ribonucleotides, and a buffer system.

paragraph 32. The shelf-stable composition of paragraph 25, wherein said components are sufficient for a translation reaction, and comprise ribosomes, aminoacyl transfer RNAs, translation factors, and a buffer system.

paragraph 33. The shelf-stable composition of paragraph 25, wherein said components are sufficient for a coupled transcription and translation reaction, and comprise promoter-containing DNA, RNA polymerase, ribonucleotides, ribosomes, aminoacyl transfer RNAs, translation factors, and a buffer system.

paragraph 34. The shelf-stable composition of any of paragraphs 25 to 33, wherein said solid support comprises paper, quartz microfiber, mixed esters of cellulose, porous aluminum oxide, a patterned surface, a tube, a well, or a chip.

paragraph 35. The shelf-stable composition of any of paragraphs 25 to 34, wherein said solid support is pre-treated with bovine serum albumin, polyethylene glycol, Tween-20, Triton-X, milk powder, casein, fish gelatin, or a combination thereof paragraph 36. The shelf-stable composition of any of paragraphs 25 to 35, wherein said cell-free system comprises a whole cell extract or a recombinant protein transcription/translation system.

paragraph 37. The shelf-stable composition of paragraph 36, wherein said whole cell extract is selected from the group consisting of rabbit reticulocyte lysate, wheat germ extract, *E. coli* extract, and human cell extract.

paragraph 38. The shelf-stable composition of paragraph 36, wherein the recombinant protein transcription/translation system is reconstituted from purified components necessary for *E. coli* translation.

paragraph 39. The shelf-stable composition of any of paragraphs 25 to 38, wherein said synthetic gene network functions as a sensor.

paragraph 40. The shelf-stable composition of paragraph 39, wherein said sensor can detect the presence of an analyte in an aqueous sample.

paragraph 41. The shelf-stable composition of paragraph 40, wherein detection of said analyte produces an optical signal.

paragraph 42. The shelf-stable composition of paragraph 40, wherein detection of said analyte produces an electronic signal.

paragraph 43. The shelf-stable composition of any of paragraphs 25 to 38, wherein said synthetic gene network comprises a logic circuit.

paragraph 44. The shelf-stable composition of paragraph 43, wherein said logic circuit comprises an AND gate, a NOT gate, an OR gate, a NOR gate, a NAND gate, a XOR gate, a XAND gate, or a combination thereof.

paragraph 45. The shelf-stable composition of paragraph 43 or 44, wherein said logic circuit is activated upon contacting said shelf-stable composition with water and a composition comprising a trigger.

paragraph 46. The shelf-stable composition of paragraph 45, wherein said trigger is selected from the group consisting of a chemical element, a small molecule, a peptide, a protein, a nucleic acid, an extract, and a combination thereof.

paragraph 47. The shelf-stable composition of any of paragraphs 25 to 46, characterized in that the shelf-stable composition is shelf stable for at least two weeks.

paragraph 48. A shelf-stable composition produced by contacting a solid support with an aqueous solution comprising a cell-free system and a synthetic gene network, and lyophilizing said solid support.

paragraph 49. A method of detecting an analyte, comprising (i) providing a composition of any of paragraphs 1 to 47, wherein said composition comprises a nucleic acid-based sensor;

(ii) contacting said composition with said analyte in the presence of water; and (iii) detecting a signal, wherein detection of said signal indicates the presence of said analyte.

paragraph 50. The method of paragraph 49, further comprising a step of contacting said composition with a barrier to water evaporation or enclosing said composition in an enclosure after step (ii).

paragraph 51. The method of paragraph 49 or 50, wherein said method provides a measure of the amount of said analyte.

paragraph 52. The method of any of paragraphs 49 to 51, wherein said nucleic acid comprises DNA, RNA, an artificial nucleic acid analog, or a combination thereof paragraph 53. The method of any of paragraphs 49 to 52, wherein said nucleic acid-based sensor comprises a reporter gene.

paragraph 54. The method of paragraph 53, wherein said reporter gene encodes a fluorescence protein, an enzyme, or an antigen.

paragraph 55. The method of any of paragraphs 49 to 52, wherein said nucleic acid-based sensor comprises a catalytic nucleic acid.

paragraph 56. The method of any of paragraphs 49 to 52, further comprising providing a fluorophore, whereby said fluorophore can couple to a nucleic acid to produce a change in fluorescence.

paragraph 57. The method of any of paragraphs 49 to 56, wherein said analyte is selected from the group consisting of a nucleic acid, a pathogen, a pathogen extract, a metabolite, an antibiotic drug, an explosive chemical, a toxic chemical, and an industrial chemical.

paragraph 58. The method of paragraph 57, wherein said toxic chemical is a heavy metal or insecticide residue.

paragraph 59. The method of any of paragraphs 49 to 58, wherein said signal is an optical signal.

paragraph 60. The method of paragraph 59, wherein said optical signal is luminescence.

paragraph 61. The method of paragraph 59, wherein said optical signal is fluorescence.

paragraph 62. The method of paragraph 59, wherein said optical signal is a visible color.

paragraph 63. The method of any of paragraphs 49 to 58, wherein said signal is an electronic signal.

paragraph 64. The method of any of paragraphs 49 to 63, wherein the analyte is in an aqueous solution.

paragraph 65. A kit comprising a shelf-stable composition of any of paragraphs 1 to 47 and packaging materials thereof.

paragraph 66. The kit of paragraph 65, further comprising an enclosure, wherein said enclosure encloses said composition during a template-directed synthetic reaction to slow or prevent water evaporation.

paragraph 67. A method of activating a synthetic gene network lyophilized on a porous substrate, comprising:

(i) providing a shelf-stable composition of any of paragraphs 1 to 47, wherein said composition comprises said synthetic gene network; and (ii) contacting the composition with a solution comprising water.

paragraph 68. The method of paragraph 67, wherein said synthetic gene network functions as a sensor, and wherein said solution further comprises an analyte capable of activating said sensor.

paragraph 69. The method of paragraph 68, wherein said analyte is selected from the group consisting of a nucleic acid, a pathogen, a pathogen extract, a metabolite, an antibiotic drug, an explosive chemical, a toxic chemical, and an industrial chemical.

paragraph 70. The method of paragraph 67, wherein said synthetic gene network comprises a logic circuit, and wherein said solution further comprises a trigger capable of activating said logic circuit.

paragraph 71. The method of paragraph 70, wherein said trigger is selected from the group consisting of a chemical element, a small molecule, a peptide, a protein, a nucleic acid, an extract, and a combination thereof.

paragraph 72. A method of activating a lyophilized synthetic gene network, comprising (i) providing a lyophilized cell-free system comprising components sufficient for a template-directed synthetic reaction; and (ii) contacting said lyophilized synthetic gene network with said lyophilized cell-free system in the presence of water.

paragraph 73. A method of stabilizing a synthetic gene network, comprising lyophilizing said synthetic gene network.

paragraph 74. The method of paragraph 73, wherein said synthetic gene network is on a solid support during lyophilization.

paragraph 75. The method of paragraph 74, wherein the solid support is paper.

paragraph 76. A shelf-stable composition of any of paragraphs 1 to 47 and a reader, wherein said reader can measure a signal from said shelf-stable composition.

paragraph 77. A shelf-stable composition comprising a lyophilized synthetic biological circuit.

paragraph 78. The shelf-stable composition of paragraph 77, wherein the synthetic biological circuit is lyophilized on a porous substrate.

paragraph 79. The shelf-stable composition of paragraph 77 or 78, wherein the synthetic biological circuit is a synthetic gene network.

paragraph 80. The shelf-stable composition of paragraph 79, further comprising a cell-free system.

paragraph 81. The shelf-stable composition of paragraph 77 or 78, wherein the synthetic biological circuit is an engineered signaling pathway.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to describe the present invention, in connection with percentages means+1%, or +5%. For example, about 100 means from 95 to 105.

In one respect, the present invention relates to the herein described compositions, methods, and respective component (s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Figure 1B:
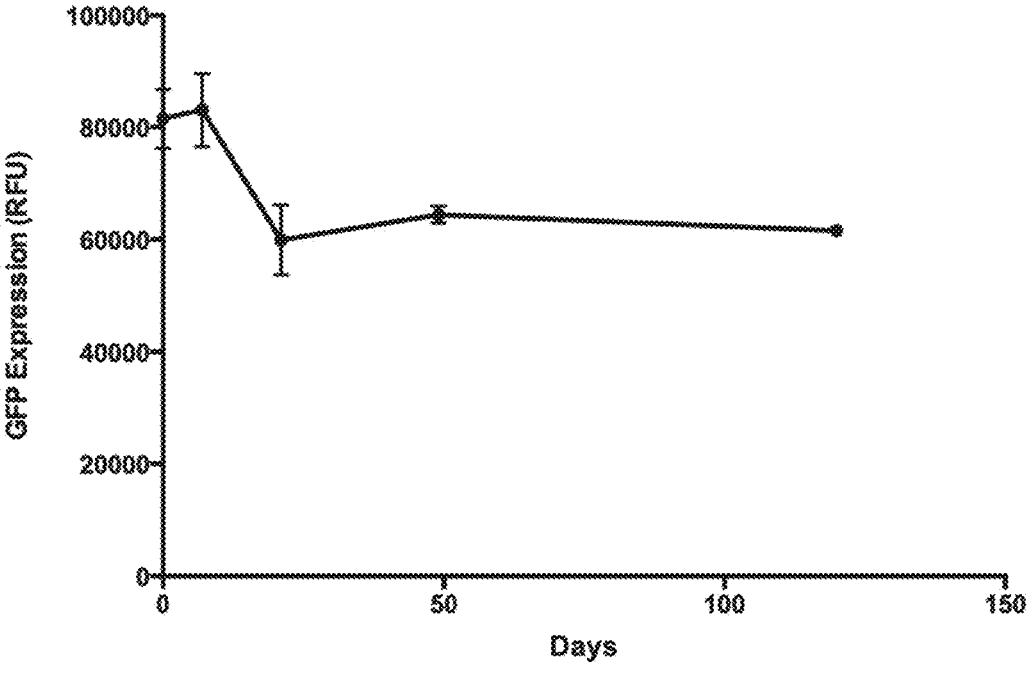
Figure 2A:
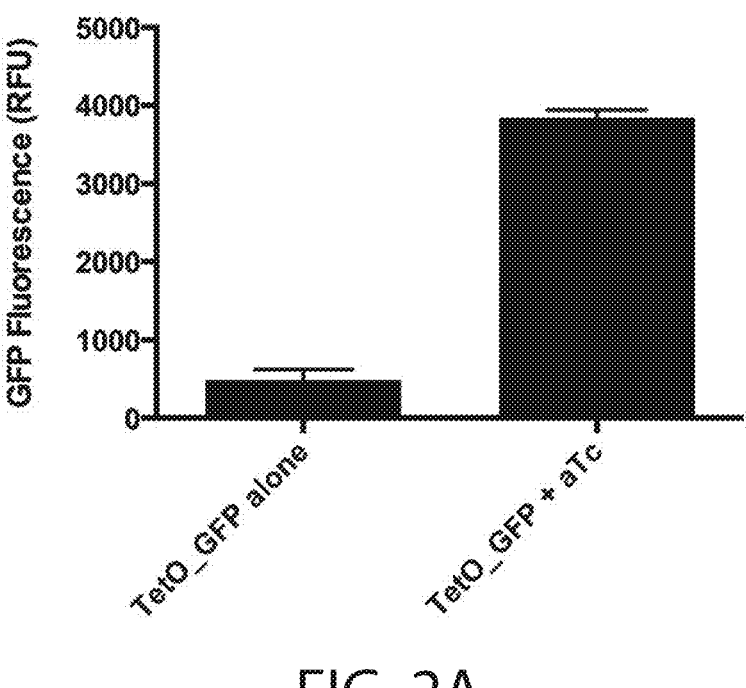
FIGS. 2A-2B show that freeze-dried whole bacterial cell extracts support inducible expression from an *E. coli* RNA polyermase (RNAP) based construct. Here GFP (FIG. 2A) and mCherry (FIG. 2B) expression was induced from the TetO promoter using a chemical analog to the antibiotic doxycycline (e.g., anhydrotetracycline, aTc).
Figure 2B:
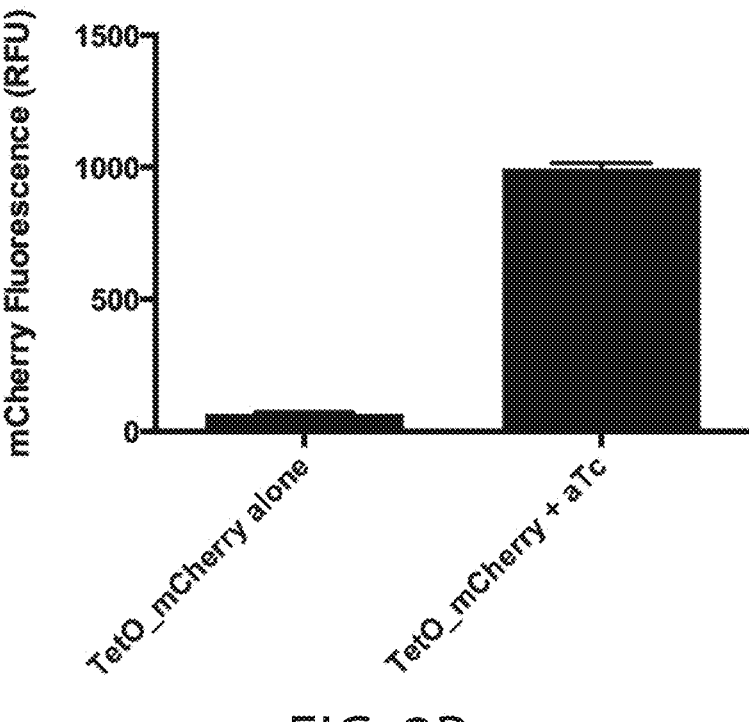
Figure 3B:
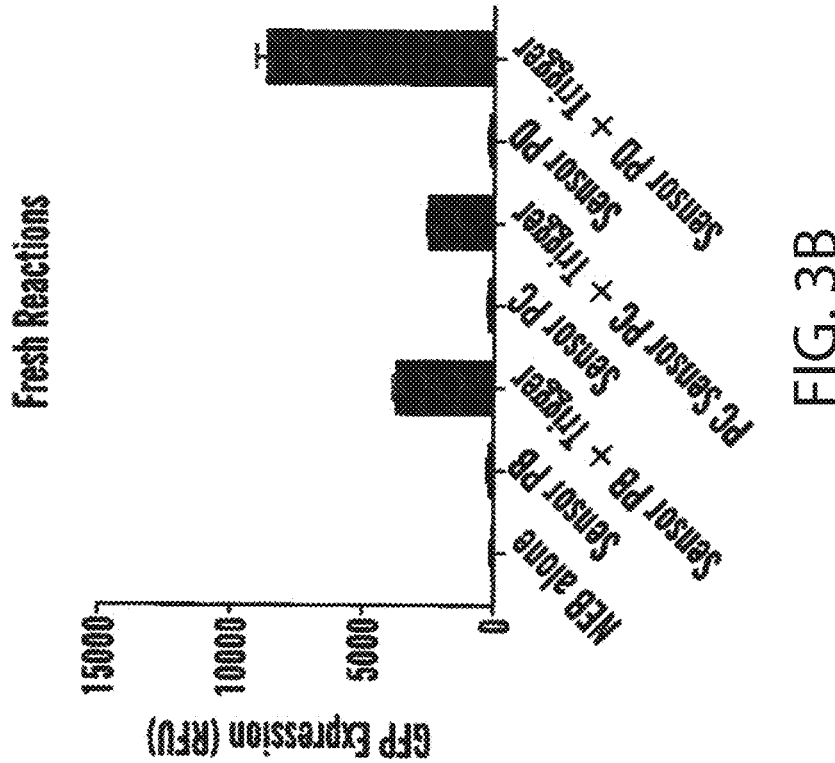
FIGS. 3A-3C show that freeze-dried T7 cell-free expression systems (FIG. 3C) have comparable expression characteristics to T7-mediated expression in *E. coli* (FIG. 3A) or T7-based fresh reaction (FIG. 3B). Freeze dried T7 whole extracts or recombinant cell-free systems can support inducible expression from plasmid DNA, linear dsDNA and ssRNA templates. Here GFP expression is induced from Toe-hold switches (riboswitches) by short trigger RNA.
Figure 3A:
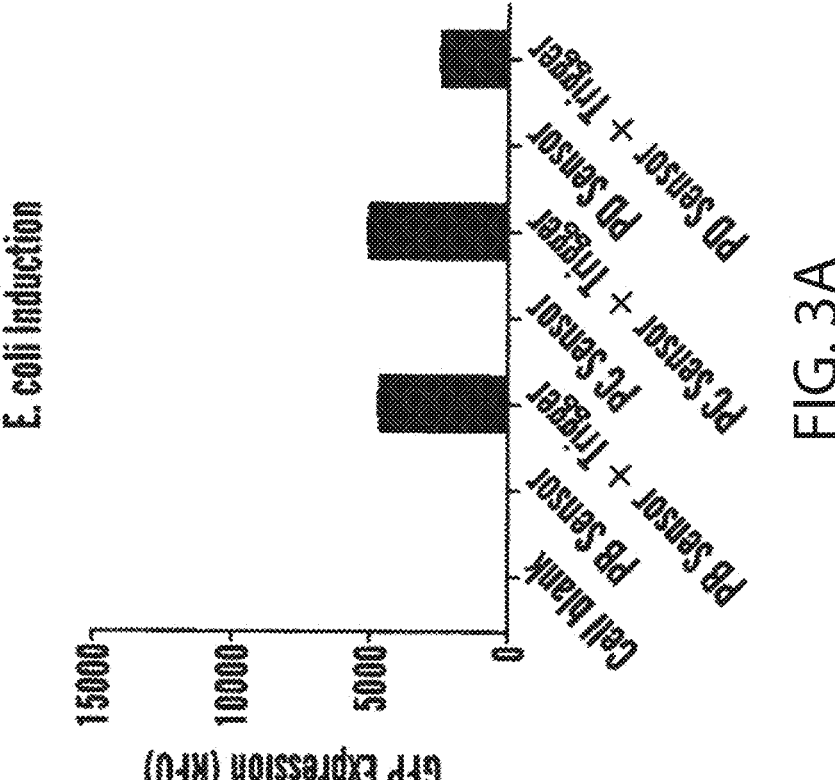
Figure 3C:
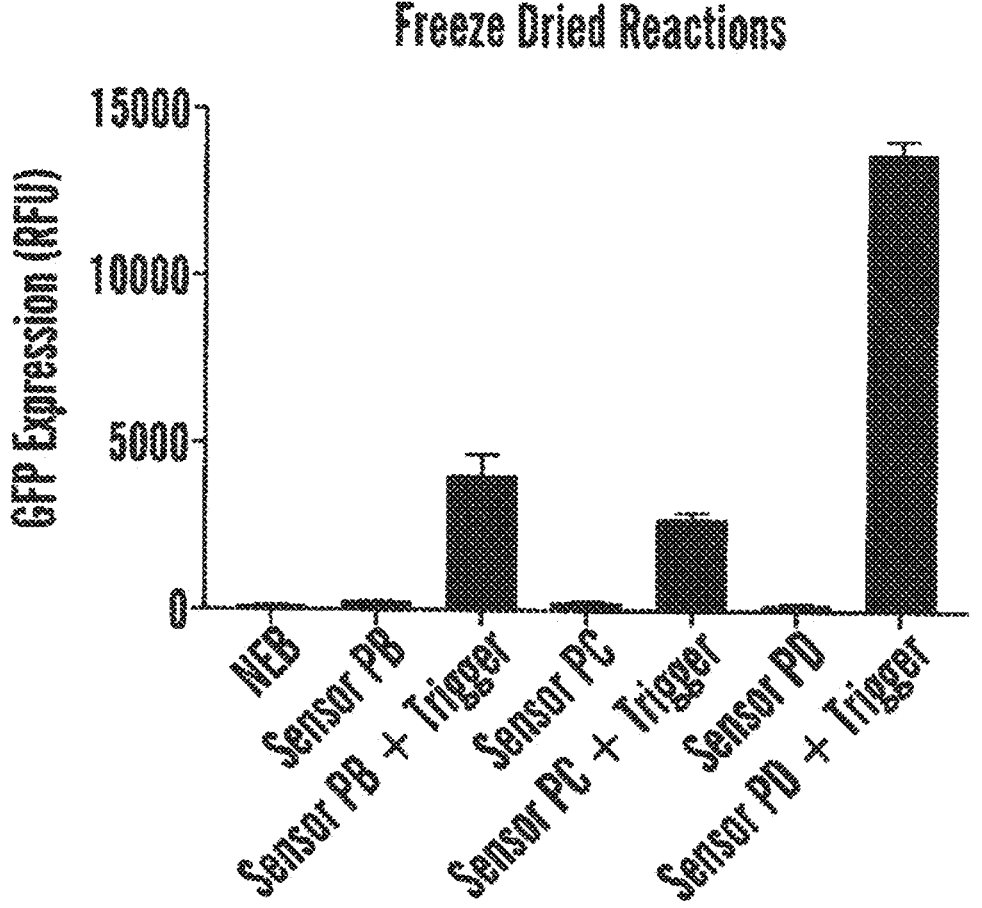

Example 1: Lyophilized Sensors Comprising Synthetic Gene Networks and Cell-Free Systems It was first demonstrated that freeze-dried cell extracts can support the constitutive expression of GFP, via *E. coli* RNA polymerase or T7 RNA polymerase based promoters (FIG. 1A). The later T7-based expression can also be supported by freeze drying a recombinant protein-based system. These results essentially reflect the expression levels observed in fresh cell-free reactions and in *E. coli*. The freeze dried cell-free systems are stable over time with transcription and translation activity remaining high after months of room temperature storage (FIG. 1B).

Figure 8A:
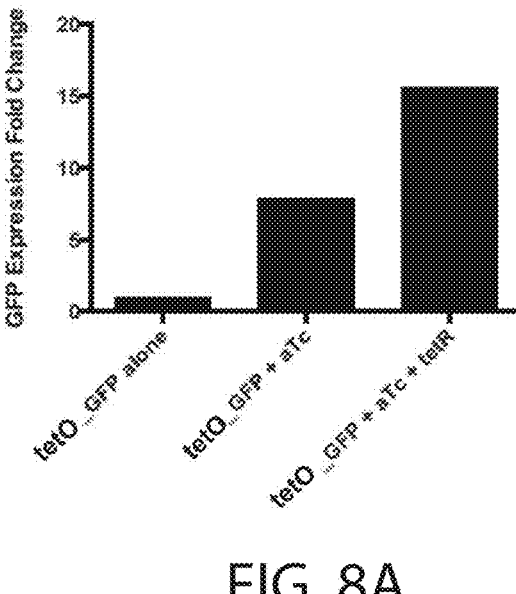
FIGS. 8A-8B show a comparison of TetO-based induction between standard cell extracts and cell extracts doped with tetR before freeze drying. By adding tetR prior to freeze-drying, leaky expression for the tetO promoter is minimized, resulting in much greater fold-change and control over gene expression.
Figure 8B:
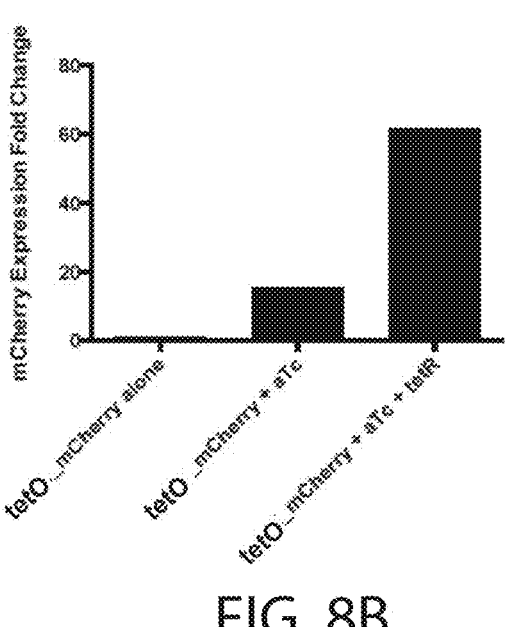

Inducible expression systems were used for synthetic gene networks. Using the classic inducible tetO promoter, induced by the antibiotic doxycycline or chemical analogs, GFP expression was readily induced. Of note, tight regulatory control in vitro required that cell extracts be supplemented with tet repressor (tetR) protein to prevent reporter leakage prior to repressor expression from a constitutive tetR element in the gene circuit (FIG. 8A). This successful tetR augmentation of cell-free systems prior to freeze-drying suggests protein doping can be a useful way to tailor the regulatory and enzymatic environment of cell-free applications. For the inducible regulation of the potent T7 promoter, a new generation of RNA-inducible riboswitches, called toe-hold switches, is chosen. These robust switches provided tight, almost complete, regulation over the T7 transcripts, with GFP only being produced in the presence of the correct RNA trigger (FIGS. 10A-10C).

Figure 5A:
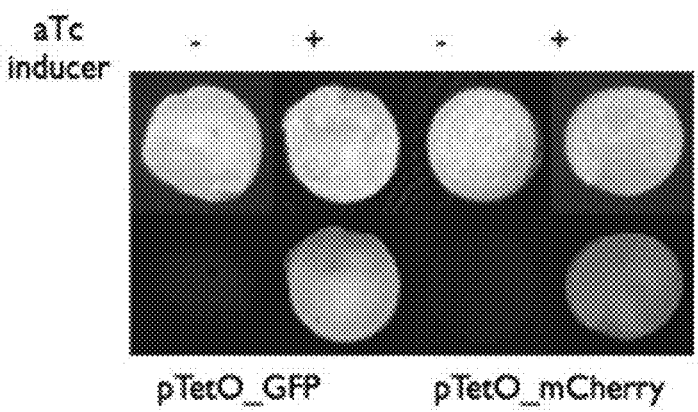
FIGS. 5A-5C show that embedded freeze-dried cell-free expression systems support transcription and translation reactions on quartz microfiber or filter paper discs (both pre-treated with 50 mg/ml BSA).
Figure 5B:
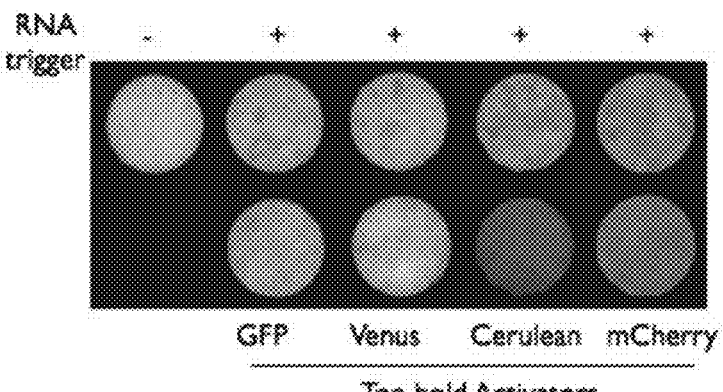
Figure 5C:
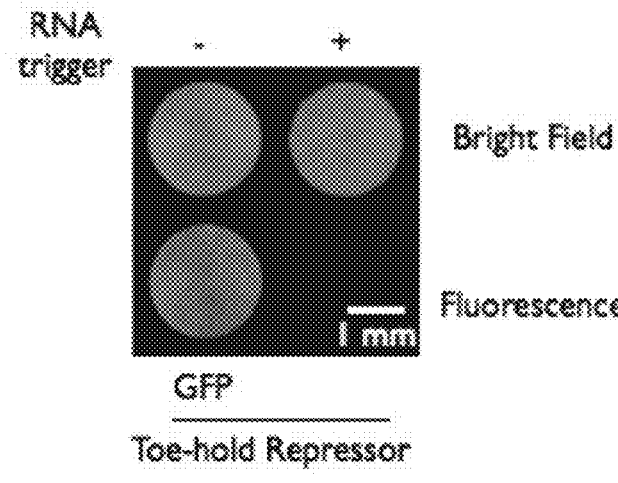
Figure 11A:
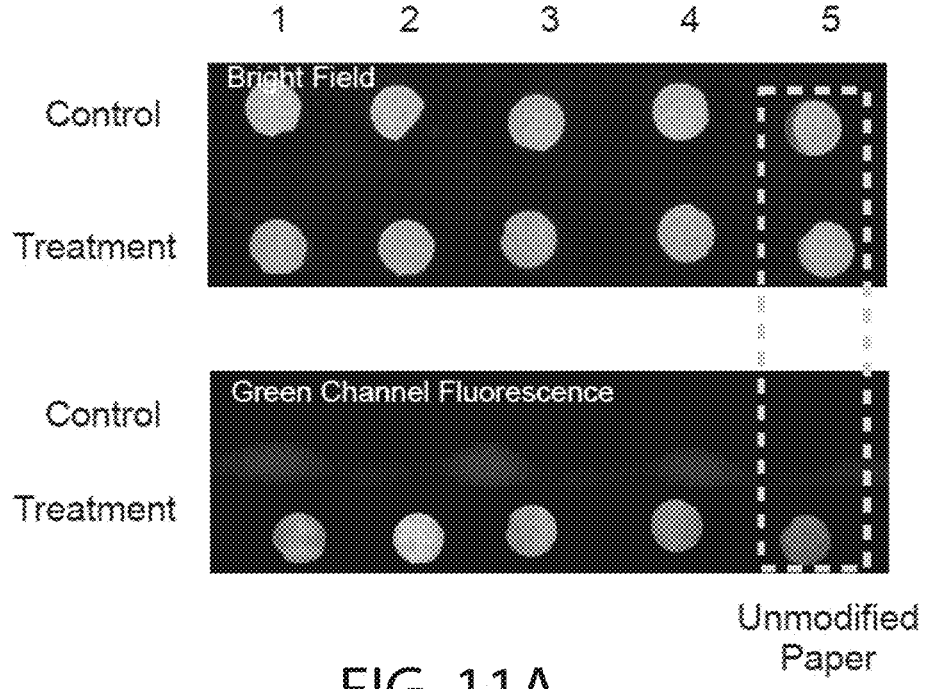
FIGS. 11A-11B show that paper- or quartz-based reactions perform better when paper or quartz has been pre-treated.
Figure 11B:
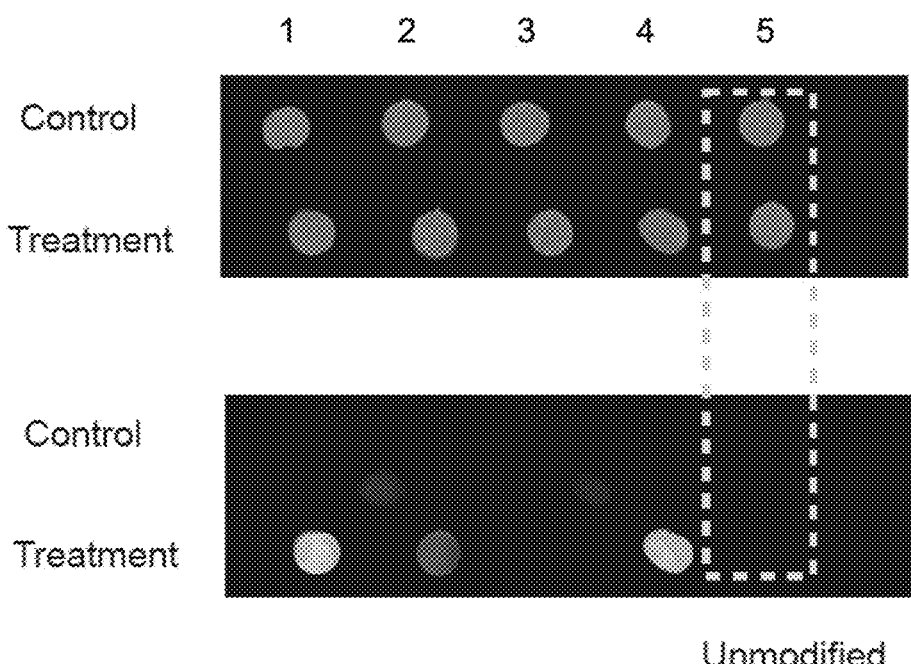

To host these freeze-dried applications, the cell-free systems and synthetic gene networks are embedded into paper and other porous materials. Paper, previously used in chemistry-based diagnostics (Martinez et al., Angew. Chem. Int. Ed., 2007, 46, 1318-1320), serves as a high capillary matrix that evenly distributes small volume reactions and provides a surface for the display of gene circuit outputs. It was found that first treating the paper with BSA or other similar blocking reagents significantly improved the output of expression constructs (FIG. 11A). Small 2 mm filter paper discs were freeze dried with cell-free systems to produce GFP from either *E. coli* RNA polymerase or T7 polymerase-based expression plasmids. As in solution phase, constitutive expression from either promoter yields a consistent fluorescence and inducible expression behaves with dynamics comparable to both in vivo and solution phase in vitro reactions. Cellulose fibers carry an inherent autofluorescence around the emission spectrum of GFP, and so inducible systems that output with fluorescent proteins with alternate emission spectra have also been constructed. With these alternate reporters, the same paper disc can be used to host multiple sensors (FIG. 5B). Multiple outputs from sensors embedded in quartz microfiber and paper discs have been demonstrated. Such diversity of outputs can also be displayed using paper segmented by printed lithography rather than paper discs, with hydrophobic barriers separating the respective reaction spaces (FIG. 4).

Figures 6, 7A, 7B:
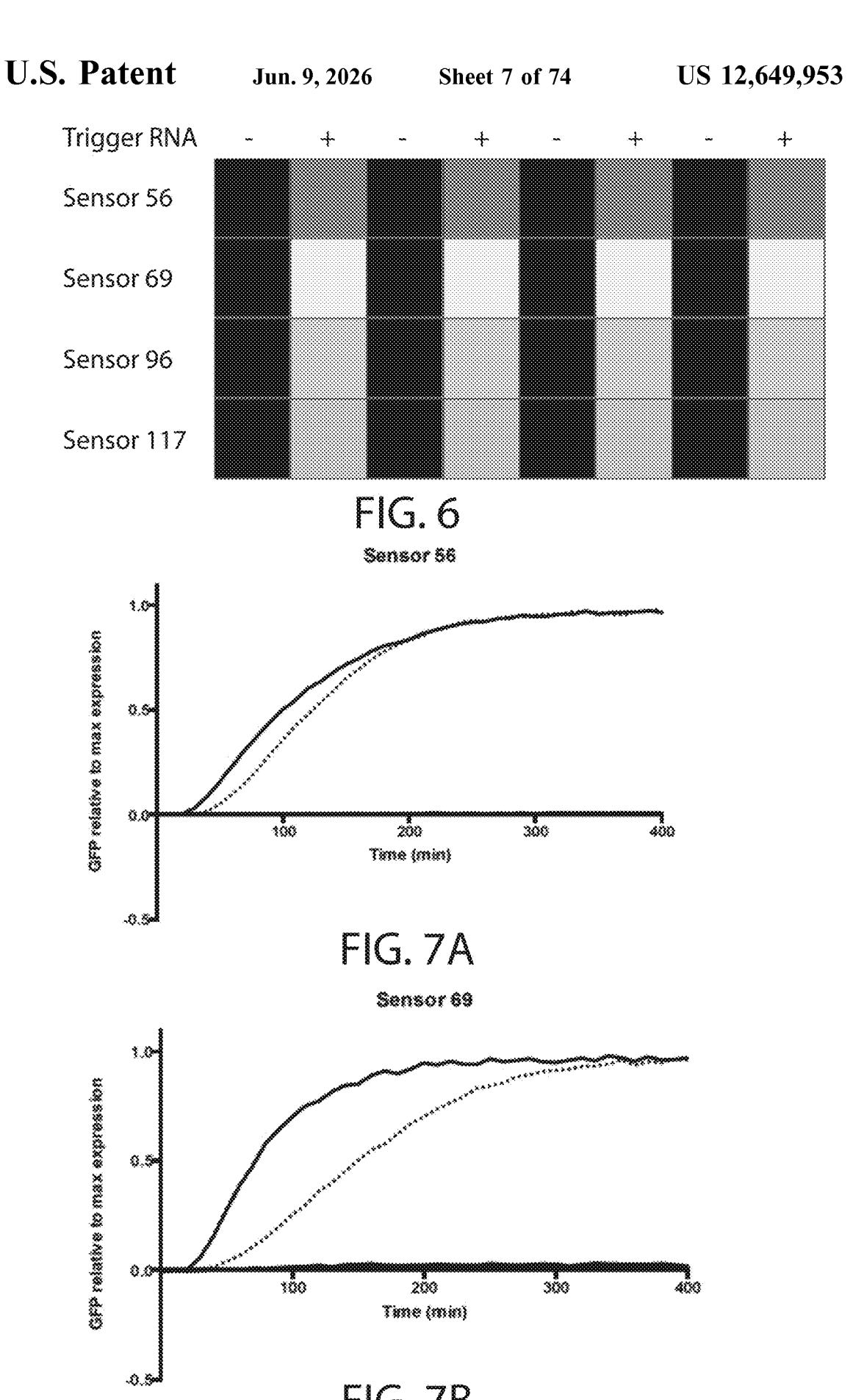
FIG. 6 is a graphic representation of how 4 fluorescent reporters could be deposited onto a larger sheet of paper, using hydrophobic barriers printed using a wax-based laser printer or other method of printing or lithography to separate the reactions spaces. Protein expression from four toe-hold switches (56, 69, 96, 117) could be alternately activated or not using trigger RNA.
FIGS. 7A-7H are time course data of GFP expression from eight Toe-hold switches: 56 (FIG. 7A), 69 (FIG. 7B), 96 (FIG. 7C), 117 (FIG. 7D), PA (FIG. 7E), PB (FIG. 7F), PC (FIG. 7G), PD (FIG. 7H) using freeze dried T7-based cell-free reactions (7 ul volume, no paper). Time course data show that translation-only reactions (from RNA; solid lines) are induced more quickly than transcription-translation reactions (from DNA; dotted lines). The time savings comes from pre-transcribing the RNA riboswitch, so that in the presence of trigger RNA translation occurs immediately. RNA copies of the riboswitch are less stable than DNA copies in the freeze-dried systems.

The time required to generate gene circuit outputs is another important factor. Results reported to this point have been generated from DNA-based circuits, either plasmid or linear dsDNA. However, with ssRNA-based toe-hold switches, reaction rates can be shortened by using gene circuits pre-transcribed to linear RNA. For these translation-only reactions, time to the earliest detected output can be reduced from 35 to 25 minutes in solution (FIGS. 7A-711). Conversely, running transcription-only sensors that use fluorescent Spinach RNA aptamer (Paige et al., Science 2011, 333, 642-646) as an output, the time to detection can be similarly shortened.

The simplicity of design and the low cost of inputs means that these sensors can be easily produced at a cost between 25-60 cents, depending on the specific sensor. While commercially available cell-free systems were used in experiments described herein, the protocols for making these systems purpose-built are well established and would reduce the cost of sensors to as low as 4 cents.

Figure 7C:
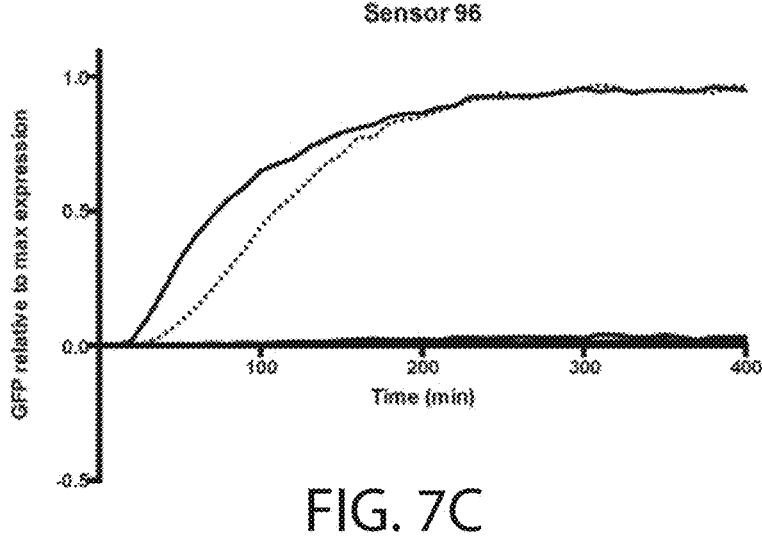
Figure 7D:
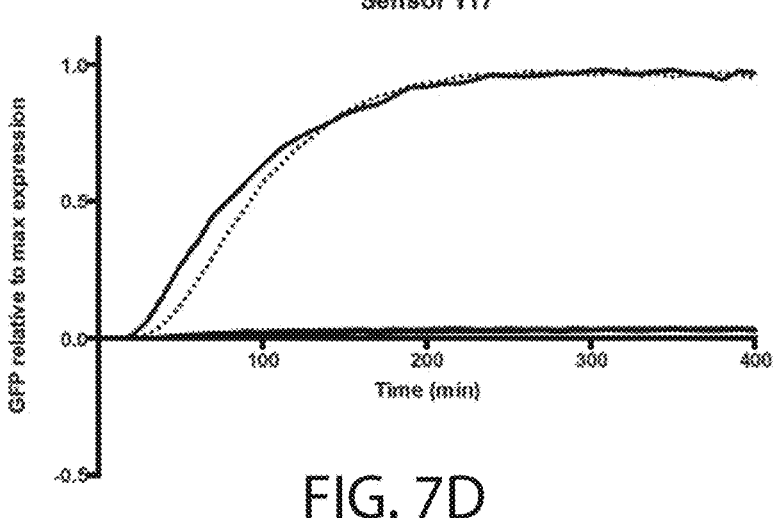
Figure 7E:
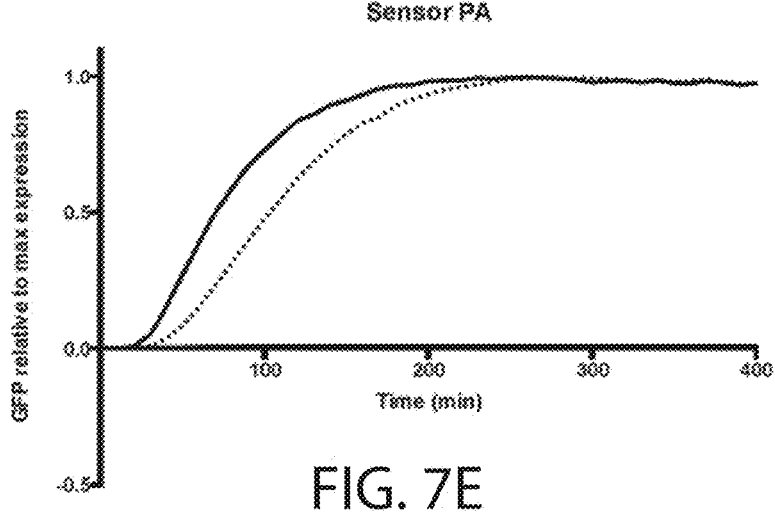
Figure 7F:
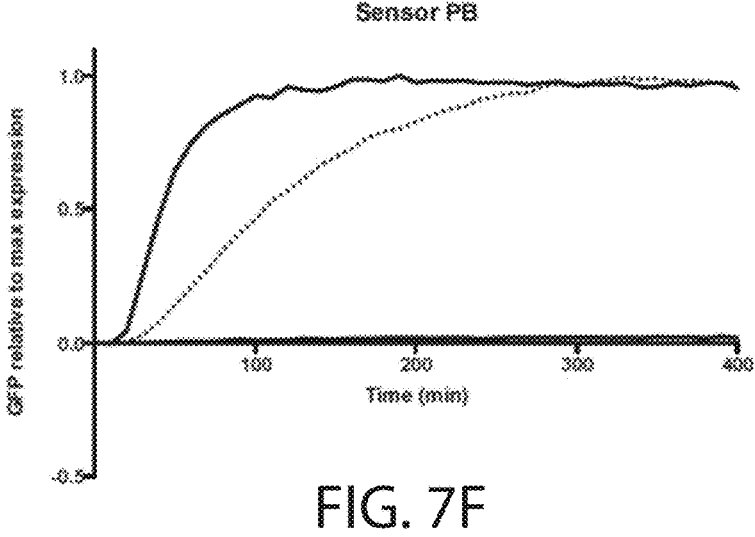
Figure 7G:
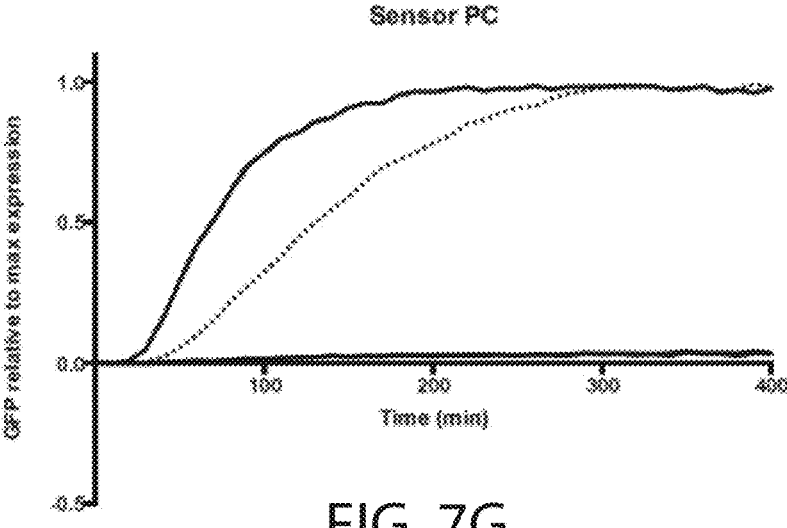
Figure 7H:
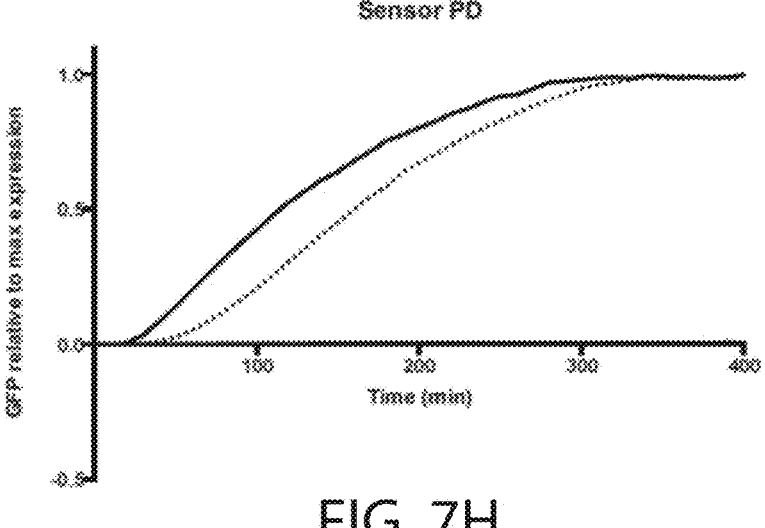

The lyophilized sensors can be designed to produce a colorimetric output visible to the naked eye. To do so, GFP was replaced with the enzyme beta-galactosidase or LacZ to produce a system that generates a dramatic color change in response to the presence of synthetic trigger RNA. In this reaction the expression of LacZ leads to the enzymatic cleavage of yellow chlorophenol Red-β-D-galactopyranoside substrate to magenta chlorophenol red. Moreover, as will be discussed shortly, the use of an enzyme-mediated reporter introduces an additional signal amplification step into the system. Using the PA toe-hold switch, the response time of the reaction can be seen to begin at the 25 minute time point in the time series that documents the reaction on paper (FIG. 7E). Similar results were observed for the whole family of toe-hold LacZ switches. An alternative colorimetric reporter enzyme, chitinase, has also been incorporated for cell extracts from cells that contain wild-type LacZ. As demonstrated with the tetO_chitinase switch, the presence of aTc inducer resulted in the expression of chitinase, which cleaves the colorless 4-Nitrophenyl N,N'-diacetyl-beta-D-chitobioside substrate to a yellow p-nitrophenol product (FIG. 9).

Figure 12A:
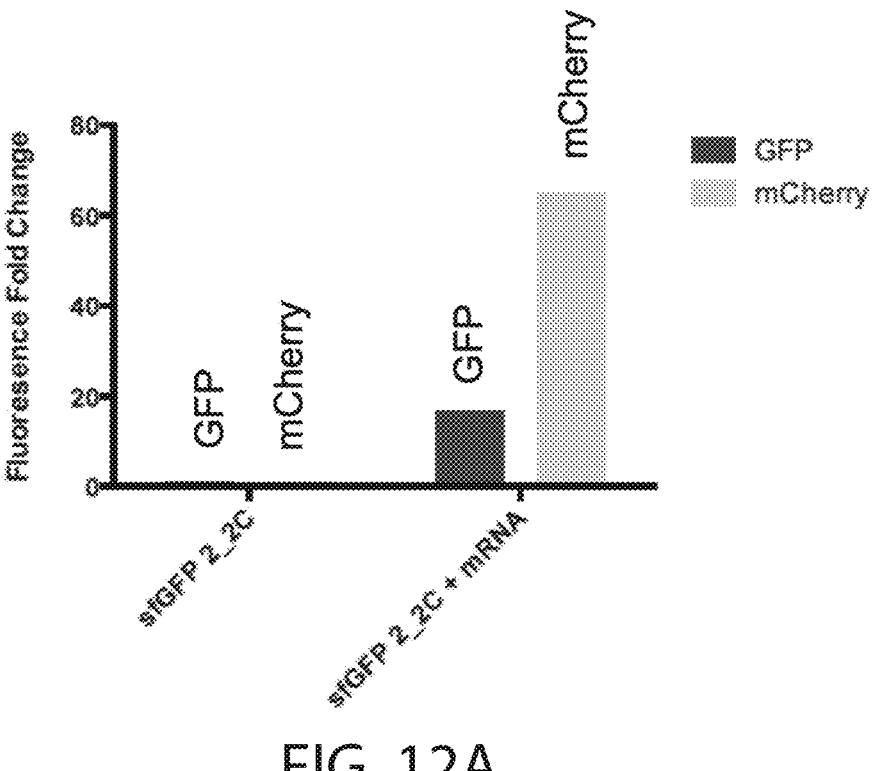
FIGS. 12A-12B show demonstrations of mRNA sensors.
Figure 12B:
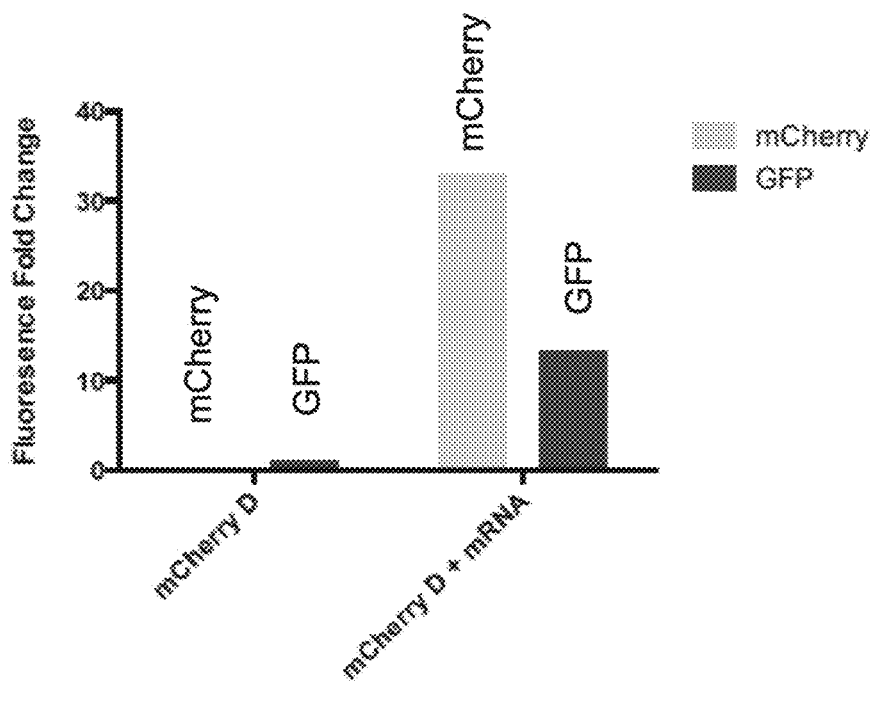
Figures 13A, 13B:
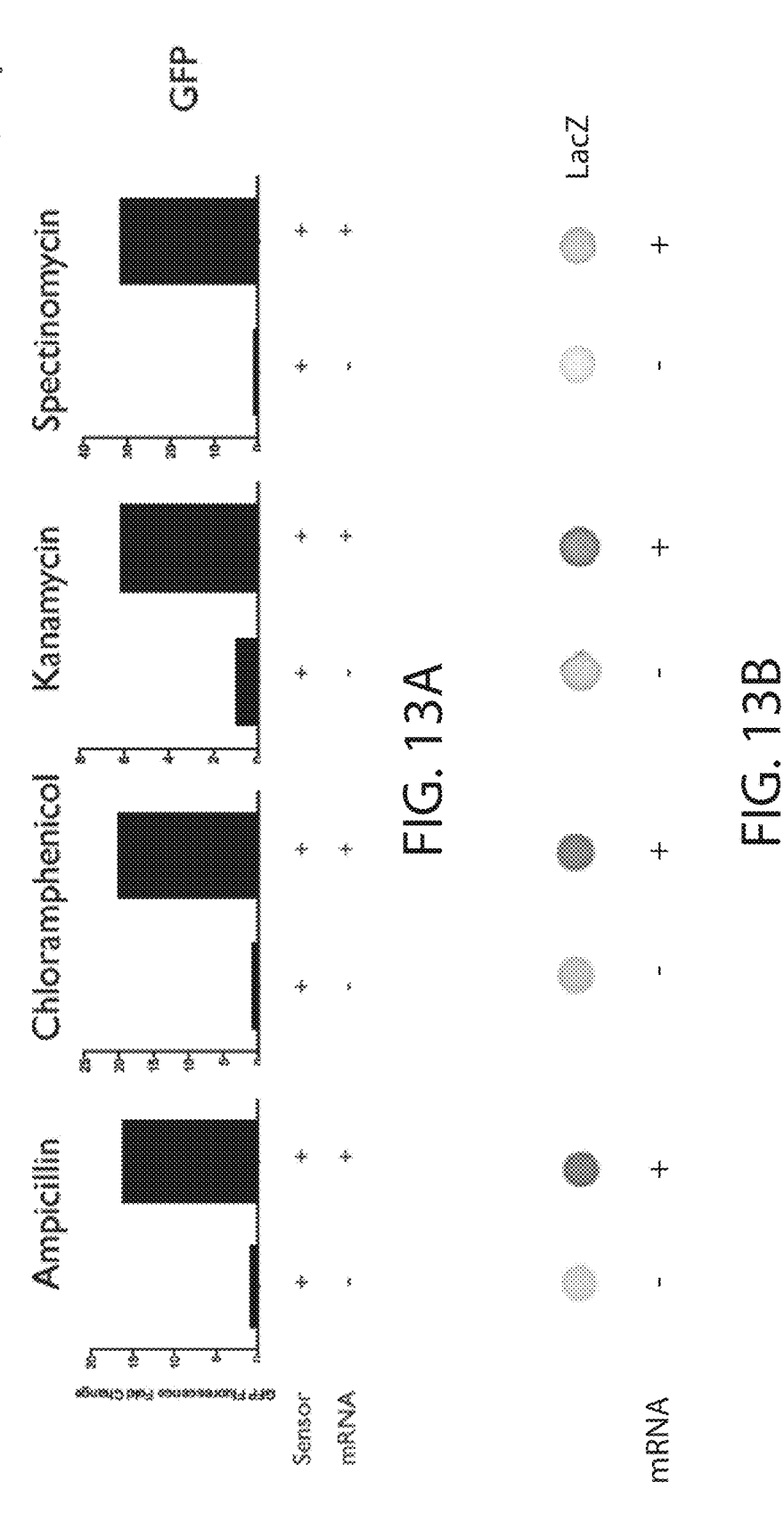
FIGS. 13A-13B show that mRNA sensors can be used for antibiotic resistance genes.
Figure 14A:
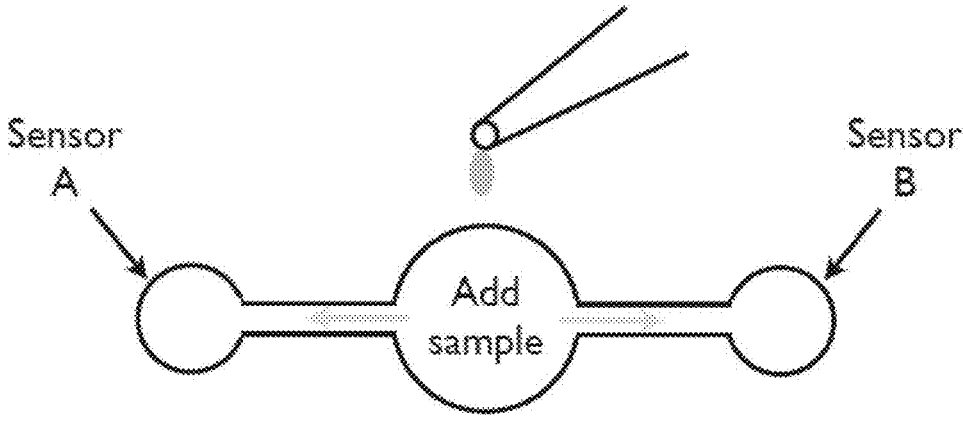
FIGS. 14A-14D show how microfluidics could be used to deliver sample to more than one sensor in a device, as well as to control evaporation.
Figure 14B:
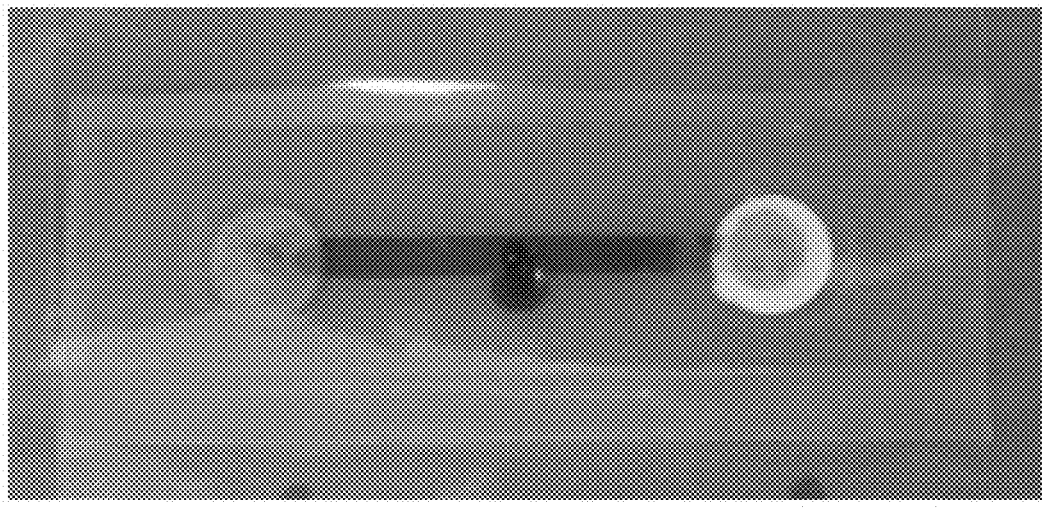
Figure 14C:
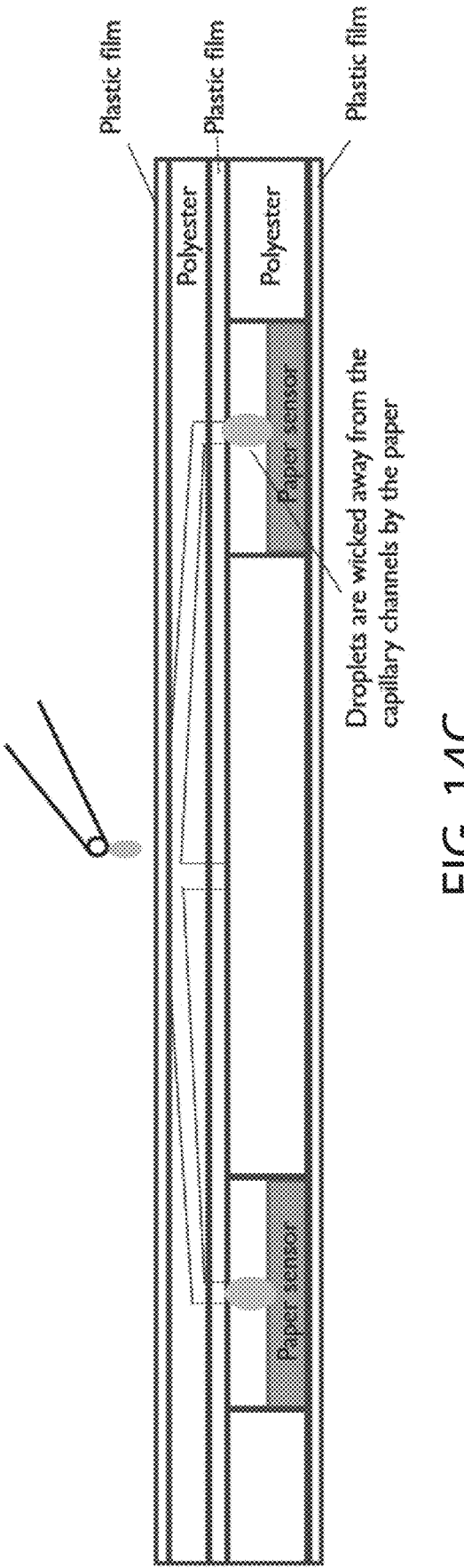
Figure 14D:
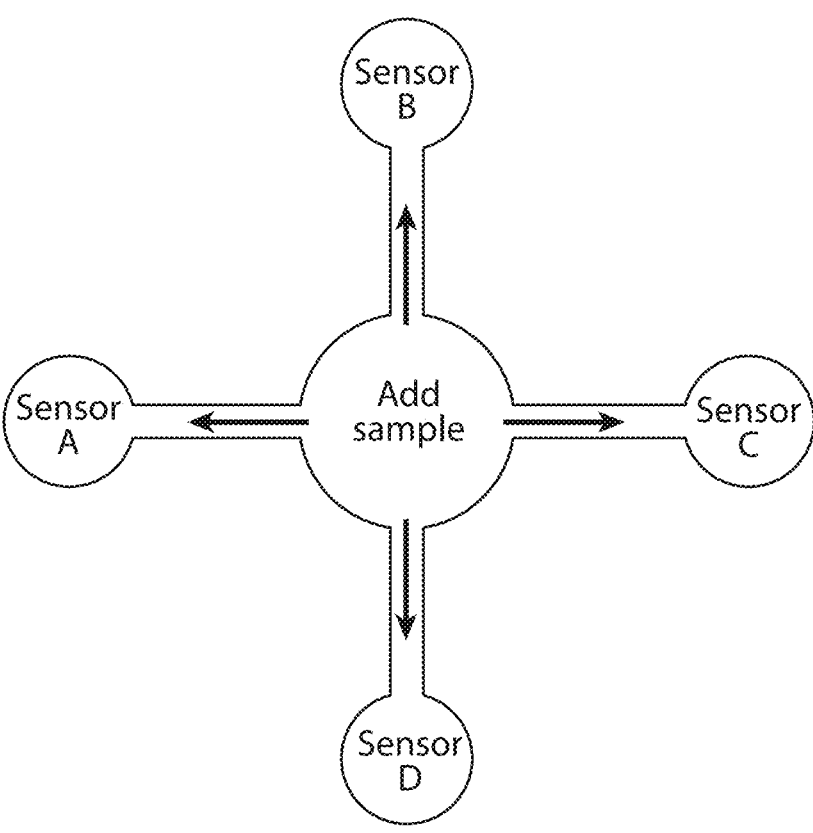
Figure 15:
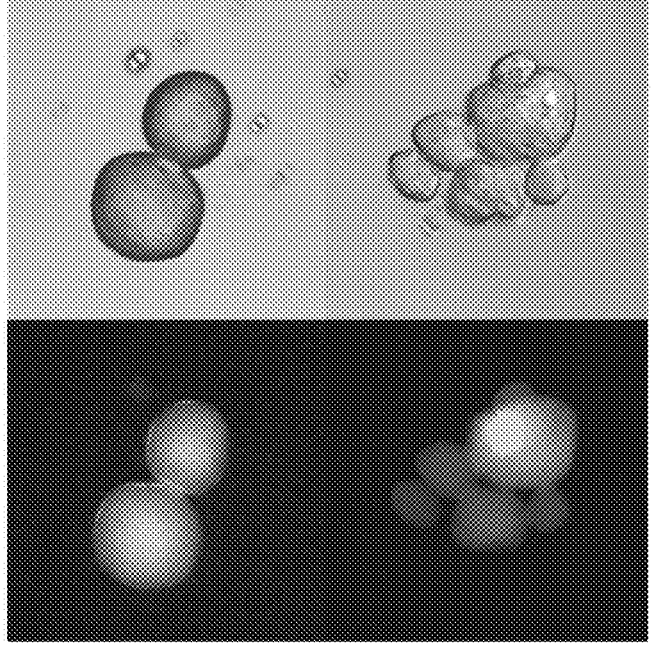
FIG. 15 shows chitin beads hydrated with a cell-free system containing DNA template for a Toe-hold RNA sensor and the complementary RNA trigger.

Lyophilized sensors can be designed to detect sequences within full-length active mRNA targets, a key feature for a diagnostics platform. The first goal was the detection of GFP and mCherry mRNA. Using an algorithm that predicts RNA secondary structure, sensors were built to target sequences likely to be accessible, and, when tested, yielded fluorescent induction in the presence of GFP (60-fold) and mCherry (14-fold) mRNAs, respectively (FIGS. 12A-12B). As a demonstration of the potential for paper-based synthetic gene networks as an in vitro diagnostics platform, mRNA sensors for antibiotic resistance genes were next developed. Using freeze dried cell-free reactions in solution, mRNA sensors for ampicillin (15-fold), kanamycin (6-fold), chloramphenicol (20-fold) and spectinomycin (32-fold) yielded significant GFP fold-change in the presence of their respective mRNAs (FIG. 13A). These sensors were modified to produce LacZ, which in the presence of mRNA from respective antibiotic resistance genes converted sensor output into the visible colorimetric mode (FIG. 13B).

Example 2: Paper-Based Synthetic Gene Networks

Bacterial and mammalian components can be freeze-dried onto paper, and other porous substrates, to create poised synthetic gene networks that are stable for long-term storage at room temperature and can be activated by rehydration. The resulting engineered materials have the transcription and translation properties of a cell and can host genetically encoded tools using, e.g., commercially available cell-free transcription and translation systems. The technology is demonstrated herein with small molecule and RNA actuation of genetic switches, the construction of paper-based sensors for glucose and mRNAs, including antibiotic resistance genes, and the characterization of novel gene circuits. For greater practical use, gene circuits can be enhanced with colorimetric outputs for detection by the naked eye, as well as with the fabrication of a low cost, electronic optical interface for quantification and possible automation of reactions. These low cost, paper-based synthetic gene networks have the potential to bring bio-based sensors, counters, timers and simple logic to portable devices.

Results

Figure 16A:
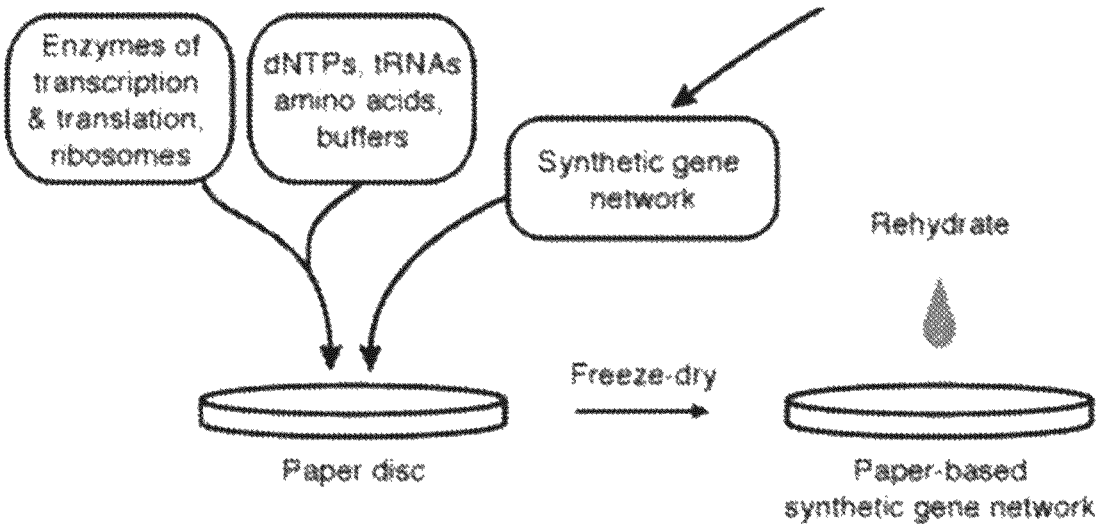
FIG. 16A is a schematic of paper-based synthetic gene networks. Enzymes necessary for transcription, translation, or both are combined with engineered gene circuits, and then embedded and freeze dried into paper to create stable and portable synthetic gene networks outside of the cell context. These networks can include, for example, genetically encoded tools with trigger, regulatory transducer and output elements.
Figure 16A:
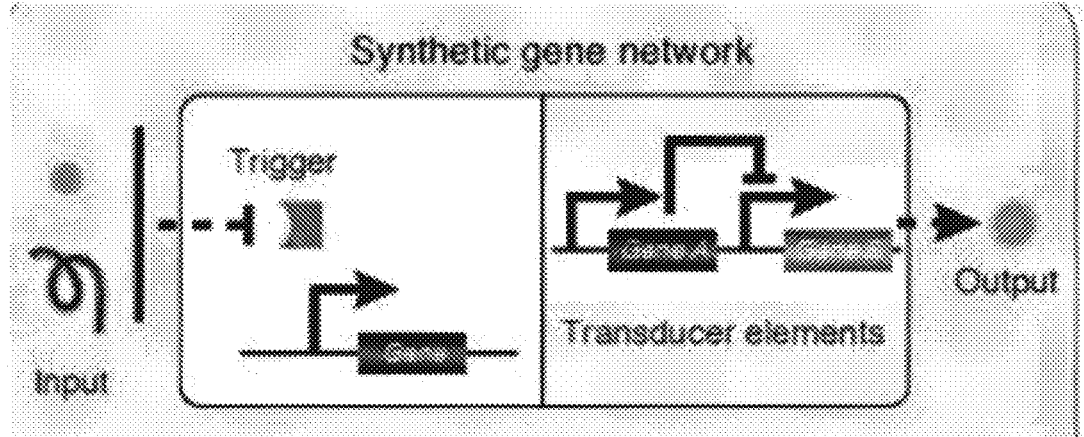
Figure 16B:
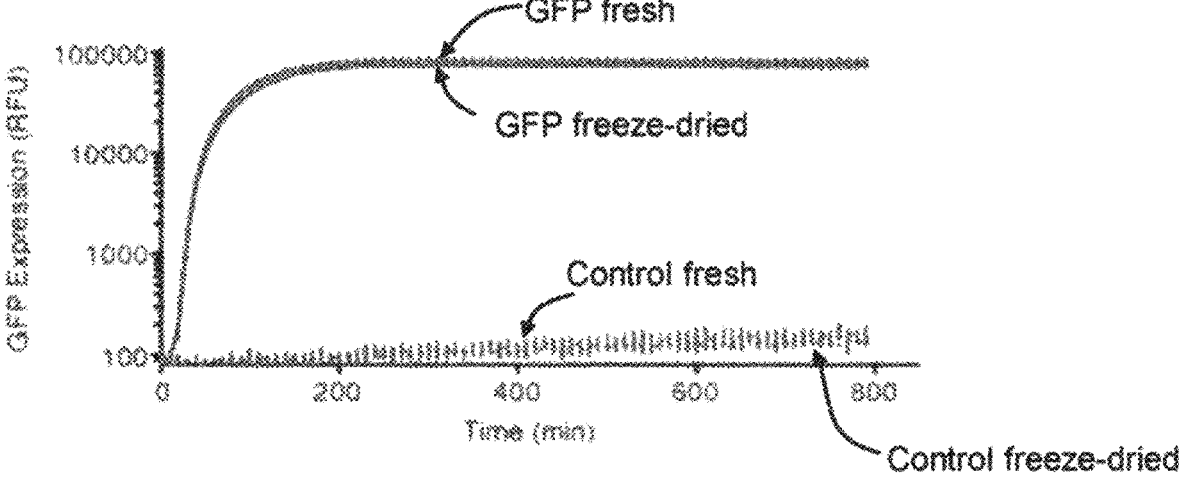
FIG. 16B is a plot showing GFP expression in solution phase from fresh and freeze-dried PT7 cell-free reactions.
Figure 16C:
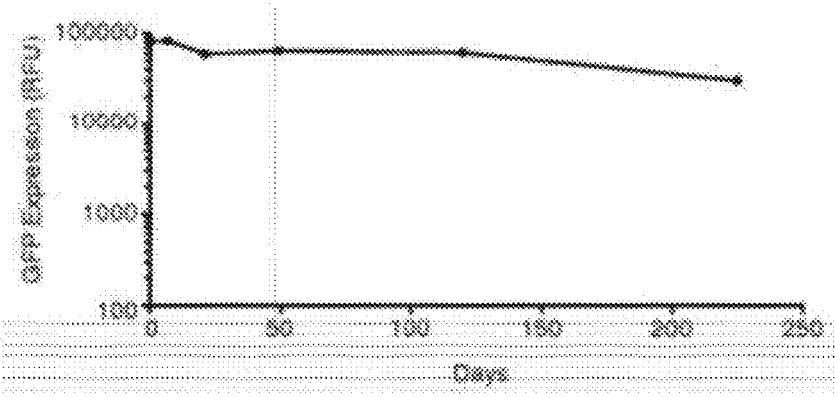
FIG. 16C is a plot showing that freeze dried pellets of the PT7 cell-free expression system are stable for months, yielding GFP expression when rehydrated.
Figures 20A, 20B:
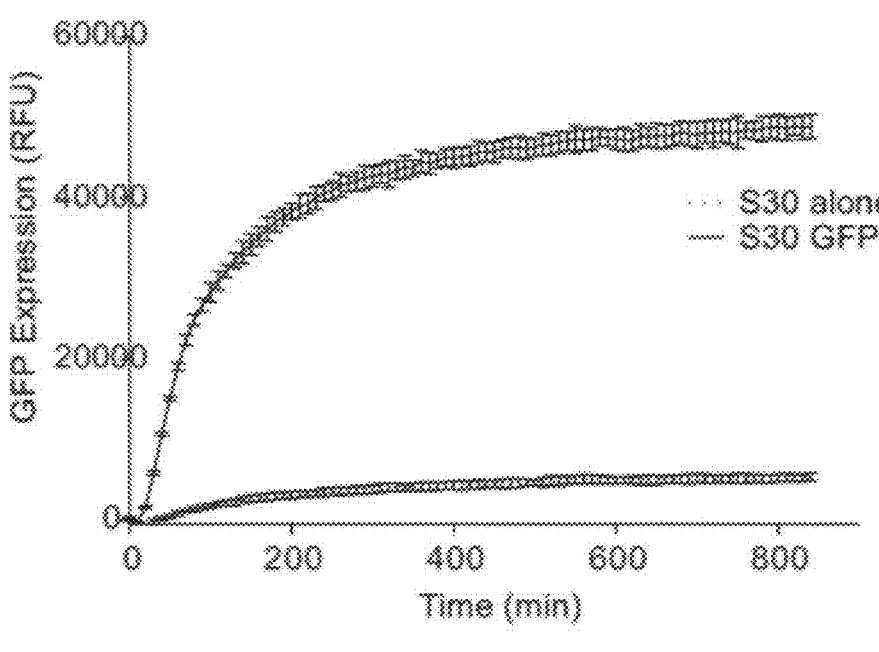
FIGS. 20A-20B are plots showing solution phase reactions from freeze dried pellets.
Figure 21A:
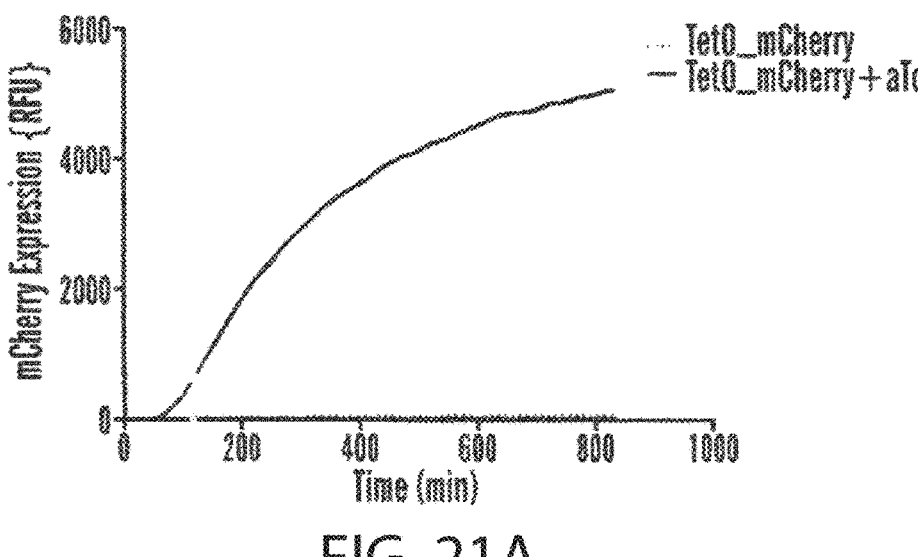
FIGS. 21A-21F show TetO regulated paper-based expression of mCherry and GFP over time.
Figure 21B:
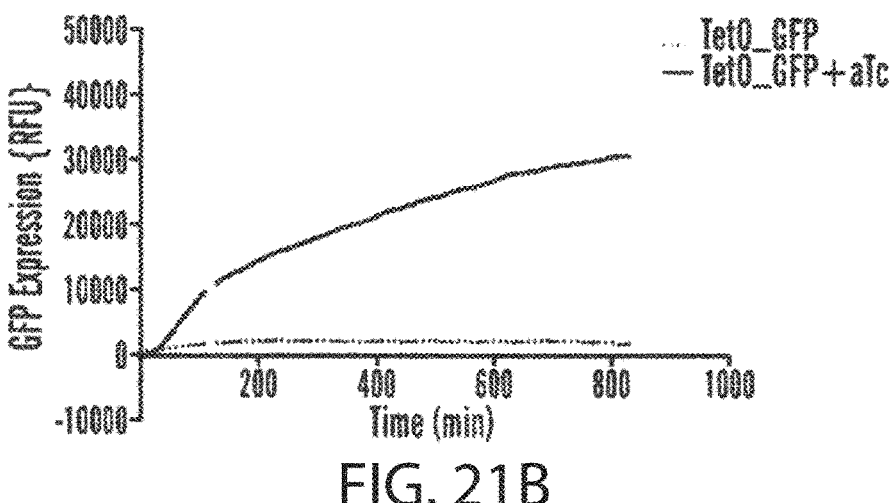
Figure 21C:
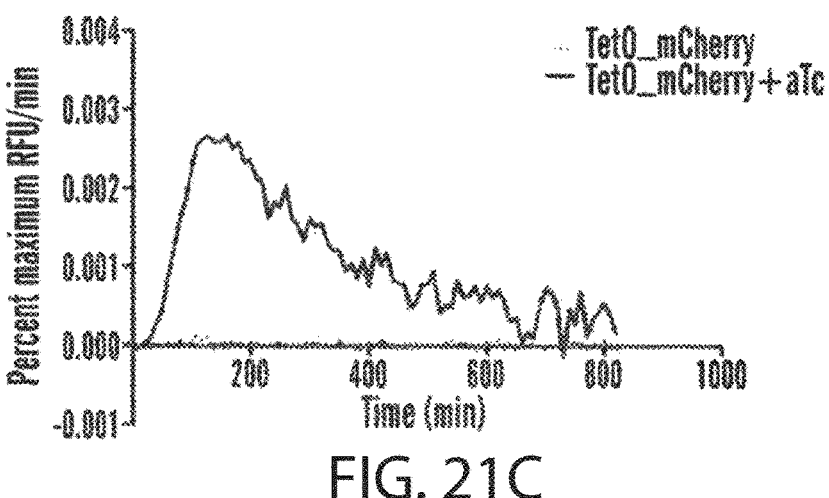
Figure 21D:
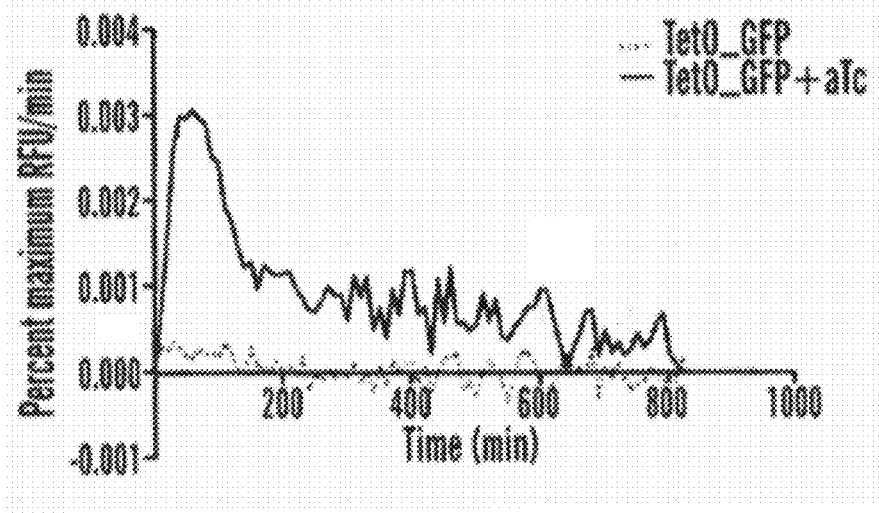
Figure 21E:
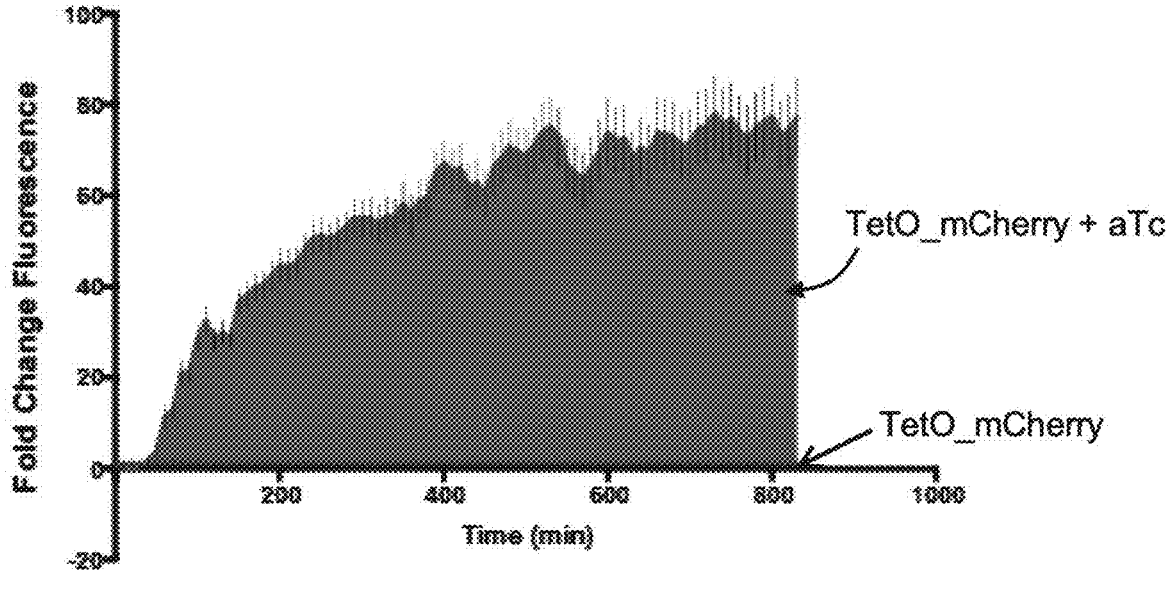
Figure 21F:
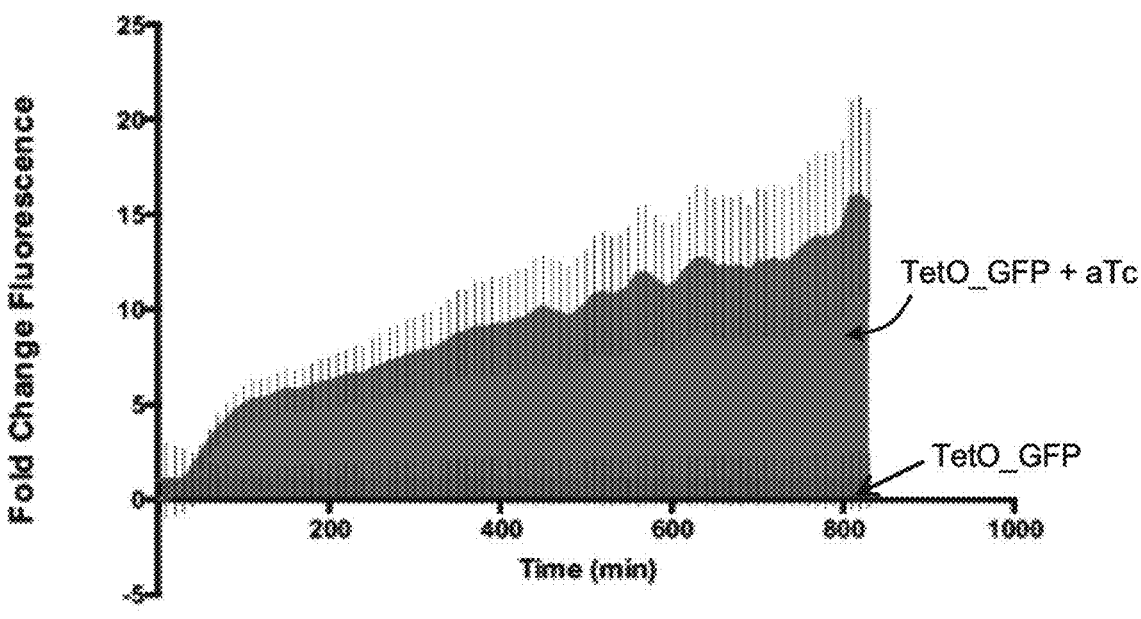

Tests were performed to determine if the enzyme activity required for transcription and translation could be reconstituted from freeze-dried cell-free expression systems, which normally require storage at −80° C. Remarkably, GFP expression comparable to fresh from frozen reactions was supported by the rehydration of a freeze-dried, commercially available expression system (PT7) assembled from ribosomes and 35 recombinantly expressed and purified bacterial proteins (FIG. 16B; Shimizu Y, et al. Nat Biotechnol. 2001 August; 19(8):751-5; Shimizu Y, Ueda T., Methods Mol Biol. 2010; 607:11-21). This approach was then extended to systems with greater molecular complexity based on whole cell extracts. Using expression constructs dependent on either *E. coli* RNA polymerase (S30) or T7 (S30 T7) RNA polymerase (RNAP), constitutive expression of GFP was supported in small, solution phase reactions started from freeze-dried pellets (FIGS. 20A-20B). Importantly, using the PT7 system as a model, these freeze-dried cell-free systems are stable over time, with transcription and translation activity remaining high after months of room temperature storage (FIG. 16C).

While freeze-dried preparations offer great potential for the storage of poised synthetic biology tools, the handling of solution phase reactions is awkward for applications outside of the lab. To address this, the cell-free systems and synthetic gene networks were embedded onto paper and other porous materials (FIG. 16A). Paper provides a high capillary matrix for small volume molecular and biochemical reactions. To begin, tests were performed to determine whether simple cell-free expression could be supported while embedded in the cellulose matrix of paper.

Figure 16D:
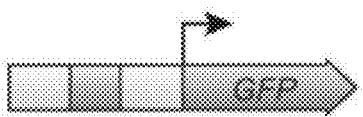
FIG. 16D is a schematic of the constitutive GFP expression constructs used on paper.
Figure 16E:
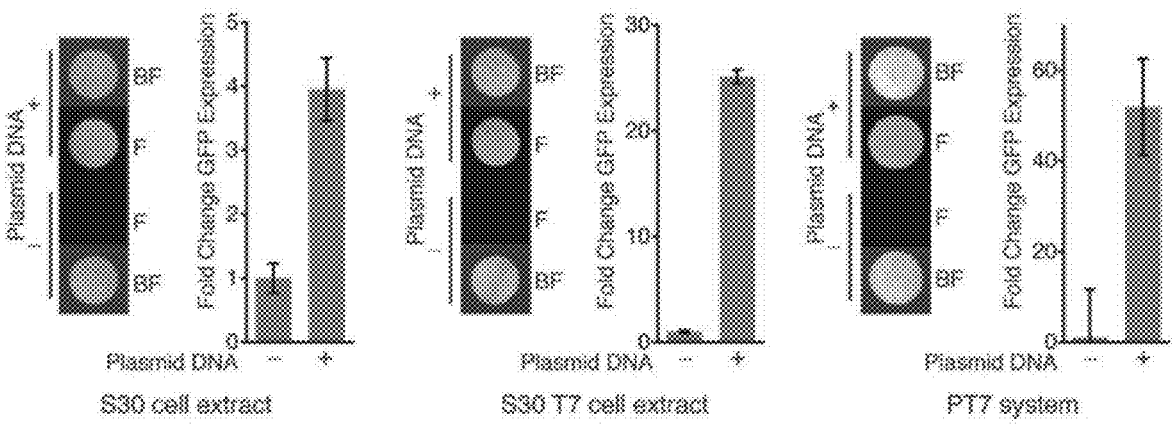
FIG. 16E is a set of images and fold change measurement of constitutive paper-based GFP expression from freeze-dried S30, S30 T7 and PT7 cell-free systems during the first 90 minutes of incubation.

Small 2 mm filter paper discs were freeze-dried with bacterial cell-free systems (1.8 μL) containing either *E. coli* (S30) or T7 RNAPs (S30 T7, PT7) and a corresponding GFP expression plasmid (FIG. 16D). Upon rehydration and incubation at 37° C., these paper-based reactions yielded consistent GFP fluorescence under the regulation of either RNAP. Fluorescence imaging of the paper discs confirm GFP expression, and reaction dynamics were monitored by placing the paper discs at the bottom of black, clear bottom 384 well plates for incubation in a 37° C. plate reader (FIG. 16E).

Figure 16F:
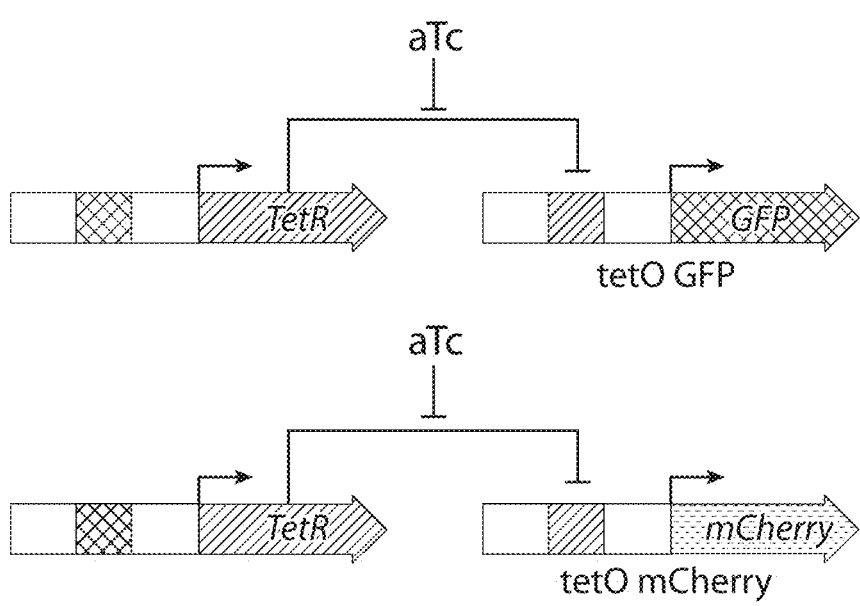
FIG. 16F is a schematic of the TetO regulation of GFP or mCherry.

Next inducible expression systems were tested to determine if more complex synthetic gene networks could be supported by the freeze-dried, paper-based reactions (FIG. 16A). TetO regulated expression, a classic synthetic biology switch, was used. Regulation of this system is mediated by the tet repressor (tetR), that binds to the TetO promoter, preventing transcription (FIG. 16F, Lutz R, Bujard H., Nucleic Acids Res. 1997, 25:1203-10). Such regulation performed in vitro required that constitutive tetR expression also be encoded into the synthetic gene network. Expression is then induced by addition of the antibiotic doxycycline or chemical analogs (aTc), which disrupts tetR binding to the promoter, allowing transcription of the regulated gene.

Freeze-dried discs were prepared with a cell-free system containing S30 *E. coli* cell extract, pre-translated tetR, and the network elements encoding the constitutive expression of tetR and TetO regulated GFP or mCherry. Varying only the presence of aTc, discs were rehydrated and incubated at 37° C. for 2 hours. The aTc-induced discs yielded expression of GFP and mCherry at 5 and 32-fold, respectively (FIG.

Figure 22A:
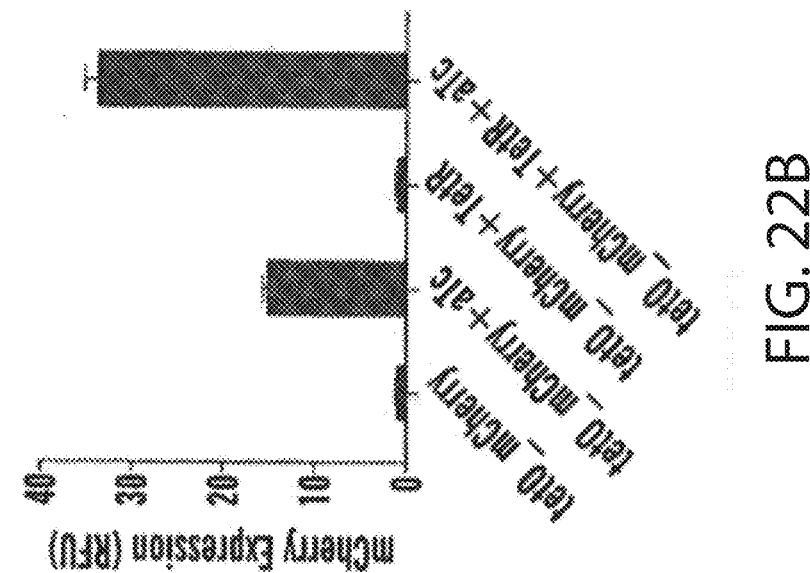
FIGS. 22A-22B show tetR supplementation of S30 extracts for TetO regulation improves fold change measurements. Error bars represent standard deviation. RFU, relative fluorescence.
Figure 22B:
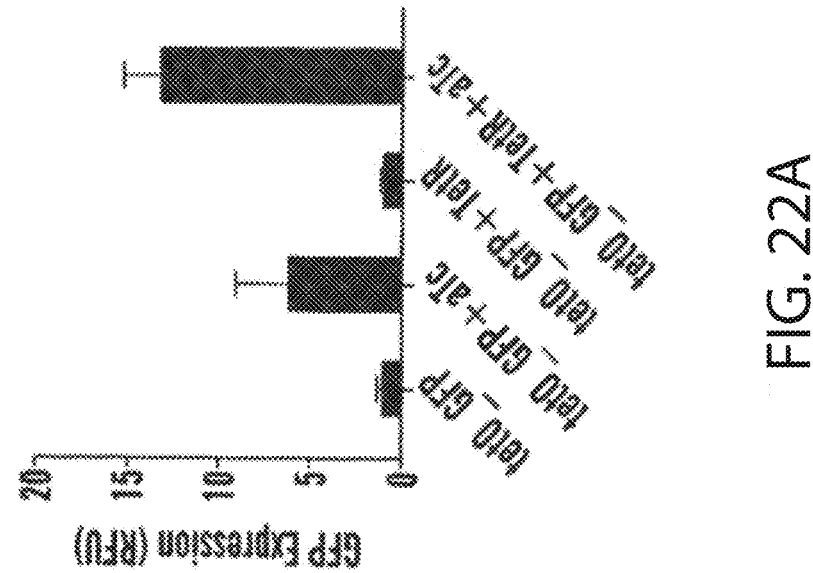

16G; FIG. 21). To optimize performance, it was found that regulatory control from the TetO promoter could be tightened if cell extracts were supplemented, prior to freeze drying, with tetR to control promoter leakage prior to the expression of the encoded tetR (FIG. 22). This successful tetR augmentation of cell-free systems prior to freeze drying suggests protein doping can be a useful way to tailor and enhance the regulatory and enzymatic environment of cell-free applications.

An important trend for synthetic biology is the use of RNA-actuated gene circuits (Callura, J. M., et al., Proc Natl Acad Sci USA 2012, 109, 5850-5855). Unlike circuits based on small molecule-based regulation, which are limited by the number of available unique recognition domains, RNA-based switches can be rationally programmed to recognize sequence-specific triggers and accordingly have the potential to offer essentially unlimited signaling space (Callura, J. M., et al., Proc Natl Acad Sci USA 2010,107, 15898-15903; Isaacs, F. J., et al., Nat Biotechnol 2004, 22, 841-847; Lucks, J. B., et al., roc Natl Acad Sci USA 2011, 108, 8617-8622). Here a new generation of riboregulators was tested, called toehold switches (Green et al., Cell 2014, 159, 1-15). These robust biomolecular switches provide tight, almost complete, translational regulation over transcripts, and exhibit excellent orthogonality. Moreover, by controlling the expression of alternative RNA polymerases (e.g., T3 RNAP), toehold switches can also trigger the synthesis of additional switch RNAs, permitting cascades and more sophisticated synthetic circuits.

Toehold construction. Toehold switch plasmids were constructed using conventional molecular biology techniques. Synthetic DNA templates (Integrated DNA Technologies, Inc.) were amplified using PCR, inserted into plasmids using Gibson assembly (Gibson et al., Nat. Methods 2009, 6, 343-345) with 30-bp overlap regions, and then successfully constructed plasmids identified using DNA sequencing. All plasmids were derived from pET system parent plasmids (EMD Millipore) and constitutively express lacI and antibiotic resistance genes. Additional descriptions of the toehold switch plasmids and their sequences are provided in Green et al. (Green et al., Cell 2014, 159, 1-15).

Figure 17A:
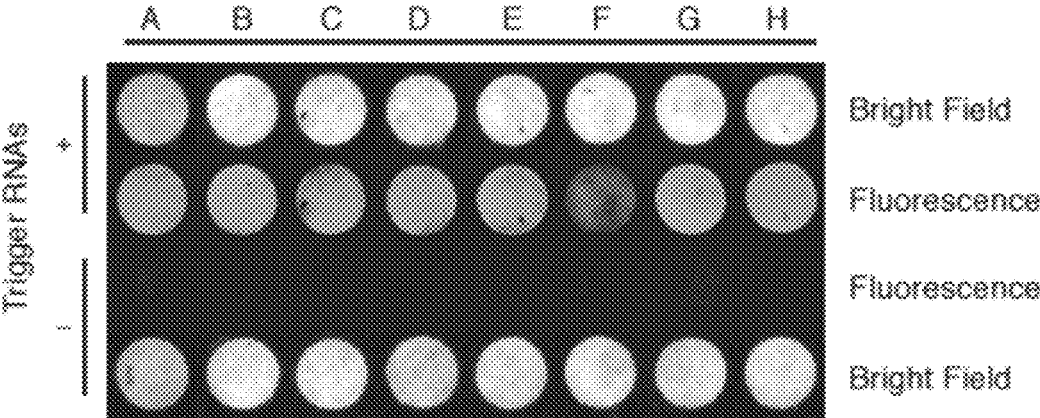
FIGS. 17A-17C demonstrate freeze-dried, RNA-actuated, gene circuits on paper.

The regulation of GFP expression under the control of eight different toehold switches was demonstrated on paper substrate. Experiments were performed by freeze-drying the recombinant PT7 expression system onto paper discs, along with linear DNA encoding specific switch RNAs. Twenty-four hours after drying, the paper discs were rehydrated with or without the complementary RNA trigger and incubated at 37° C. in a humid chamber for two hours. As expected, discs that received trigger RNA exhibited strong GFP expression, while control discs exhibited little if any expression (FIG. 17A).

Figure 17B:
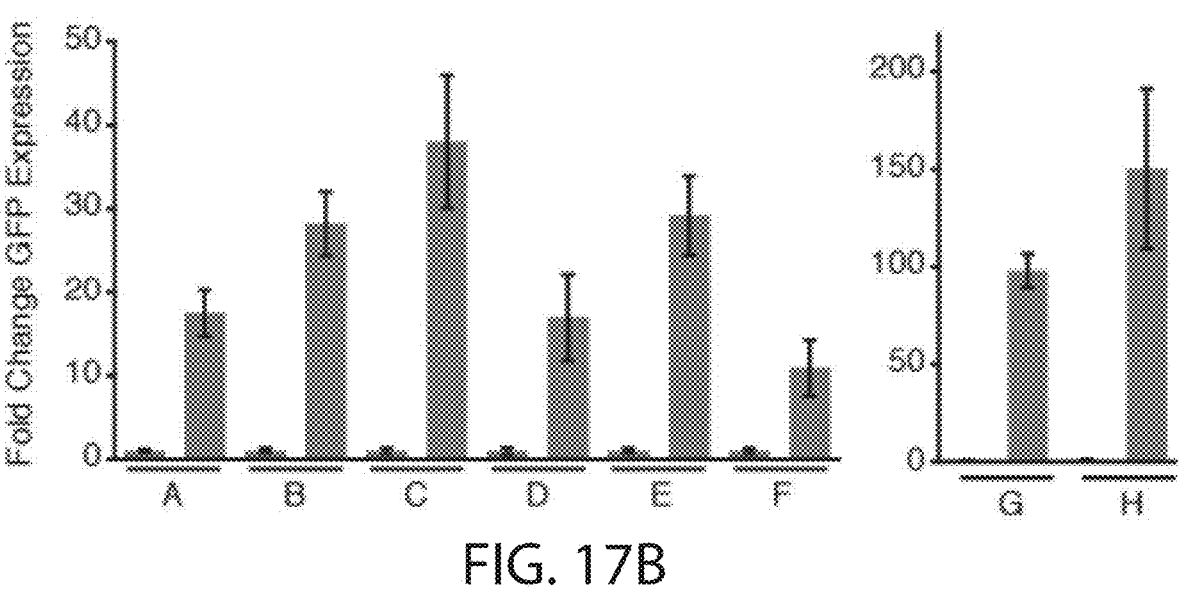
Figures 1, 23:
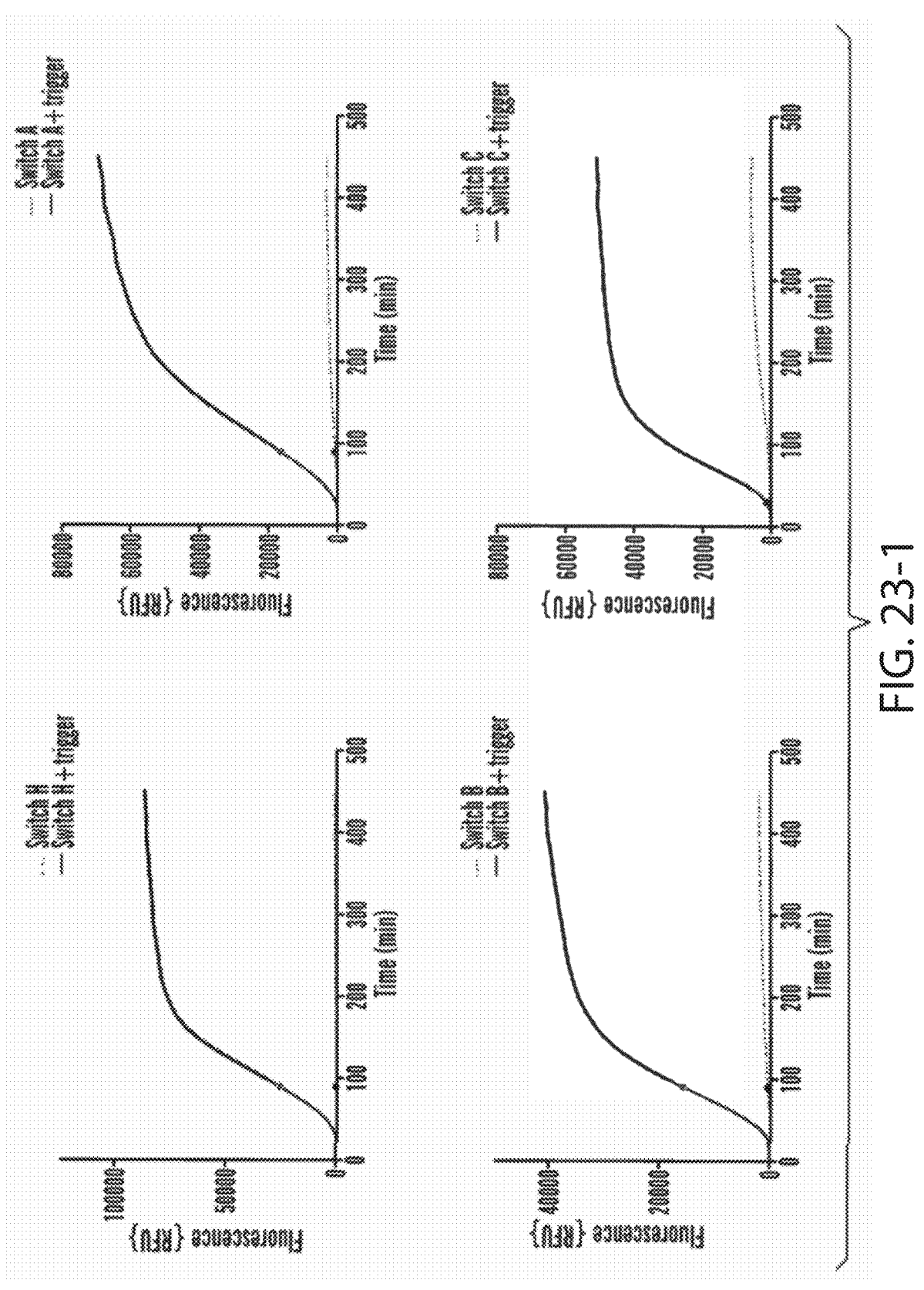
FIG. 23 is a set of plots showing paper-based regulation of GFP expression from toehold switches A-H. The red dots indicate the time point from which maximum fold change calculations reported in FIG. 17B were taken. RNA trigger concentration 5 um; RFU, relative fluorescence units. Values presented are the average of either triplicate or quadruplicate data. Error bars represent standard deviation.
Figures 2, 23:
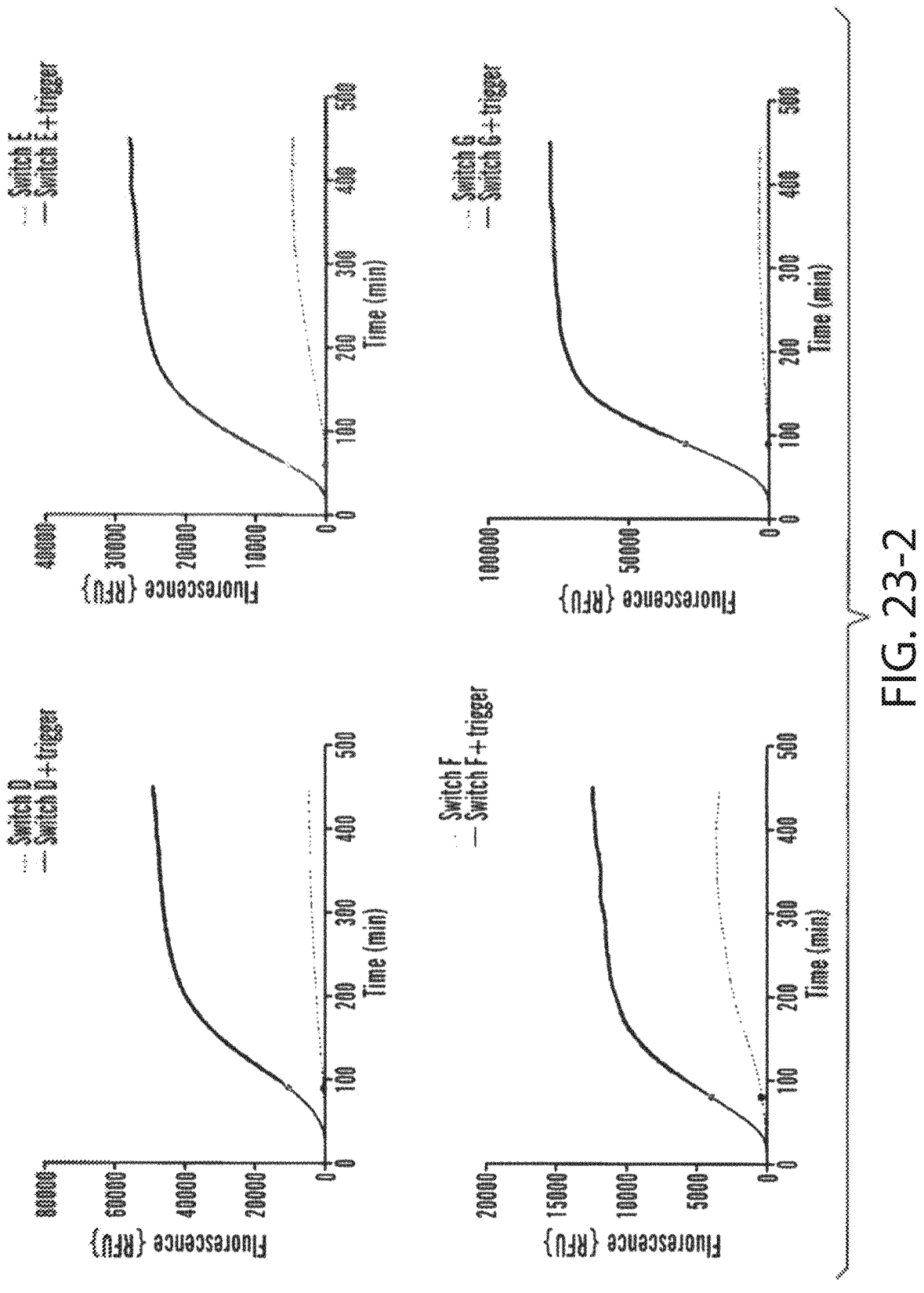
Figures 1, 24:
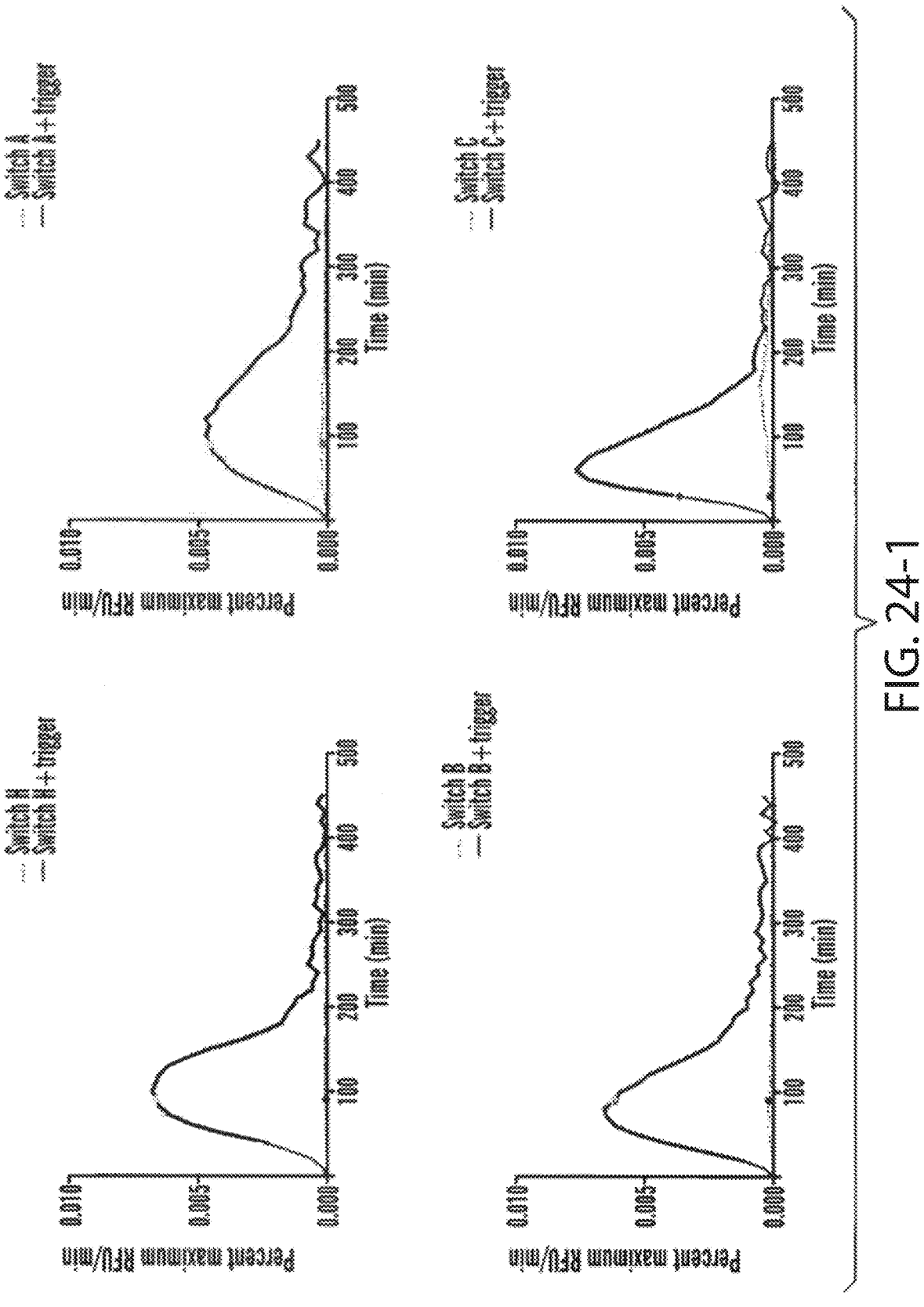
FIG. 24 is a set of plots showing rate of paper-based GFP expression from toehold switches A-H. The rate of fluorescence expression plotted as a portion of maximum fluorescence, where maximum=1. The red dots indicate the time point from which fold change calculations reported in FIG. 17B were taken. RNA trigger concentration 5 um. Values presented are the average of either triplicate or quadruplicate data. Error bars represent standard deviation.
Figures 2, 24:
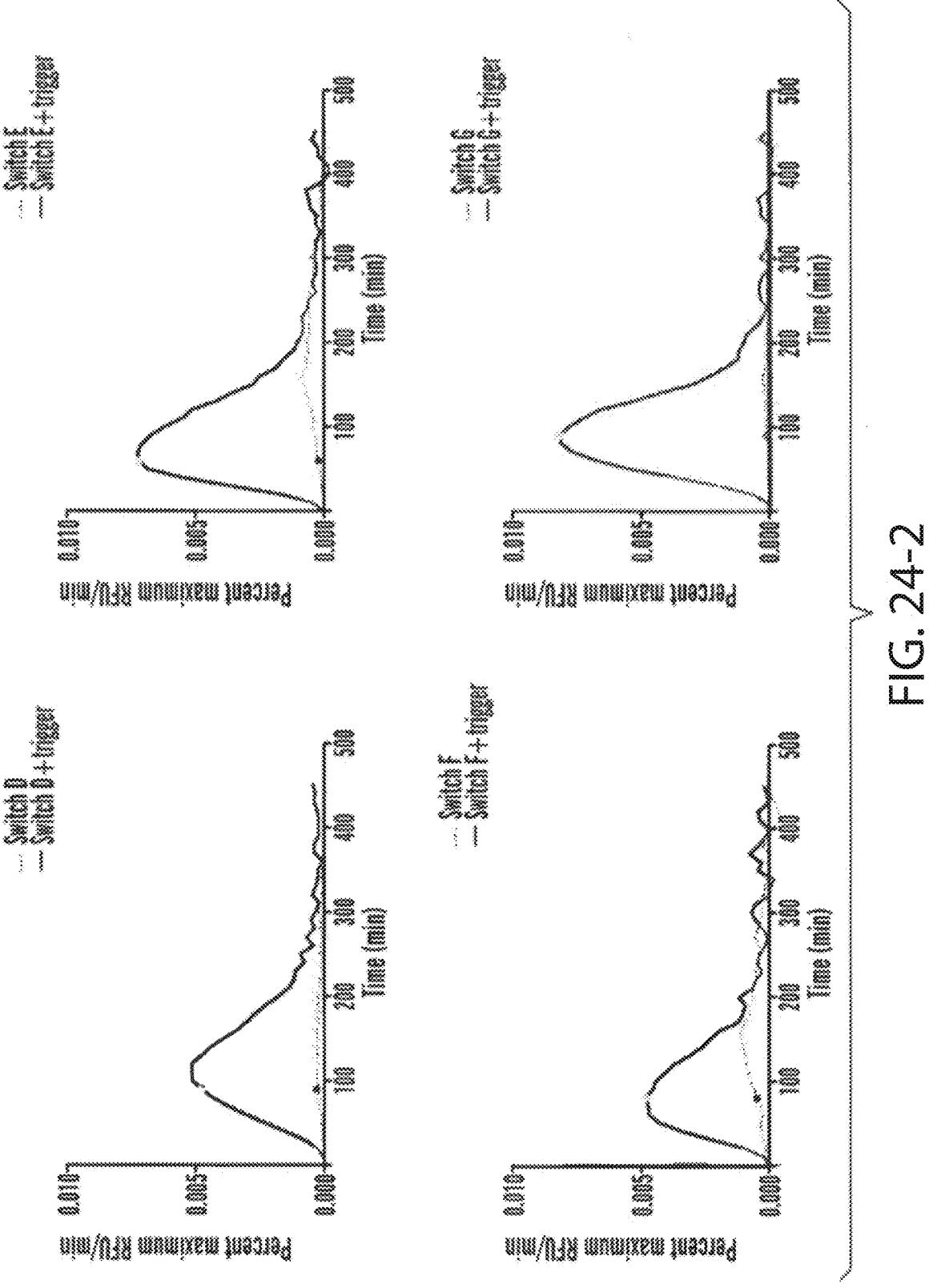
Figures 1, 25:
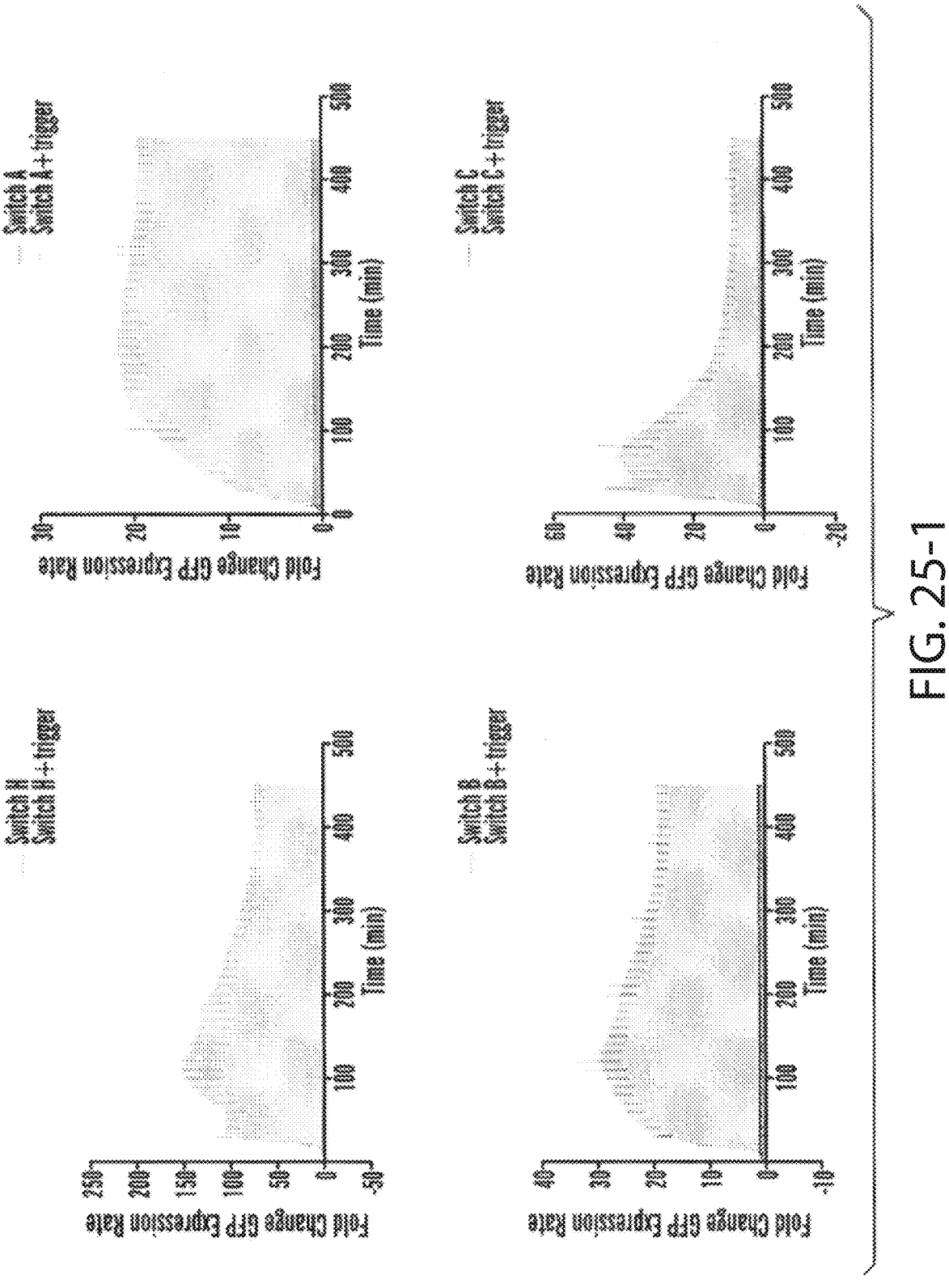
FIG. 25 is a set of plots showing fold change of fluorescence output from RNA induced toehold switches, relative to uninduced controls. Values presented are the average of either triplicate or quadruplicate data. Error bars represent standard deviation.
Figures 2, 25:
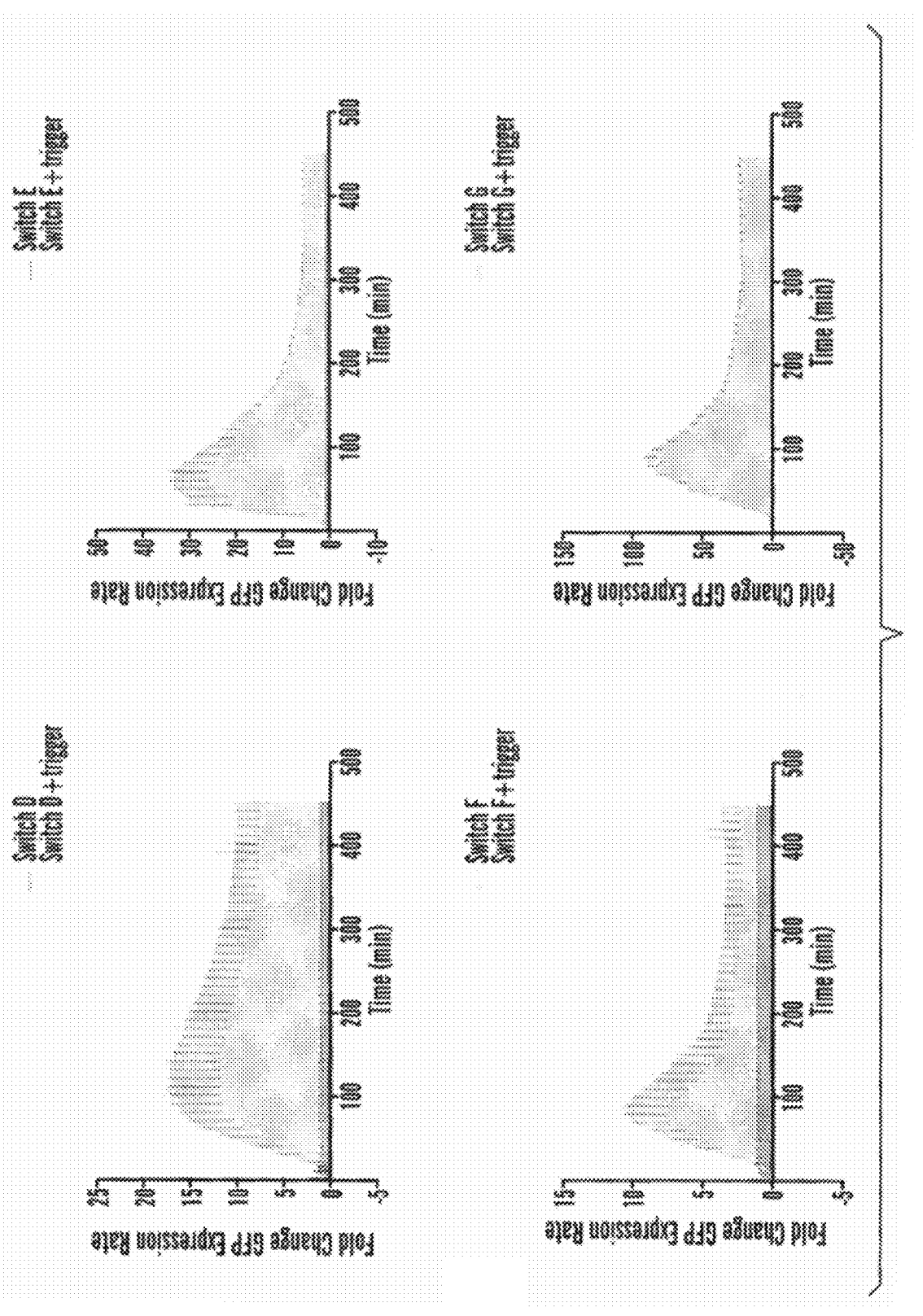
Figure 26:
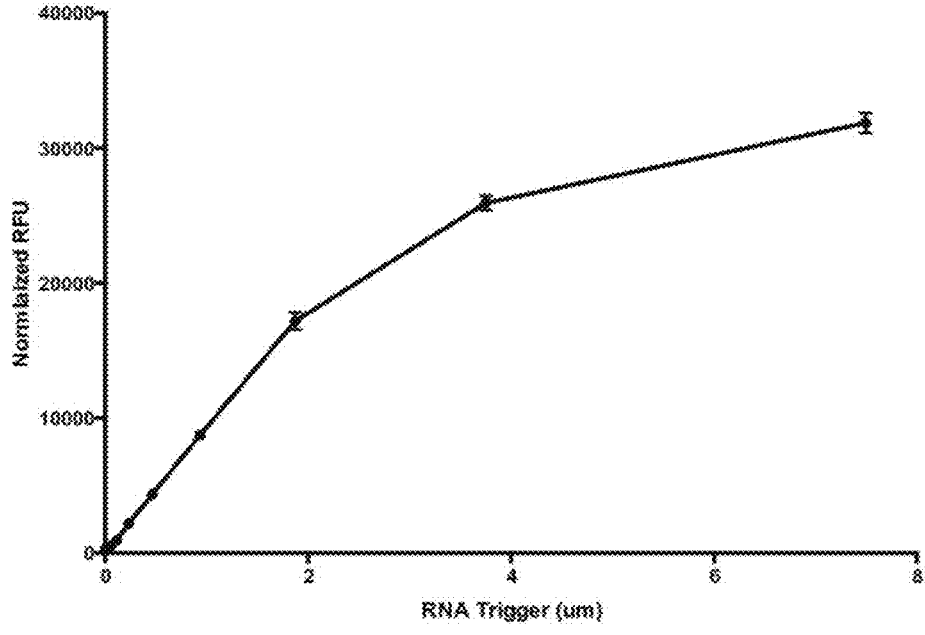
FIG. 26 is a plot showing titration of RNA trigger for toehold switch D in solution phase reactions. Values presented are the average of either triplicate or quadruplicate data. Error bars represent standard deviation.

Parallel experiments were done to measure reaction kinetics. Within 90 minutes of 37° C. incubation the maximum ON/OFF ratios ranged between 10 and 140-fold, with statistically significant signal detection in as little as 20 minutes (FIGS. 17B, 23, 25). Maximum expression rates occurred between 60 and 120 min, and the reaction output generally reached a plateau by 200 minutes (FIGS. 23, 24). Taking advantage of the nuclease-free nature of the PT7 recombinant system, RNA was titrated directly to reactions, and found a linear response to RNA concentration between low nanomolar and micromolar concentrations (FIG. 26). A concentration of 5 μM trigger RNA was chosen to maximize response in demonstration reactions. It is also of note, that switch behavior in freeze-dried lysates closely replicated that of toehold switches in vivo in *E. coli* (FIG. 27; Green et al., 2014). Importantly, the clear target-dependent induction of the toehold switches in the RNA-rich environment of *E. coli* helps to demonstrate sequence-specificity of these RNA components.

Figure 17C:
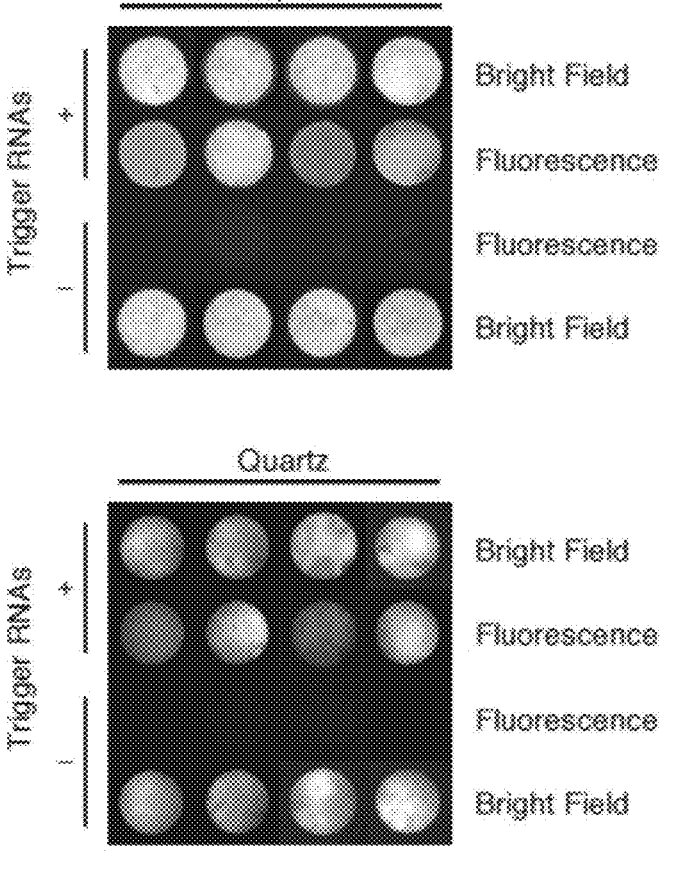
Figure 28A:
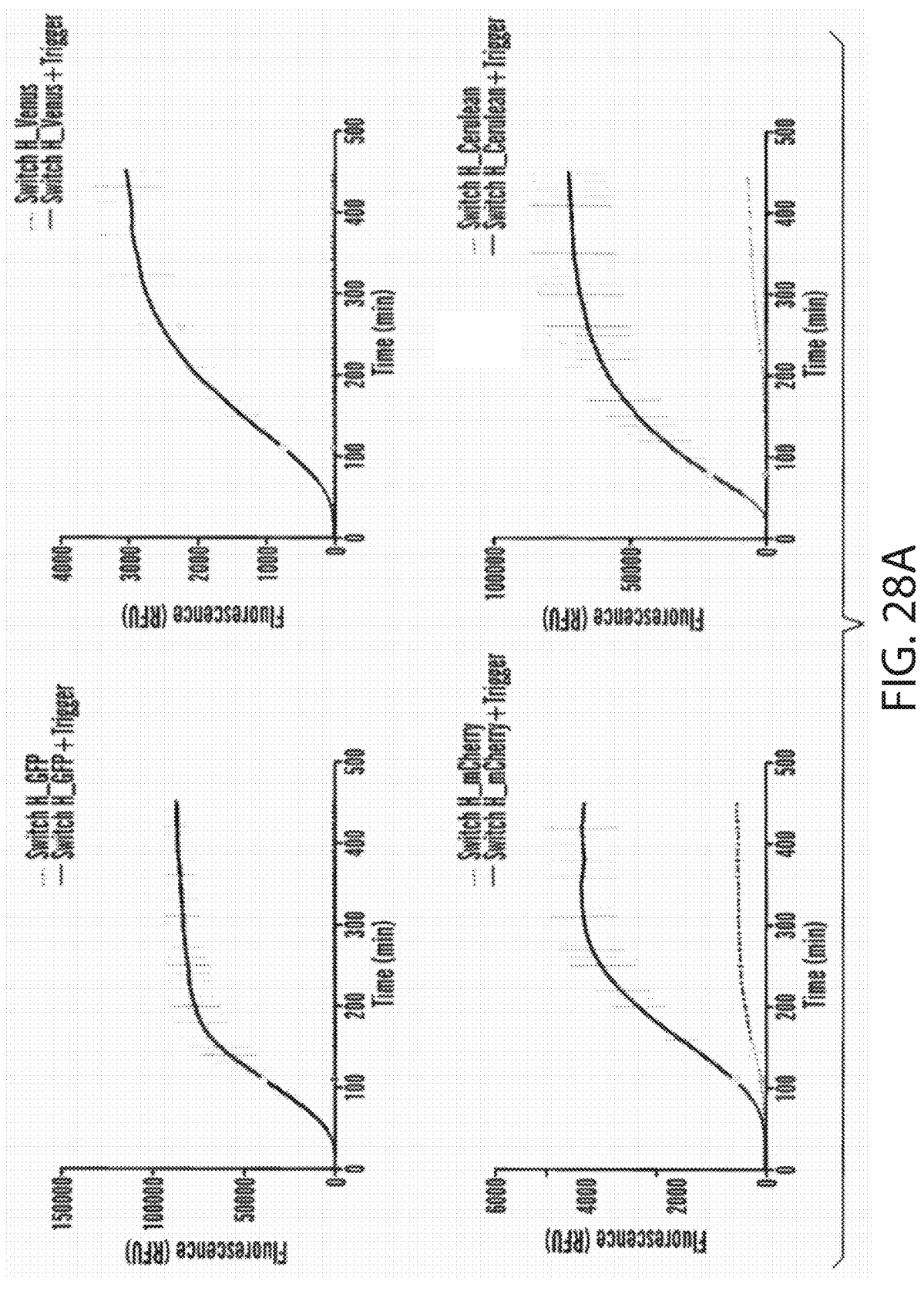
FIGS. 28A-28B show paper-based regulation of four fluorescence reporter proteins from toehold switch H.
Figure 28B:
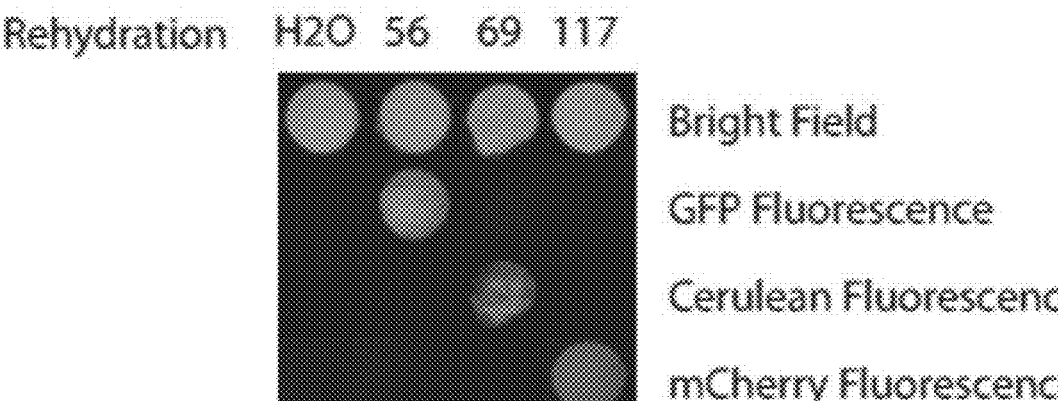
Figure 29A:
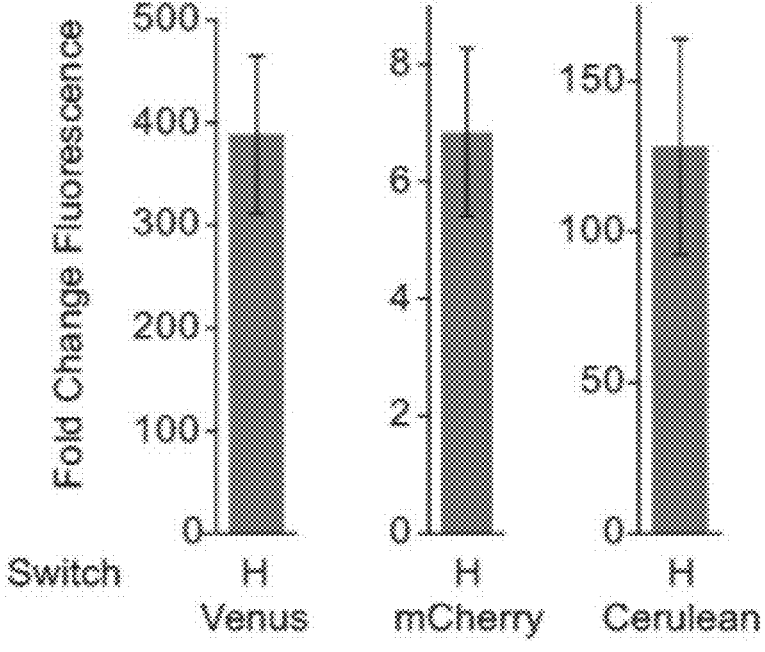
FIGS. 29A-29C are experimental data showing fold change and time course data for the color outputs from toehold switch H.
Figure 29B:
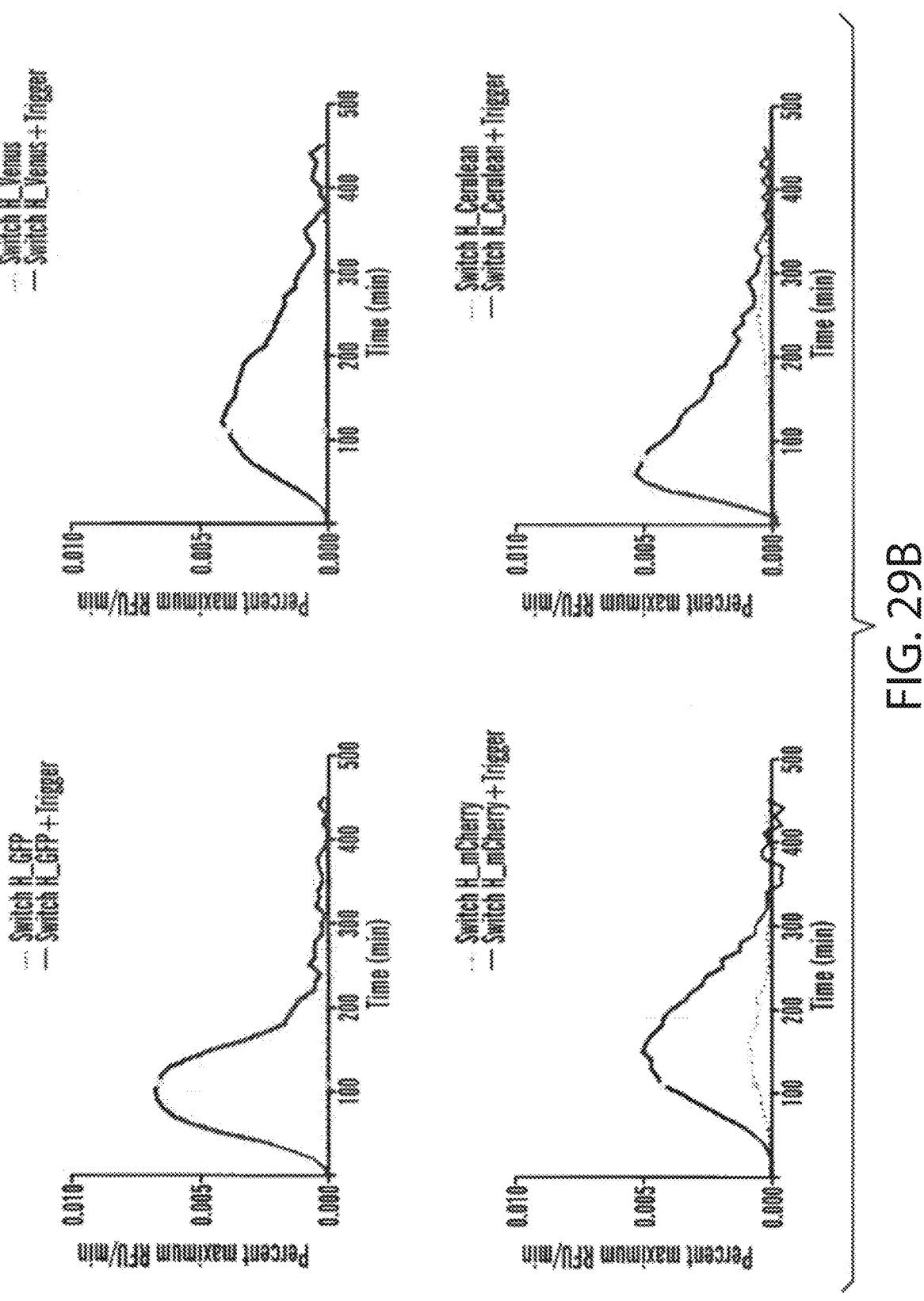
Figure 29C:
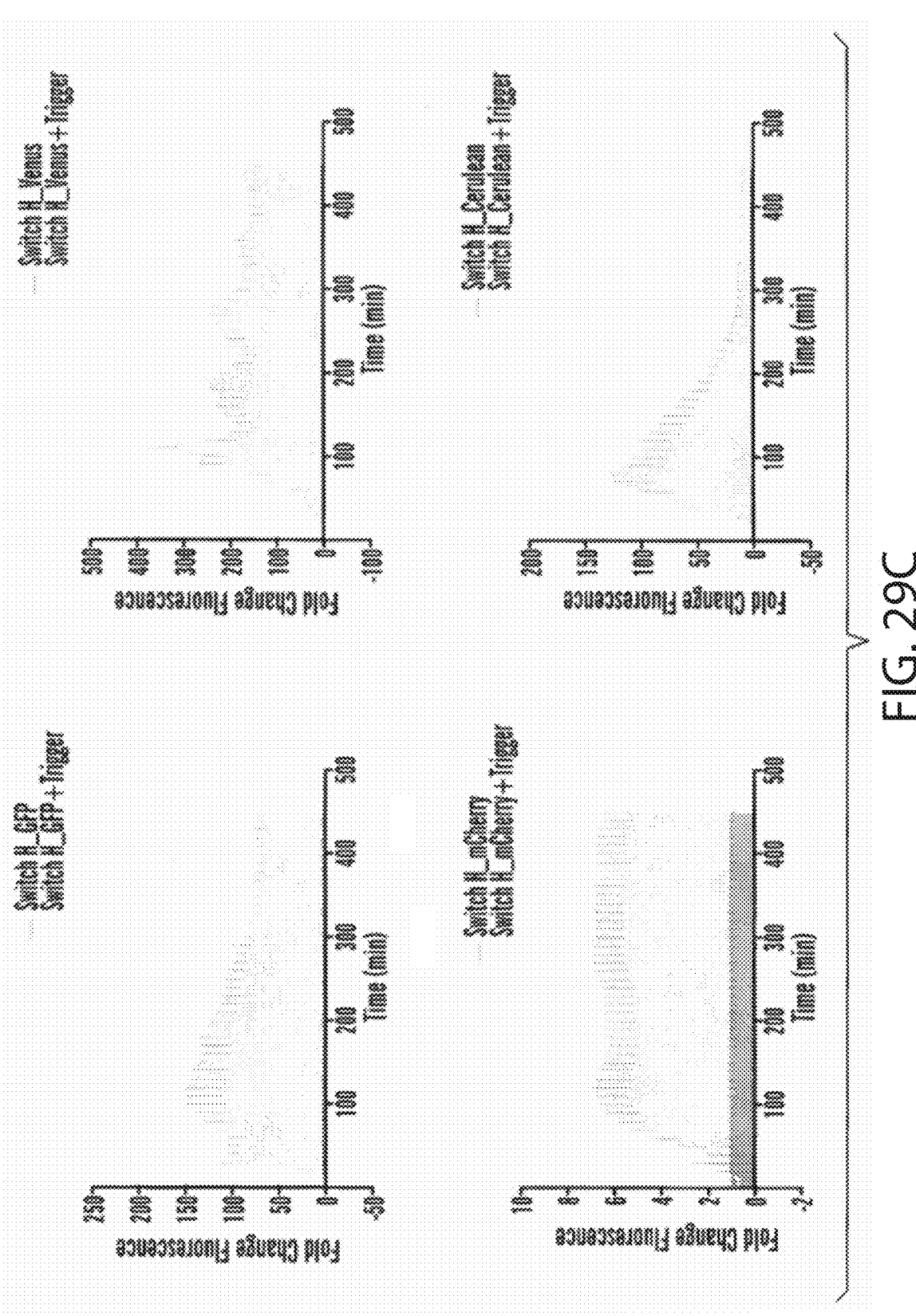

Whole-cell extracts and cellulose fibers carry an inherent autofluorescence around the emission spectrum of GFP (Schmidt, J A. 2010. Lignin and Lignans: Advances in Chemistry. Chapter 3: Electronic spectroscopy of lignans. Edited by Cyril Heitner, Don Dimmel, John Schmidt. CRC Press. Boca Raton, Fl. USA), so gene circuits to output fluorescent proteins with alternate emission spectra were also constructed for both paper and quartz discs (FIGS. 17C, 28A, 29). With these distinct outputs, a single paper disc can also be used to host multiple toehold switches, each capable of individual activation and measurement (FIG. 28B). Toehold switches in S30 T7 *E. coli* cell extracts, a lower cost alternative, were also successfully tested using circularized DNA plasmid as a template for both toehold switch and trigger RNAs (data not shown).

Figure 17D:
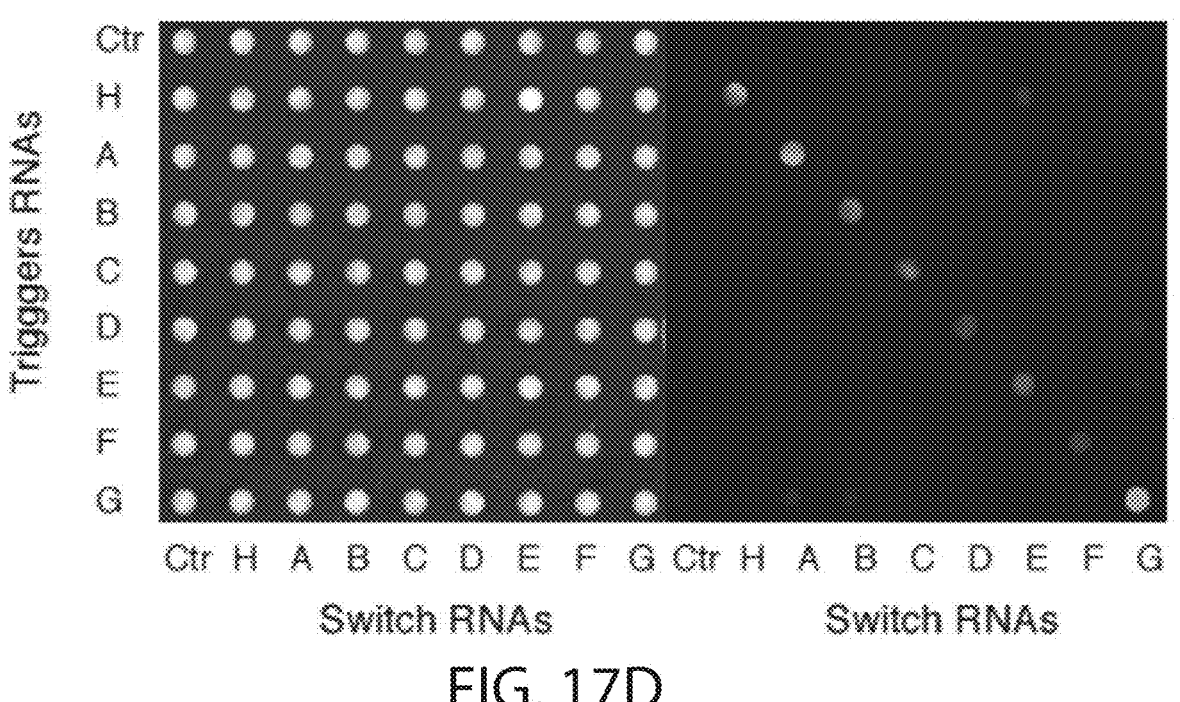
FIG. 17D is a set of bright field and fluorescence images of an orthogonality screen between toehold switches and trigger RNAs using paper-based reactions arrayed in a 384 well plate.
Figure 17E:
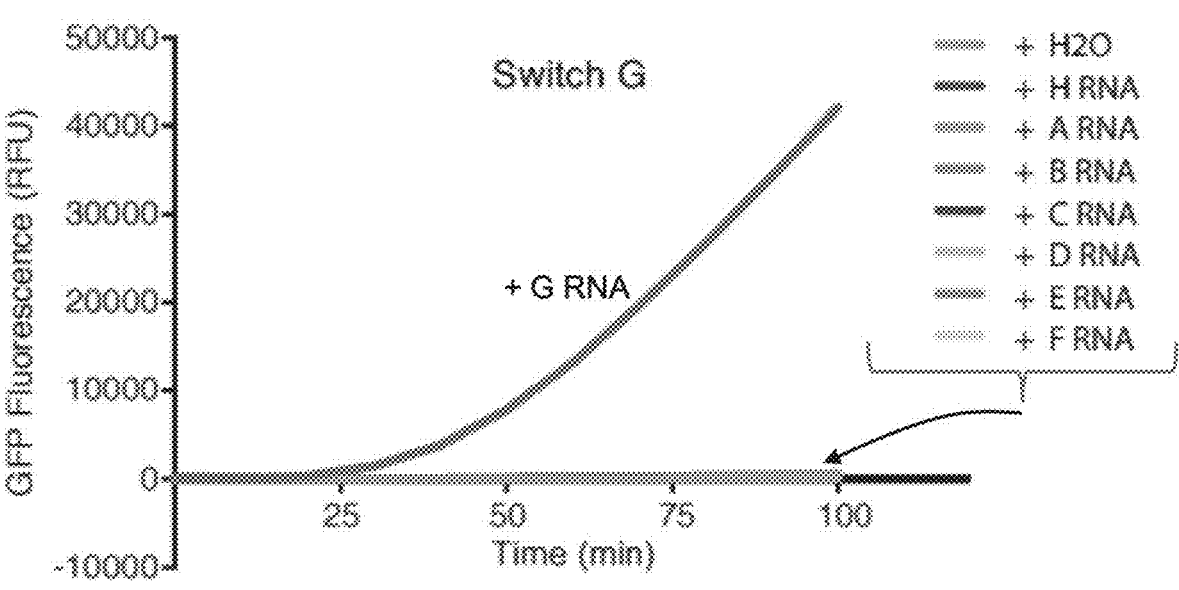
FIG. 17E is a plot showing quantification of fluorescence over time from paper discs containing switch G (bottom row). All data were generated from freeze-dried, cell-free reagents embedded into paper with their respective gene circuits. Trigger RNA concentration used for toehold switch activation, 5 uM.
Figure 27:
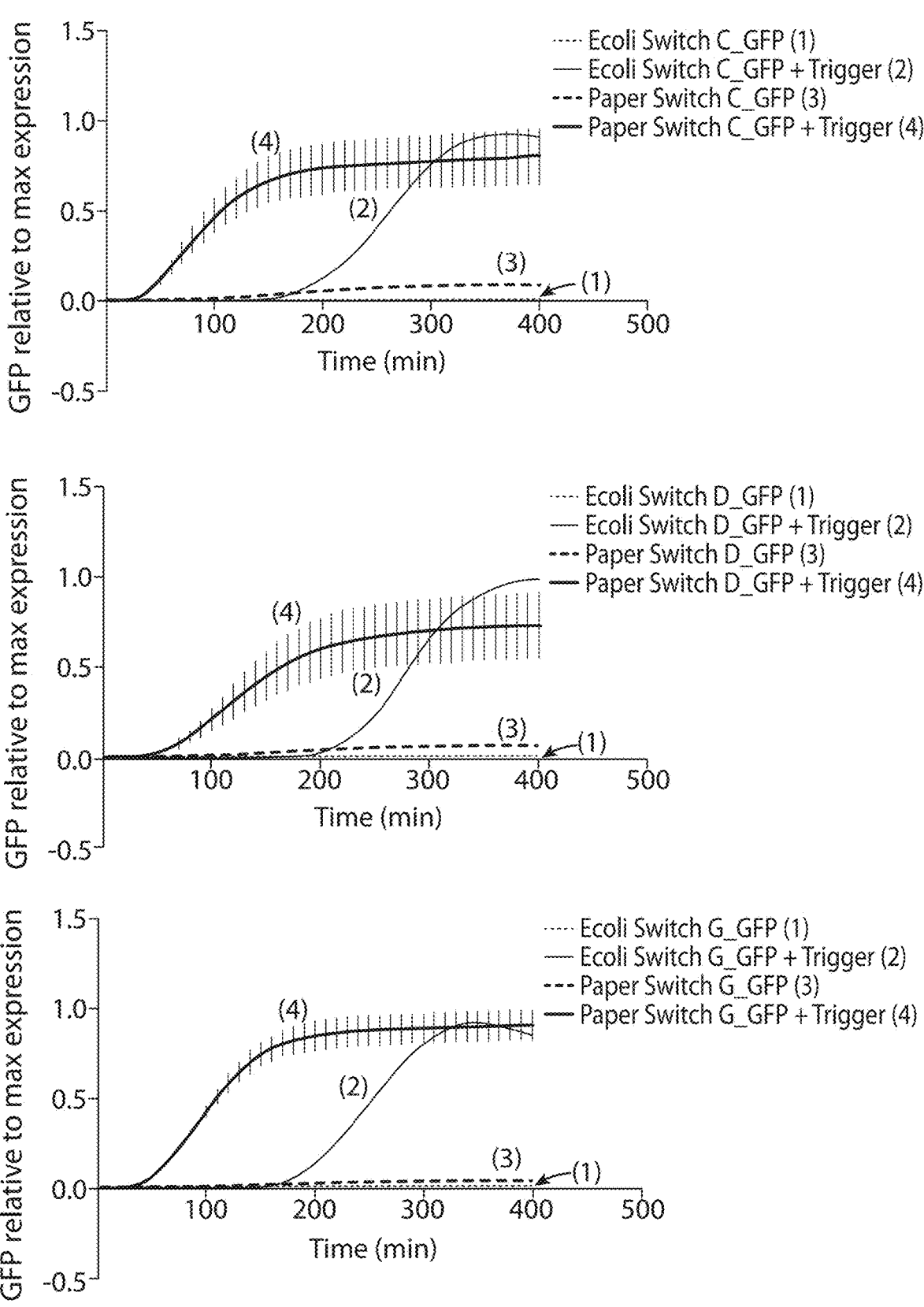
FIG. 27 is a set of plots showing comparison of toehold switch induction in *E. coli* and from freeze-dried, paper-based reactions.

By arraying the paper discs into a 384-well plate, multiplexed reactions can be easily quantified and measured over time. Here the orthogonality of the toehold switches was tested by combining each of the eight toehold hairpins against each of the trigger RNAs. As can be seen, activation of the toeholds was essentially limited to the diagonal, with only one weak off-target interaction between switch E and trigger H (FIG. 17D). Such orthogonality was reflected in the specific activation demonstrated above in the in vivo mileu of bacteria cells (FIG. 27). This arrayed approach also underscores another important advantage of the in vitro paper-based system described herein. To collect similar data in vivo would require 81 separate transformations, overnight cultures on plates and subsequent culturing in multiwell plates, which could take several days. Using in vitro paper-based reactions, this experiment took under 90 minutes to set up, and, upon incubation, signal from activated switches was detected in as little as 20 minutes (FIG. 17E).

In some embodiments, the paper-based system was designed to produce a colorimetric output visible to the naked eye. For example, GFP was replaced with the enzyme β-galactosidase (LacZ) to produce a system that generates a dramatic enzyme-mediated color change in response to conditional inputs to synthetic gene networks (FIG. 18A). LacZ cleaves the yellow substrate, chlorophenol Red-β-D-galactopyranoside, embedded into the freeze-dried paper discs, to produce a magenta chlorophenol red product.

Figures 1, 30:
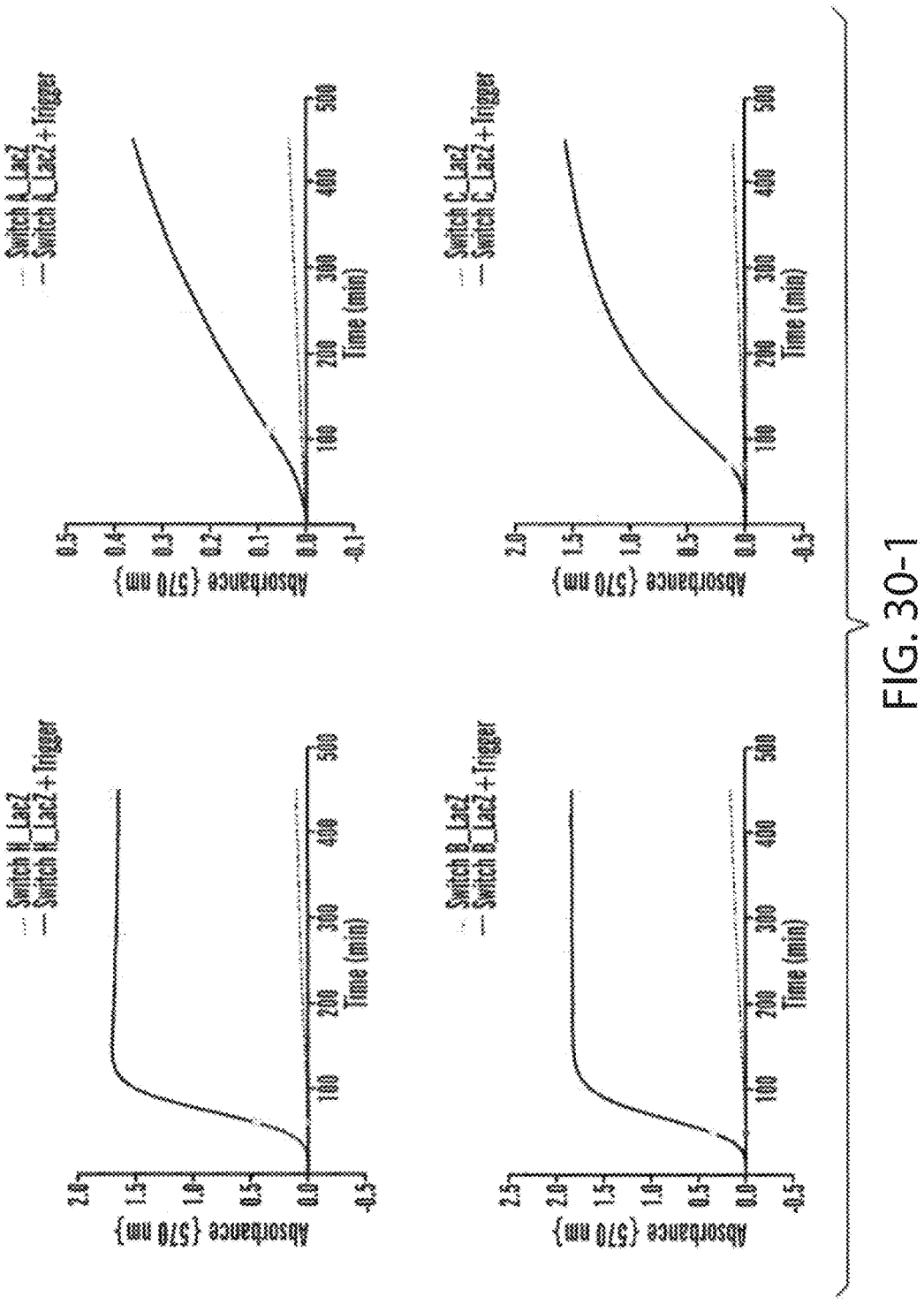
FIG. 30 is a set of plots showing paper-based regulation of LacZ colorimetric response from toehold switches A-H over time. Colorimetric response was quantified as a measure of absorbance at 570 nm. The red dots indicate the time point from which fold change calculations reported in FIG. 18C were taken. Values presented are the average of either triplicate or quadruplicate data. Error bars represent standard deviation.
Figures 2, 30:
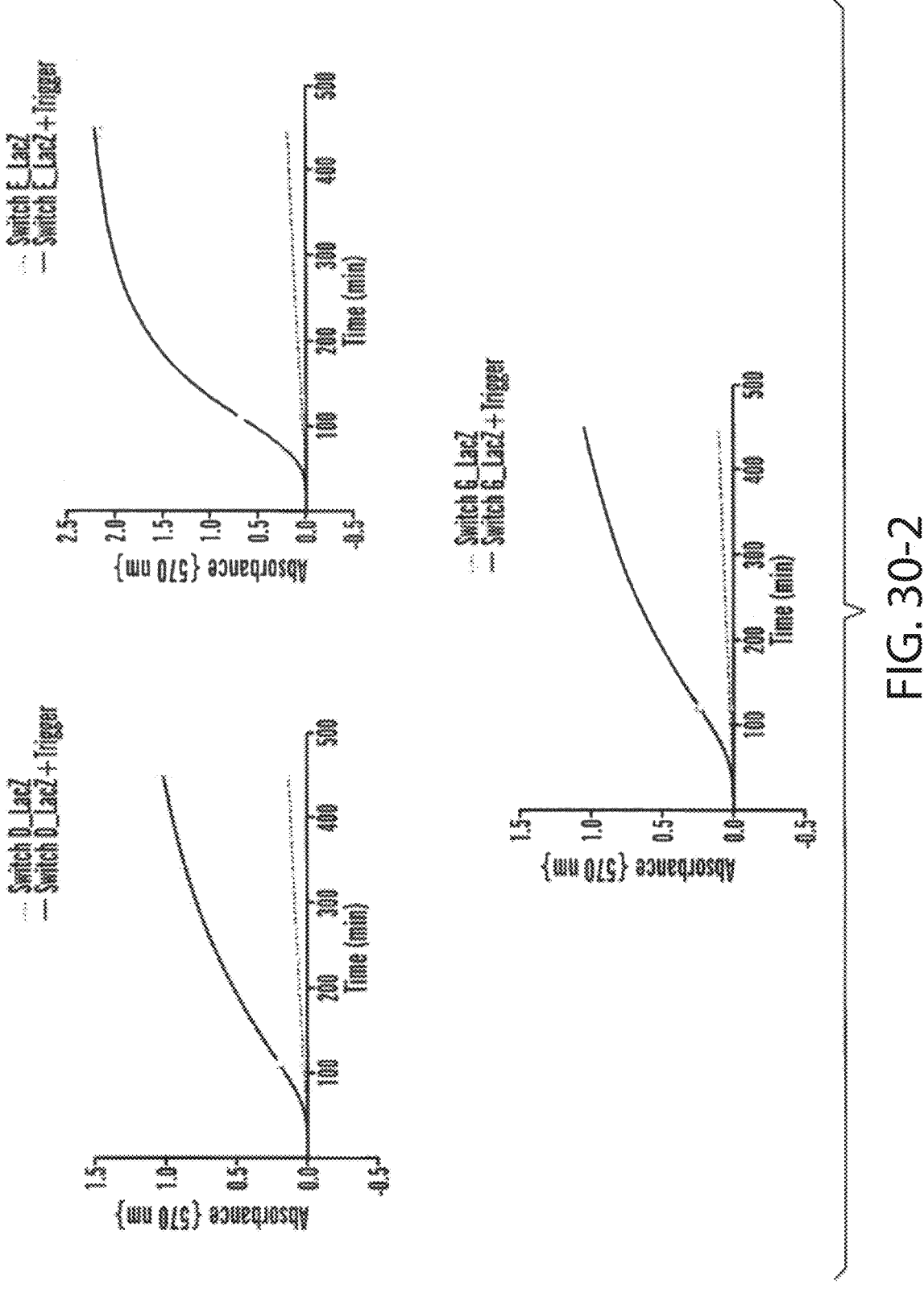
Figures 1, 31:
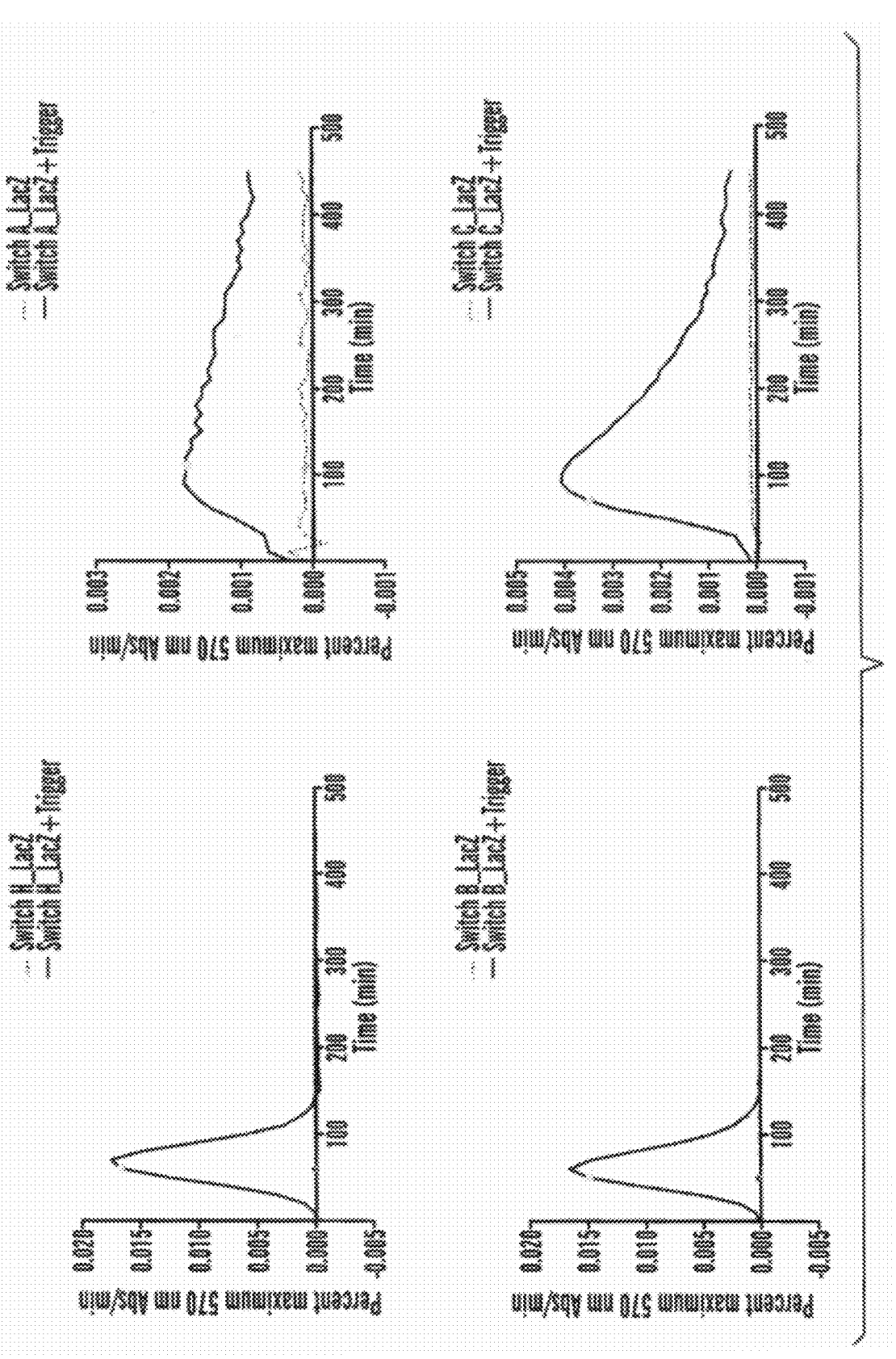
FIG. 31 is a set of plots showing rate of color change from LacZ toehold switches A-H over time. Colorimetric response was quantified as a measure of absorbance at 570 nm. The red dots indicate the time point from which fold change calculations reported in FIG. 18C were taken. Values presented are the average of either triplicate or quadruplicate data. Error bars represent standard deviation.
Figures 2, 31:
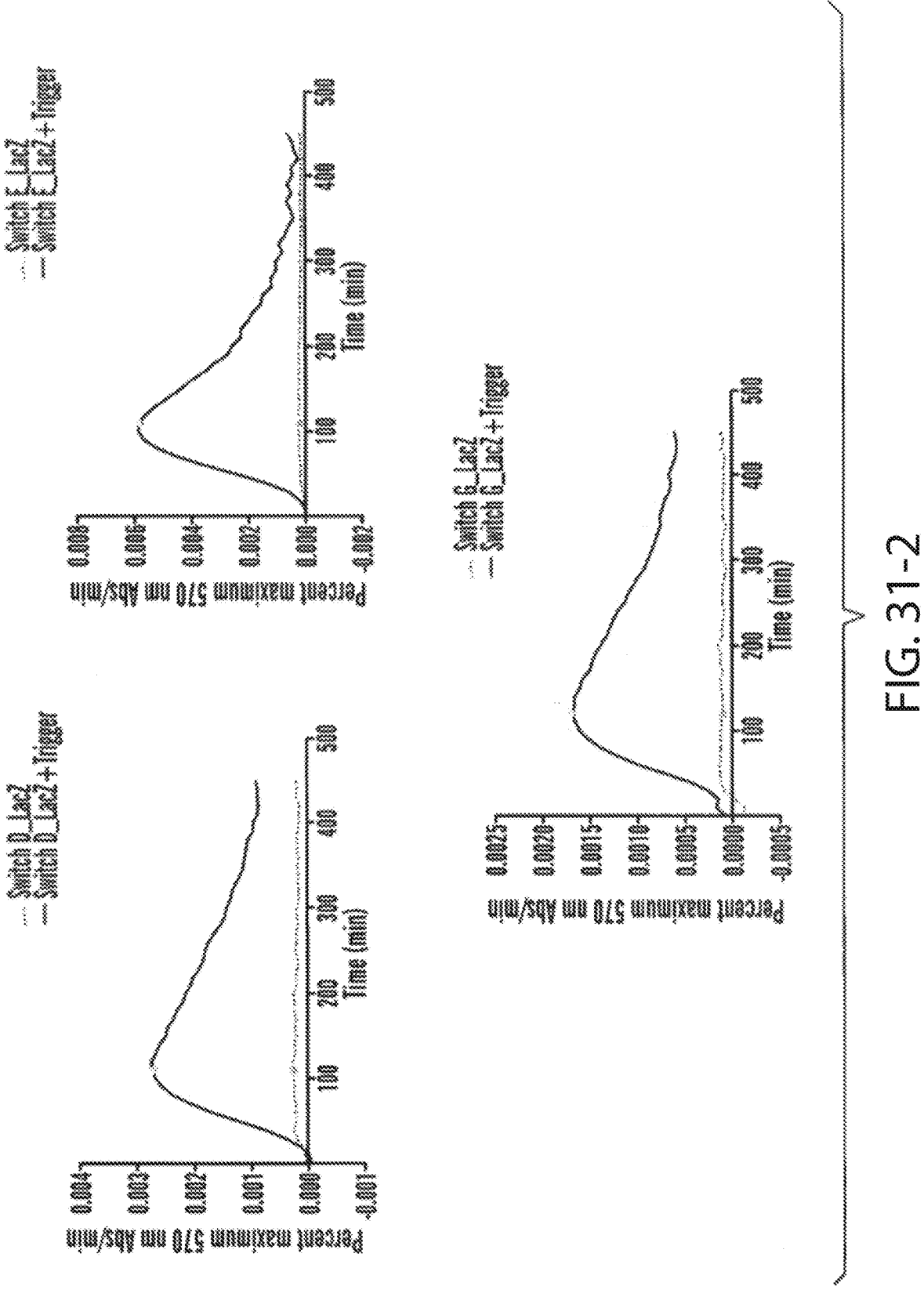
Figures 1, 32A:
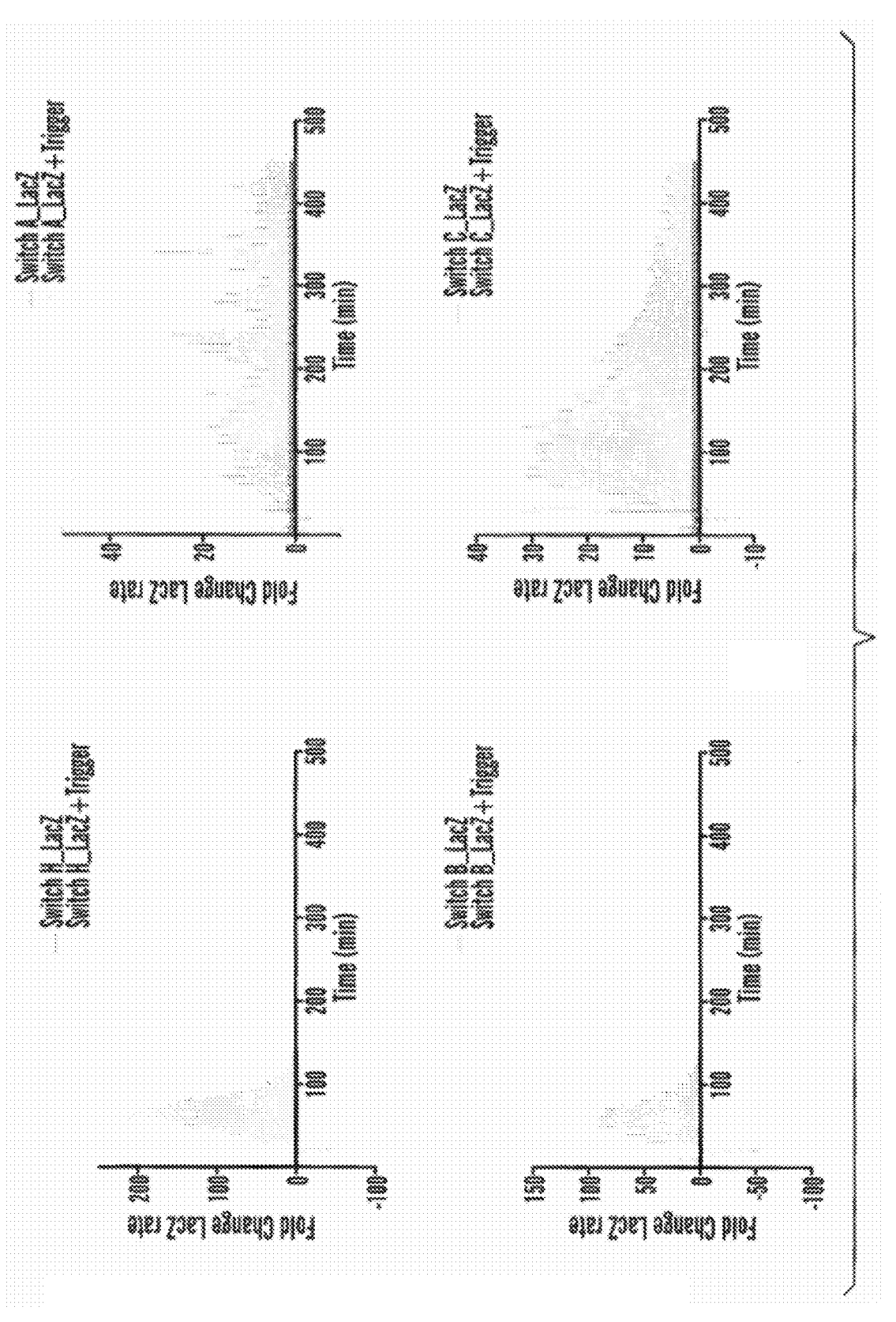
FIG. 32A is a set of plots showing rate-based fold change for LacZ colorimetric response paper-based from toehold switches, relative to uninduced controls. Values presented are the average of either triplicate or quadruplicate data. Error bars represent standard deviation.
Figures 2, 32A:
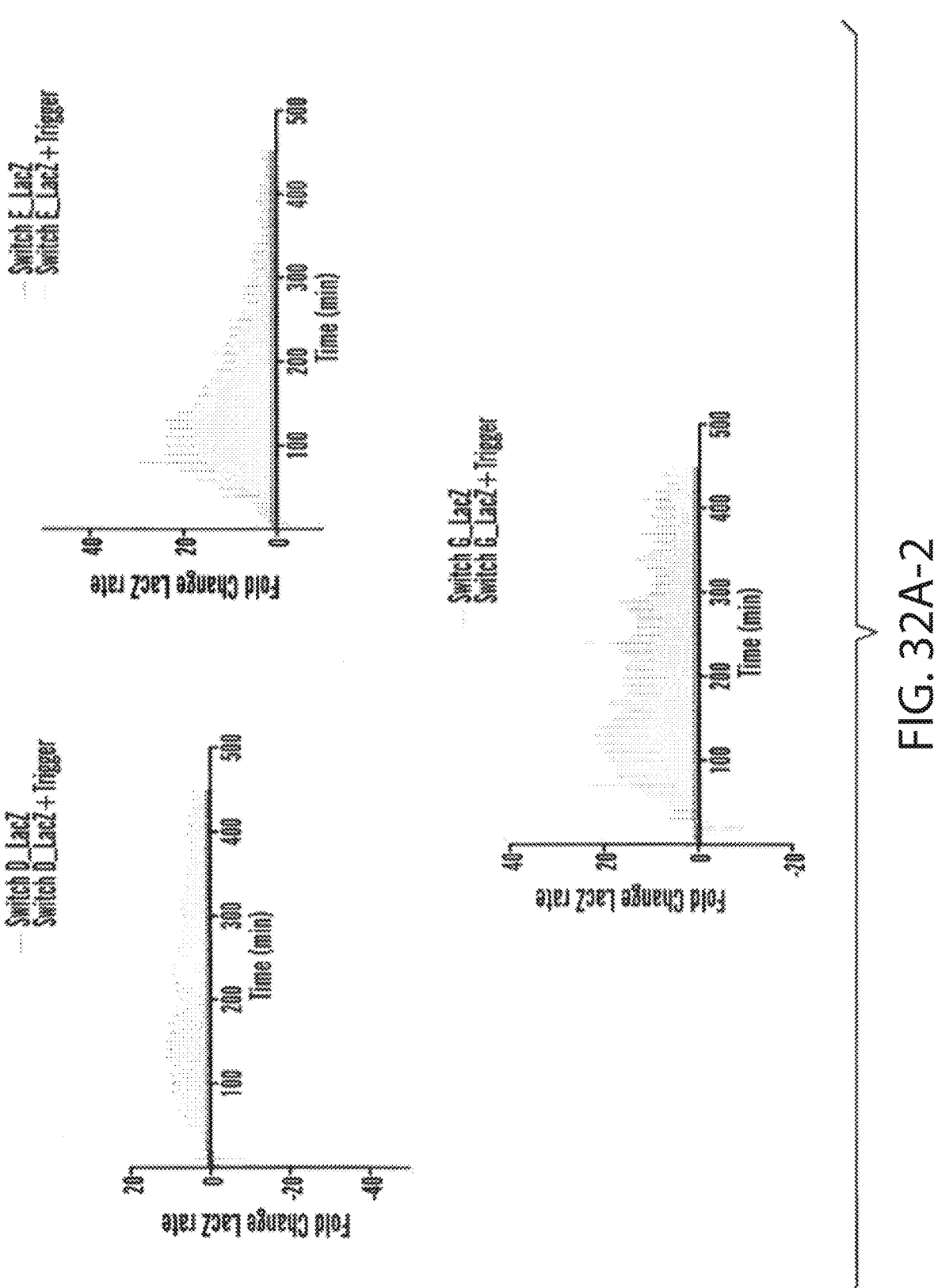
Figure 32B:
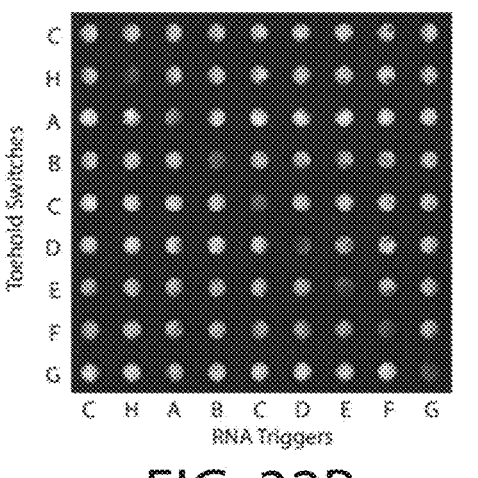
FIG. 32B is a composite image of orthogonality screen of LacZ colorimetric toehold switch reactions on paper discs arrayed in a 384-well plate.
Figure 33A:
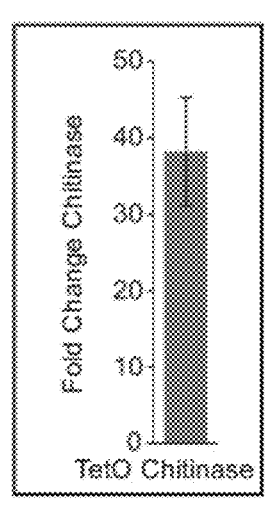
FIGS. 33A-33D show an alternative chitinase-based colorimetric output on paper.
Figure 33B:
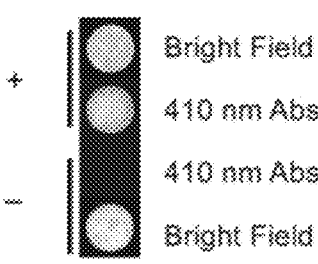
Figure 33C:
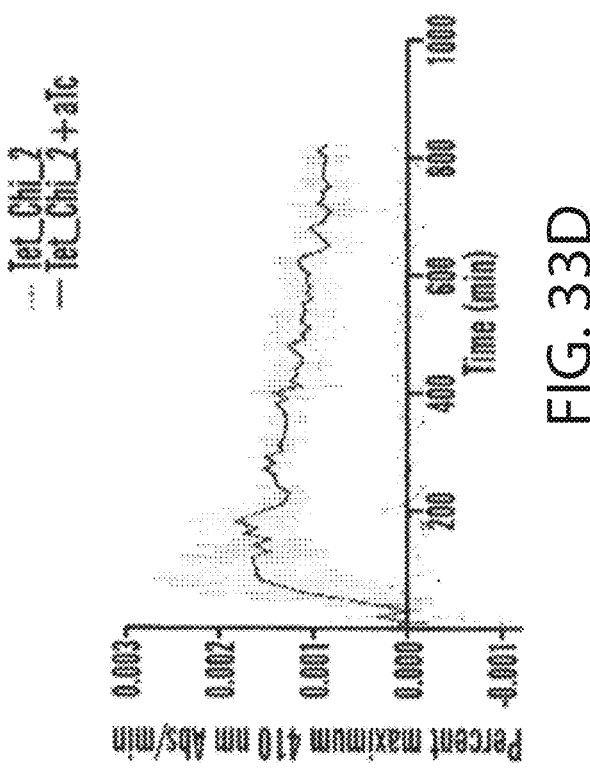
Figure 33D:
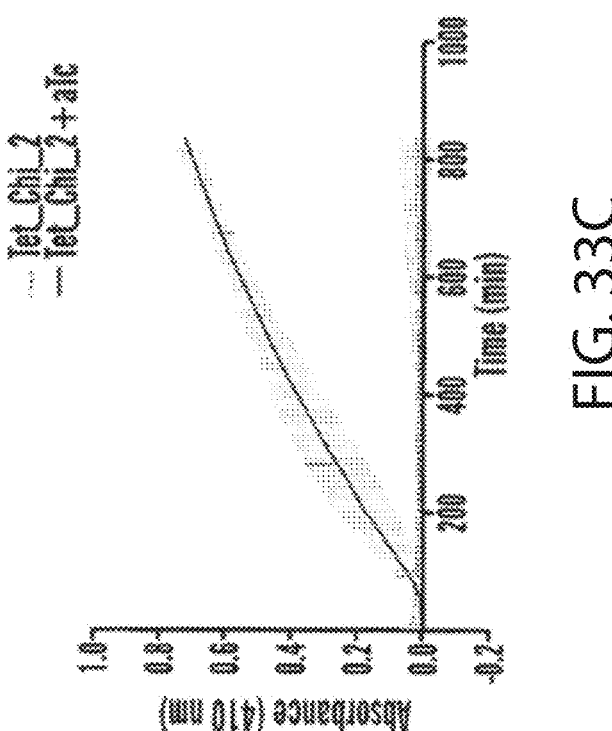
Figure 33E:
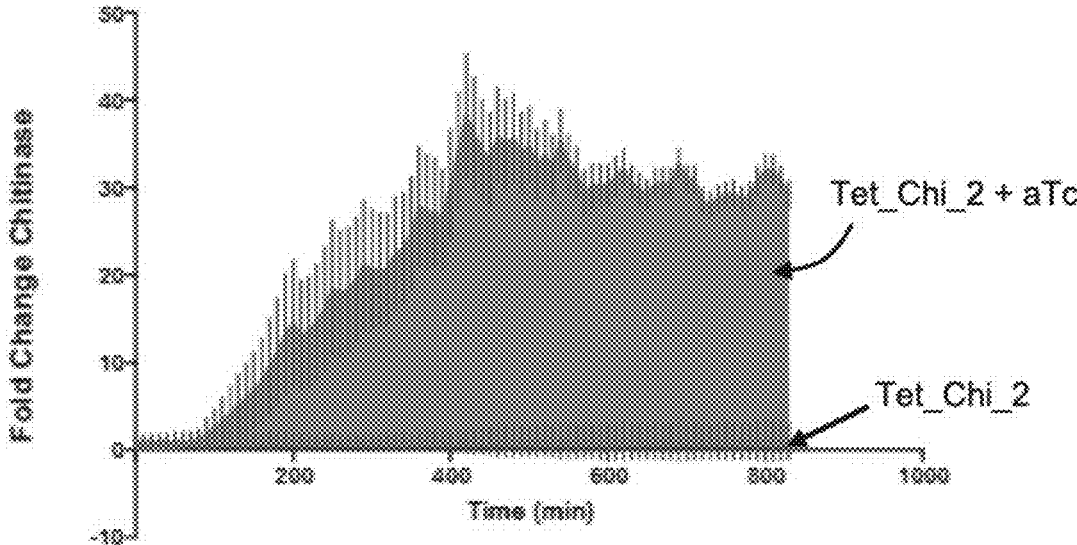
FIG. 33E is a plot of fold change of absorbance output from aTc-induced TetO chitinase relative to uninduced control. Values presented are the average of either triplicate or quadruplicate data. Error bars represent standard deviation.

These color-based reactions can be measured on standard plate readers by monitoring the absorbance maximum of the LacZ product of 570 nm. As with fluorescent outputs from the eight GFP toehold switches, each triggered LacZ switch produces a unique dynamic response with maximum expression rates occurring between 50 and 120 minutes, and reaction dynamics being switch dependent (FIGS. 18B, 18C, 30). Some toehold switches rapidly reached their maximum output, while others produced a relatively linear output throughout overnight experiments. To maximize early detection and sensitivity, enzymatic reaction rate determined from the slope 570 nm absorbance over time was used to calculate fold change for the family of LacZ toehold switches (FIGS. 18C, 31, 32). As with the fluorescent reactions, paper-based reactions with colorimetric outputs can be arrayed for large-scale, quantitative experiments (FIG. 32).

Figure 18D:
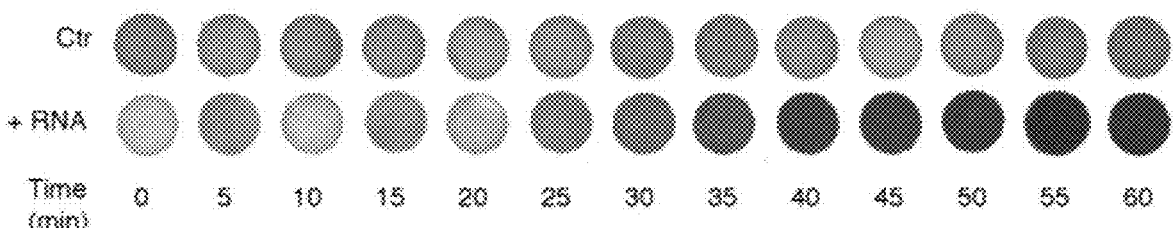
Figure 18E:
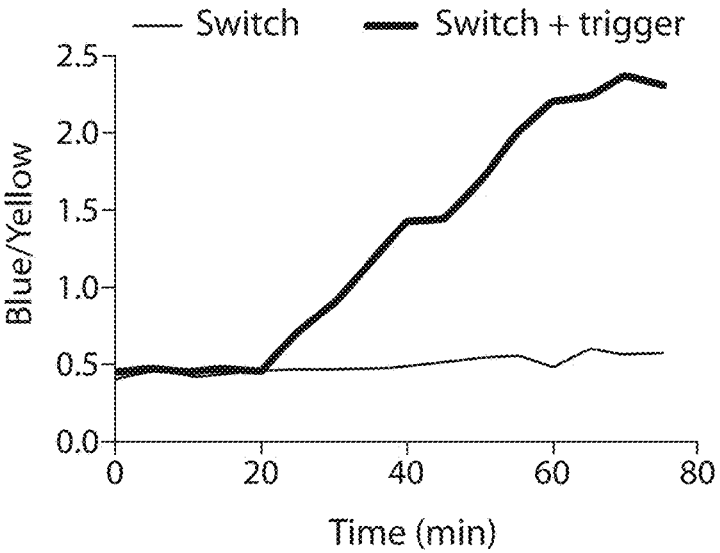
Figure 18F:
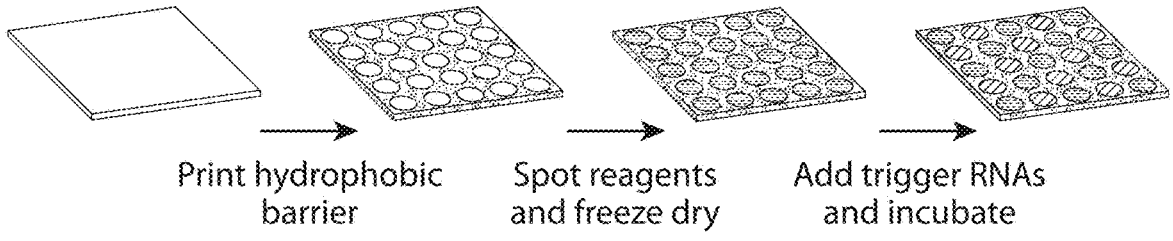

Using switch D to demonstrate color development, detection of the reaction can be seen to begin around 25 minutes and saturates in around one hour (FIG. 18D). Quantification of these reactions can also easily be done by measuring the intensity of the color channels red, green and blue from images produced by most cameras, including those widely available in cellphones. By tracking the generation of blue signal, relative to yellow (red+ green), the progress of the activated freeze-dried toehold reaction can be tracked (FIG. 18E). Similar results were observed for the whole family of toehold switches (FIG. 18B).

An alternative colorimetric reporter enzyme, chitinase, was also incorporated into synthetic gene networks for systems based on extracts from cells that contain a lacz background. As demonstrated with the teto_chitinase switch, the presence of atc inducer results in the expression of chitinase, which cleaves a colorless substrate (4-nitrophenyl n,n'-diacetyl-beta-d-chitobioside) to yield a yellow p-nitrophenol product. The colorimetric output is visible to the naked eye and can be quantified using a plate reader utilizing absorbance (410 nm; FIG. 33). Color development with this system was linear from the onset of detectable output at about 60 min, until the end of the experiment at 800 min, with a maximum induction of 38-fold at 420 min.

Figure 18G:
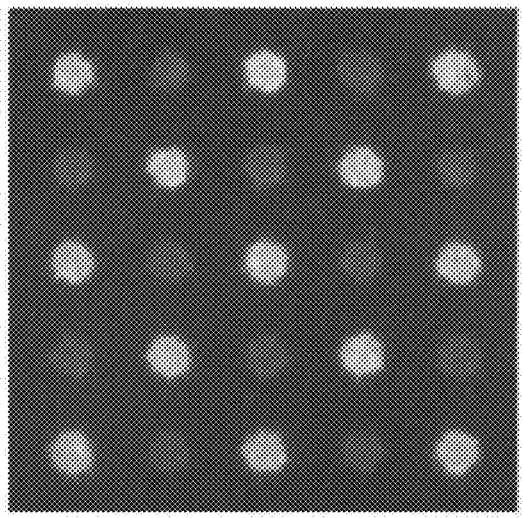

An important advantage of paper-based distribution of synthetic gene networks is their low cost and easy method of manufacture. As a proof-of-principle demonstration, techniques from materials science were adopted to create printed arrays of stable synthetic gene networks using a standard computer printer and chromatography paper. A commercially available wax-based ink serves as a hydrophobic barrier separating respective reaction spaces to create custom arrays and layouts. As a demonstration of the technique, 5×5 arrays were printed to host LacZ expressing toehold switches (FIG. 18G).

Figure 18H:
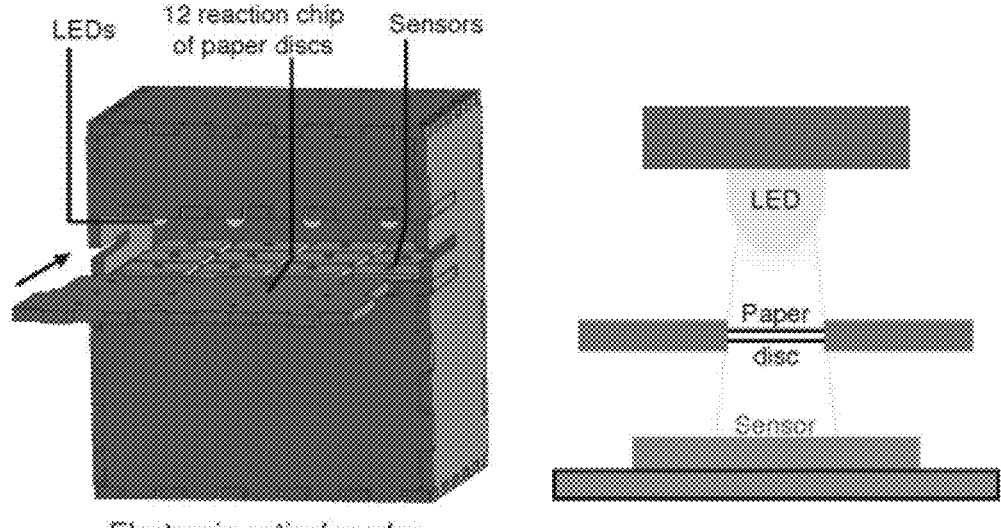
Figure 18I:
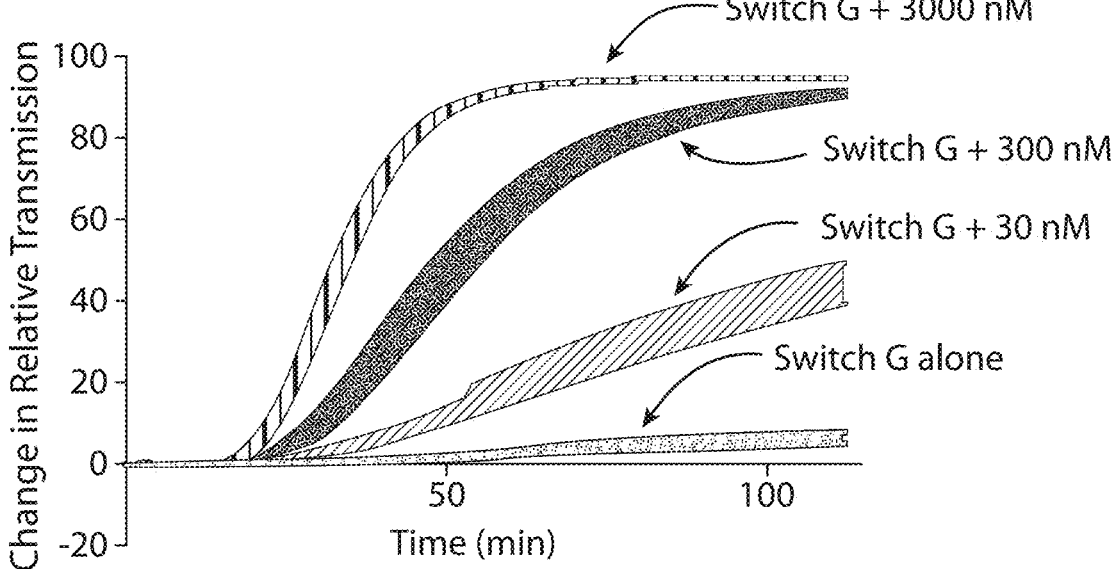

For practical applications, a low-cost electronic optical reader was built to permit quantification, and ultimately, automation of the paper-based reactions. Such a device could also impart these molecular devices with the ease of use and convenience of a home glucose monitor. LacZ-based toehold switches on paper discs were placed between LED light sources (570 nm) and electronic sensors (FIG. 18H). In the event of a positive reaction, light transmission is progressively blocked by the production of the purple LacZ cleavage product. LEDs and sensors were coordinated through multiplexers connected to an Arduino that controlled the read pattern and rate parameters. Electronic hardware was housed using computer-designed parts laser cut from acrylic, to create a device for under $100 USD (FIG. 18H). Freeze-dried paper discs were placed into holes on a chip, rehydrated, incubated within the device at 37° C. and monitored in real-time through an attached laptop. As a proof-of-concept, the G_LacZ toehold switch was tested, and consistent and significant reads from different concentrations of RNA trigger were observed (FIG. 18I).

Next, toehold switch sensors capable of detecting full-length active mRNA targets were developed, a desirable feature for a diagnostics platform. The first goal was the detection of GFP and mCherry mRNA. Using an algorithm that predicts RNA secondary structure, sensors were built to target sequences likely to be accessible for binding (Green et al., 2014), and, when tested, yielded fluorescent induction in the presence of GFP (60-fold) and mCherry (13-fold) mRNAs, respectively (FIGS. 19B-19C).

Figure 19A:
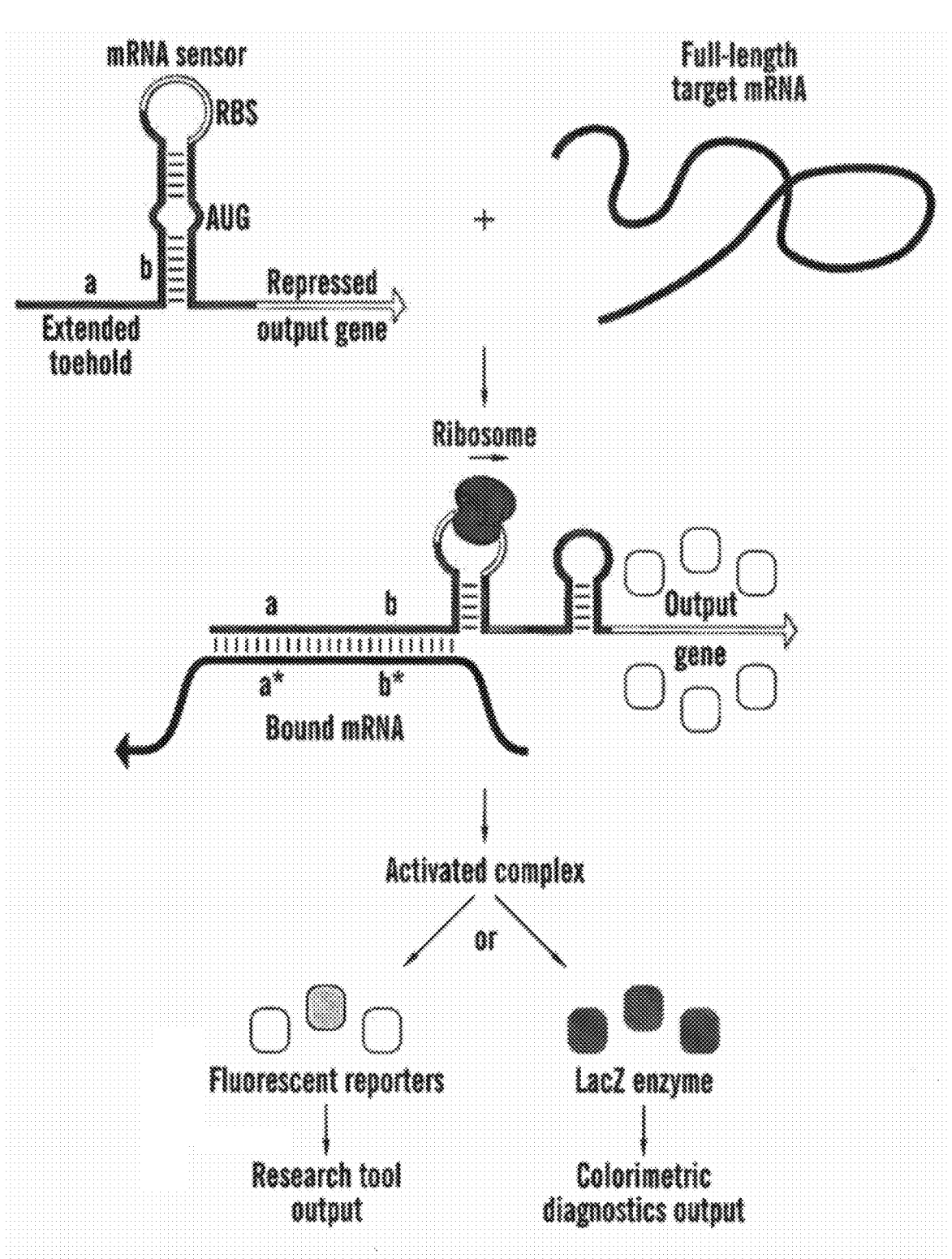
FIG. 19A is a schematic of the paper-based mRNA sensors based on toehold switches.
Figure 34B:
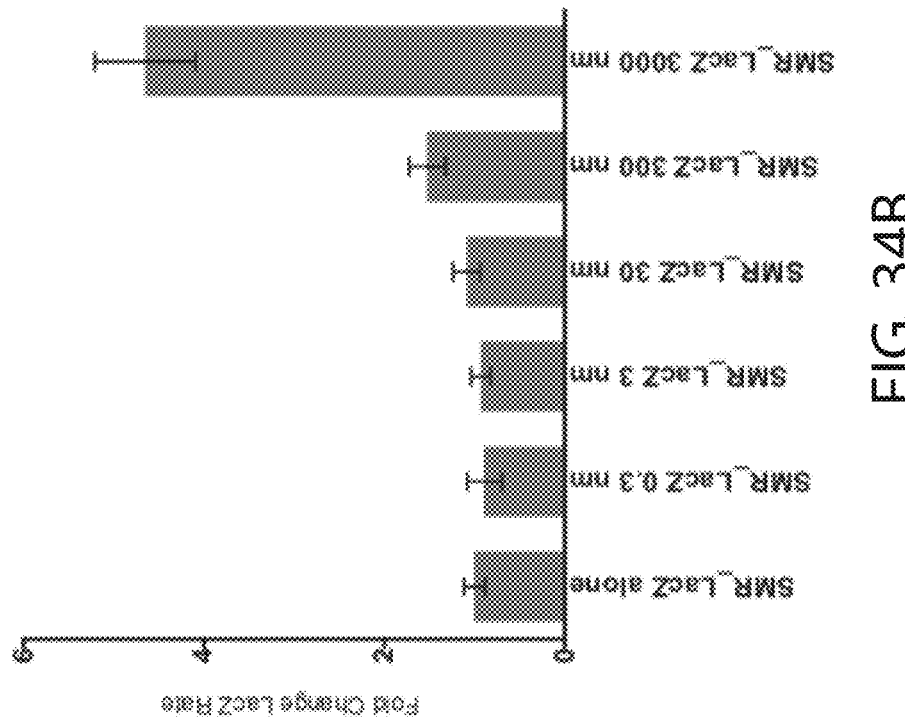
FIGS. 34A-34D are experimental data showing titration of full-length target mRNA for paper-based antibiotic resistance gene mRNA sensors with LacZ output. Summary of rate-based fold change for LacZ mRNA sensors for (FIG. 34A) kanamycin, (FIG. 34B) spectinomycin, (FIG. 34C) chloramphenicol and (FIG. 34D) ampicillin resistance gene (Plate reader, Abs 570 nM). Values presented are the average of either triplicate or quadruplicate data. Error bars represent standard deviation.
Figure 34A:
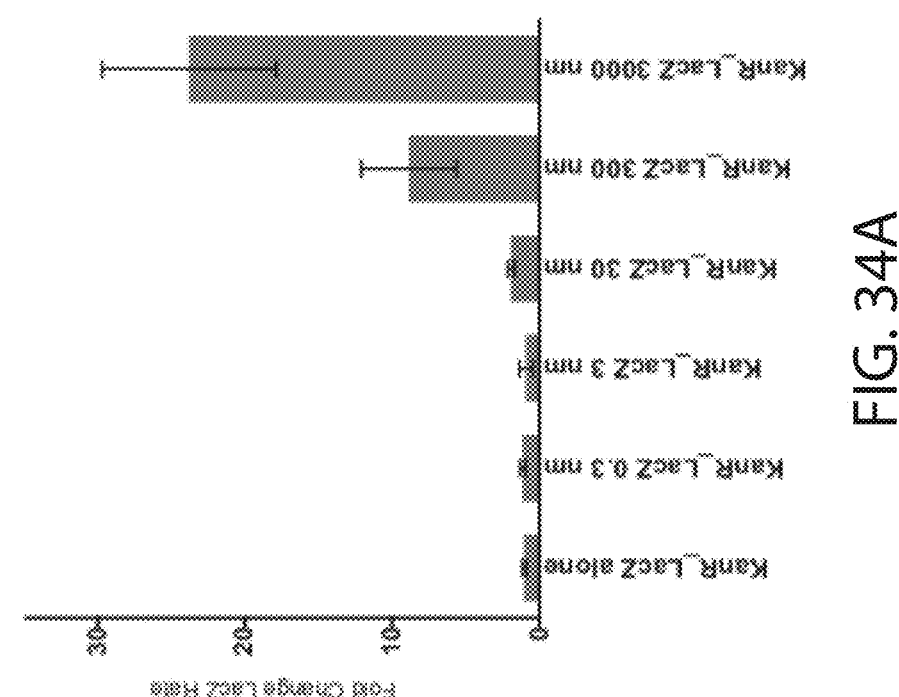
Figure 34D:
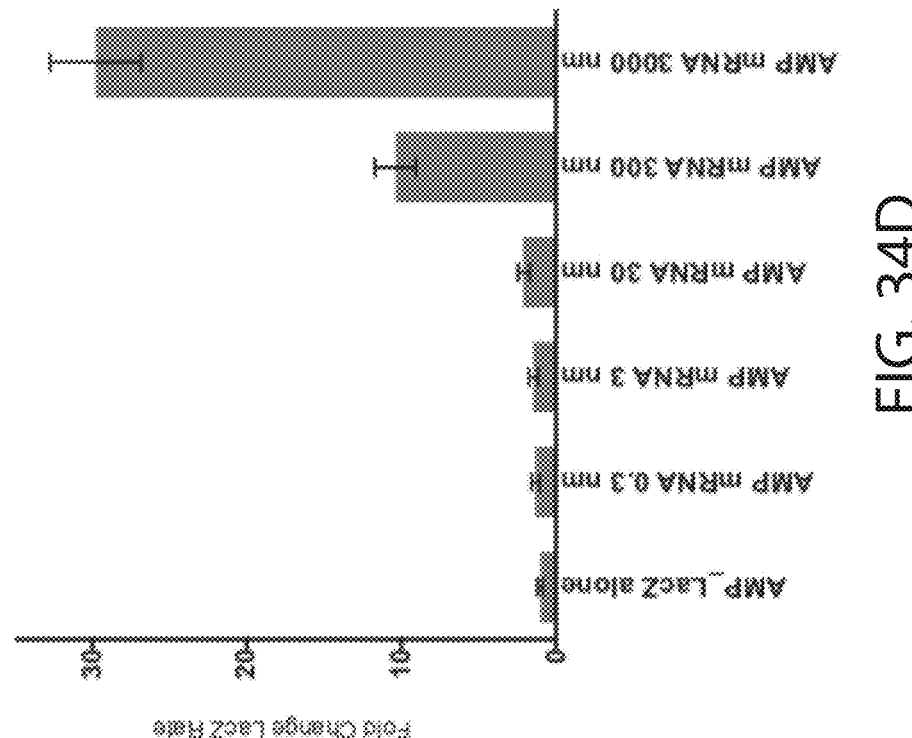
Figure 34C:
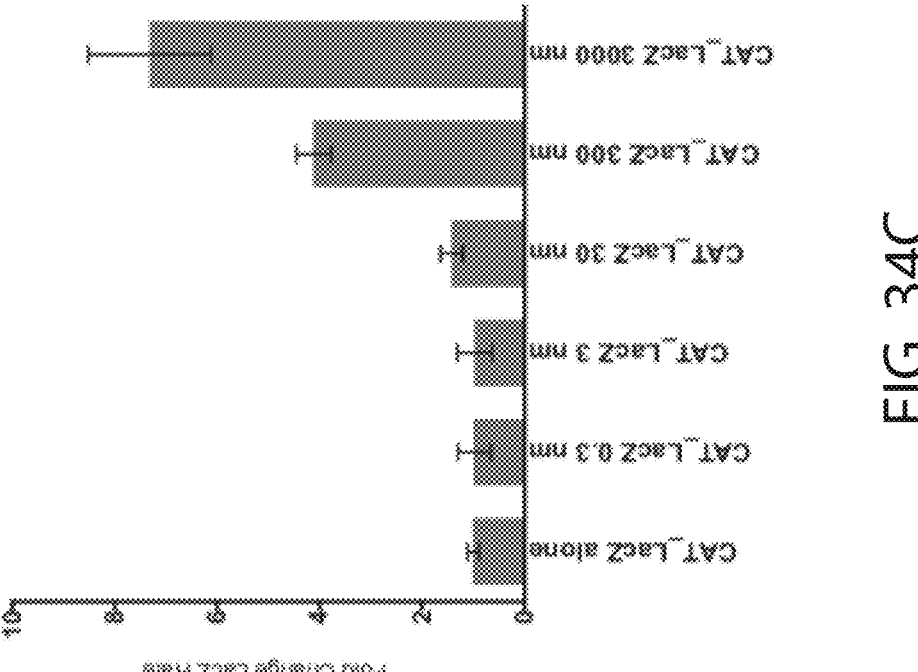
Figure 35A:
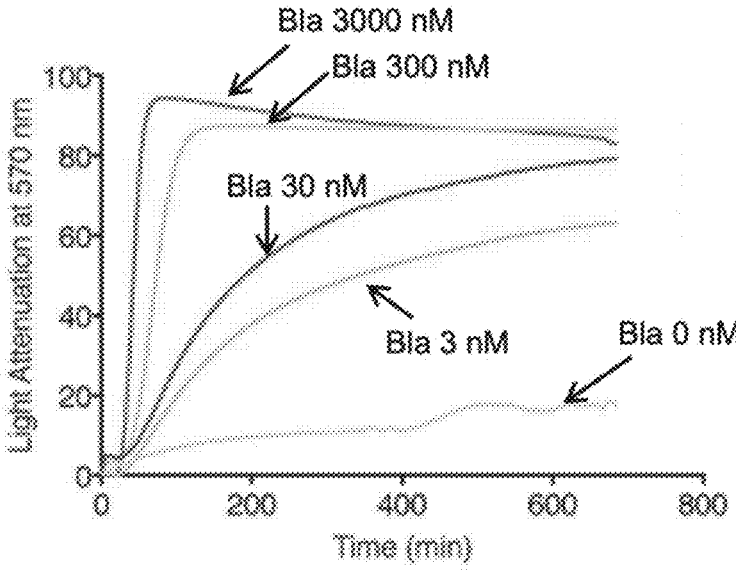
FIG. 35A is a plot of time course for the ampicillin resistance sensor from the low cost, electronic optical reader. Values presented are the average of either triplicate or quadruplicate data.
Figure 35B:
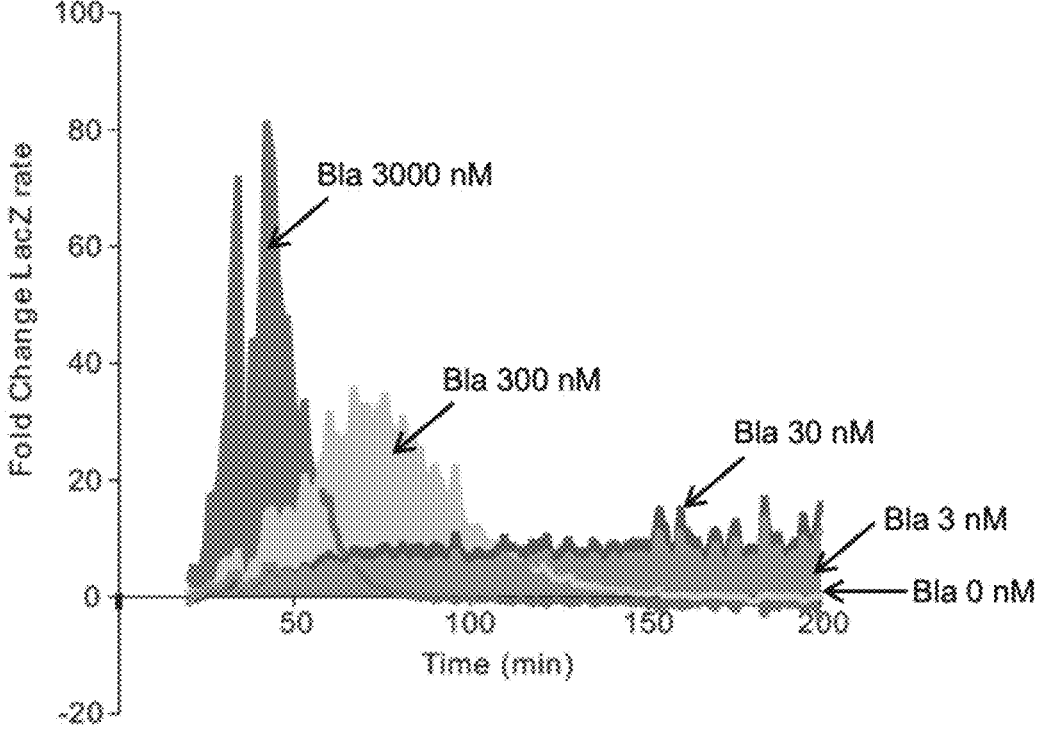
FIG. 35B is a plot showing measurement of fold change of LacZ rate by paper-based ampicillin resistance gene mRNA sensor with LacZ output over time.

As a demonstration of the potential for paper-based synthetic gene networks as an in vitro diagnostics platform, colorimetric mRNA sensors for antibiotic resistance genes were next developed (FIG. 19A). In freeze-dried, paper-based reactions, mRNA sensors for spectinomycin (5-fold), chloramphenicol (7.5-fold), kanamycin (24-fold) and ampicillin (30-fold) resistance genes yielded significant LacZ induction in the presence of their respective mRNAs (3000 nM, FIGS. 19D and 34). The ampicillin resistance mRNA sensor was then tested in the electronic optical reader and found significant detection of target transcripts as low as 3 nM (FIGS. 19E and 35). Moreover, the signal from the purpose-built device was about three times greater than the plate reader at equivalent trigger RNA concentrations (FIGS. 19D-19E, 34D). Tracking the fold change read out over time, it can be seen how the concentration-dependent reaction rate impacts the appearance and duration of the positive signal (FIG. 35B).

Figure 36:
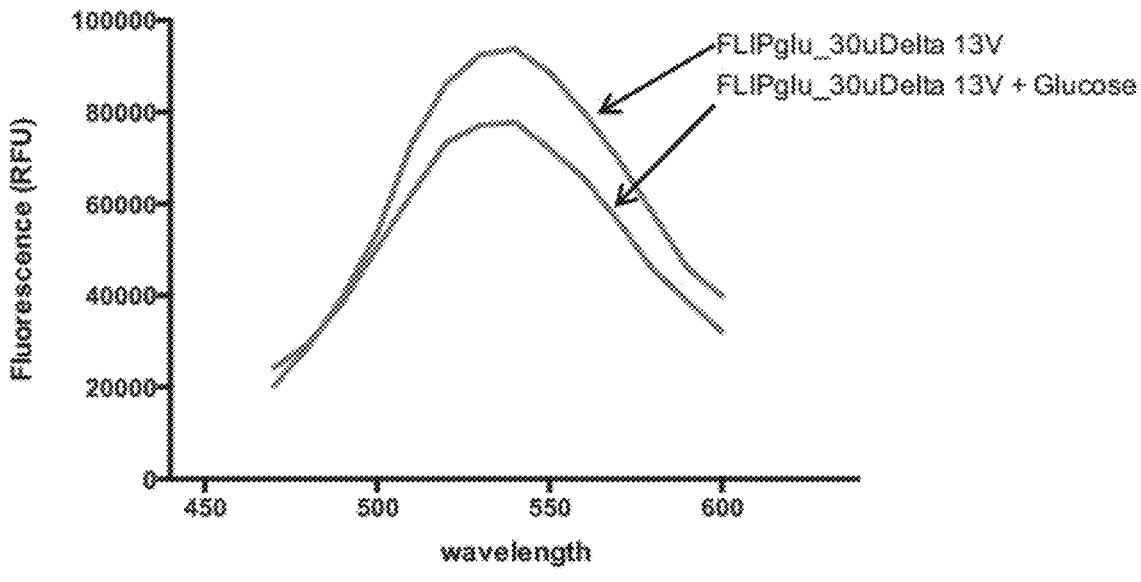
FIG. 36 is a plot of fluorescence spectrum of FRET-based glucose nanosensor in the presence and absence of 10 mM glucose. Using freeze-dried, cell-free expression in Hela cell extracts, the 528 nm fluorescence peak of the nanosensor is suppressed in the presence of glucose as previously reported. RFU, relative fluorescence units.

In addition to the purpose-built synthetic gene networks presented above, this in vitro paper-based approach also holds tremendous potential for hosting other gene circuits, including those already in the literature as synthetic biology tools. Moreover, while the work above focused on bacterial components, it is readily extendible to mammalian-based systems. As confirmation, a paper-based system using freeze-dried Hela cell extracts was tested and strong expression of GFP in the presence of an expression plasmid was found (FIG. 19F). To demonstrate the use of a pre-existing molecular tool, a portable, in vitro glucose sensor on paper was built using a FRET-based nanosensor originally designed for measuring glucose in mammalian cells (FIG. 19G; Takanaga H, Frommer W B, FASEB J. 2010, 24:2849-58). The DNA construct for the nanosensor was freeze-dried along with Hela cell extracts onto paper and the paper discs were rehydrated in the presence or absence of glucose. Upon rehydration, the glucose-related shift was observed, within a physiologically relevant glucose concentration range (0, 5, 10 mM; FIGS. 19H, 36). Importantly, in this context, de novo translation of the nanosensor seems to be critical to function; freeze dried preparations of pre-translated protein did not exhibit the characteristic shift in fluorescence.

Figure 39A:
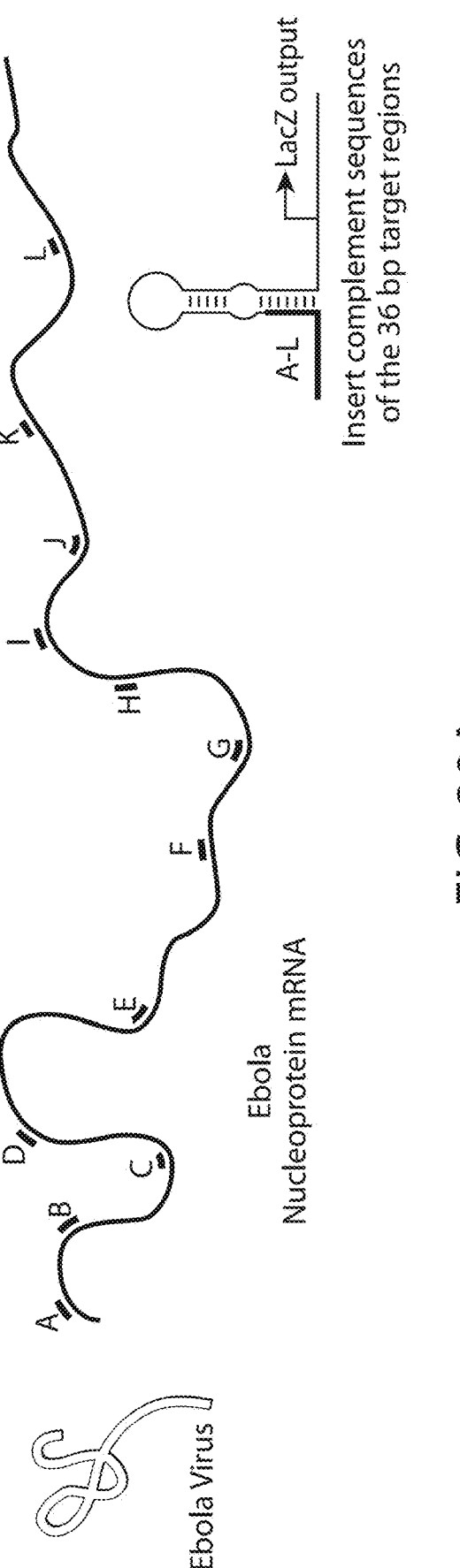
FIGS. 39A-39E demonstrate rapid prototyping of paper-based RNA sensors for sequences from Sudan and Zaire strains of the Ebola virus.

The low cost of manufacturing (4-65 ¢/sensor) is an important feature of the paper-based platform for diagnostics. However, perhaps even more important for the adoption and potential impact of this technology is the time and cost of developing new sensors. To test how rapidly new sensors could be developed, mRNA sensors for the viral pathogen Ebola were built. The goal was to construct and test 24 sensors that could distinguish between the Sudan and Zaire strains of the virus in under a day. Using algorithm, sensors were designed to target mRNA from 12 regions (A-L) of the ORF for the Ebola nucleoprotein gene, which differs in length by only three nucleotides between the Sudan and Zaire strains (FIG. 39A). Construction began with PCR amplification of synthetic 135-nt DNA oligos bearing the toehold switch sensor cassettes, followed by ligation of the modules to the LacZ reporter chassis. The ligated product was then amplified by PCR. Followed by only column purification, sensors were tested on paper discs containing the freeze-dried PT7 cell-free system for testing in the presence and absence of 36-nt trigger RNAs. Due to potential challenges with access to full-length material, short trigger RNAs were used rather than full-length mRNA to test the sensors. While accessibility due to RNA secondary structure is important to keep in mind, work from previous mRNA sensors suggests that short RNA triggers provide a representative indication of sensor function.

Figure 39B:
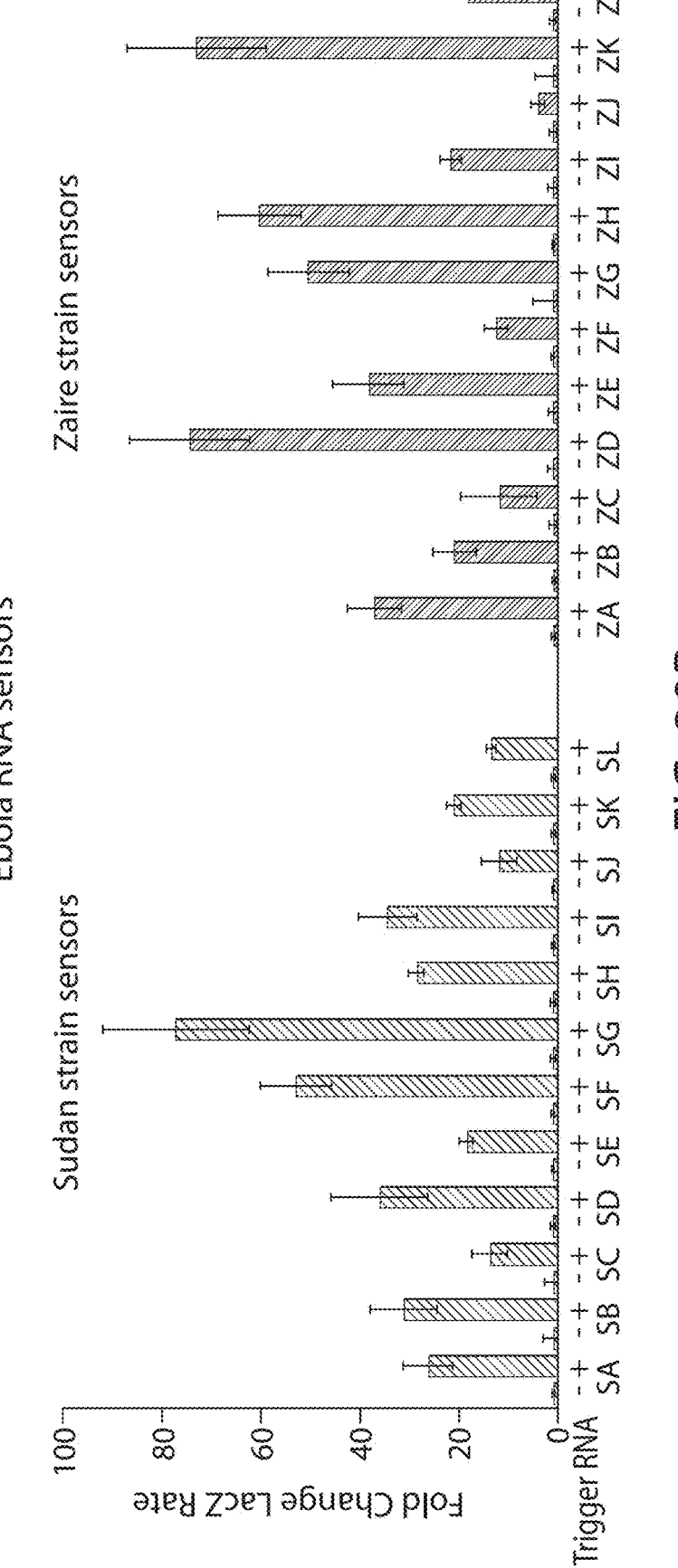
Figure 39C:
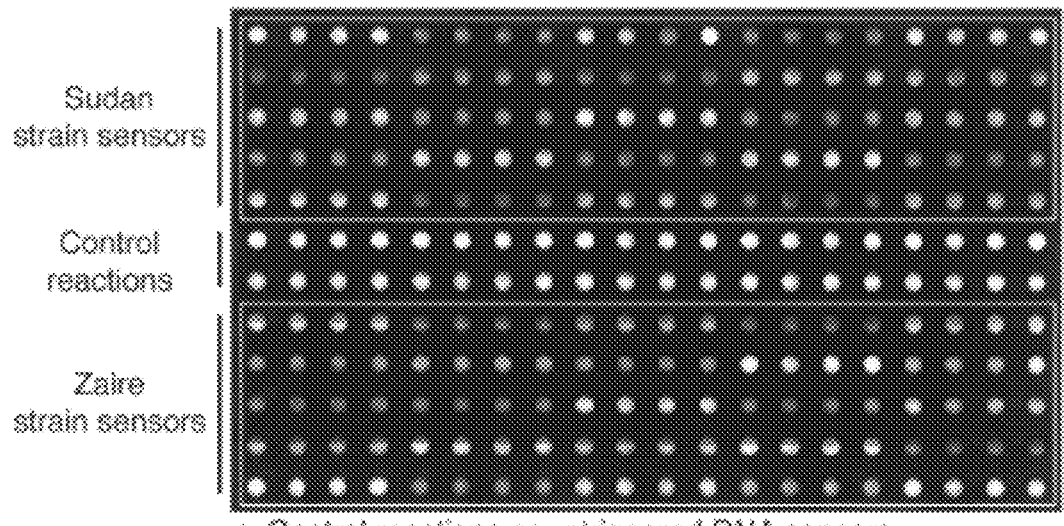
Figure 39D:
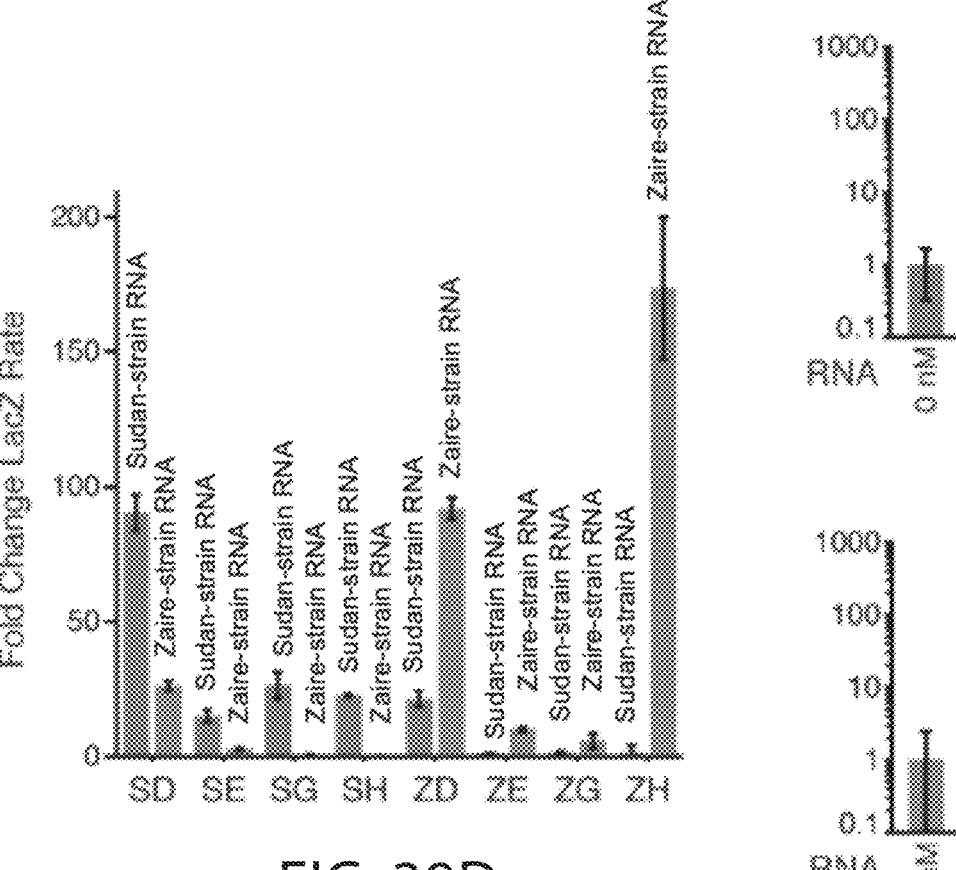
Figure 39E:
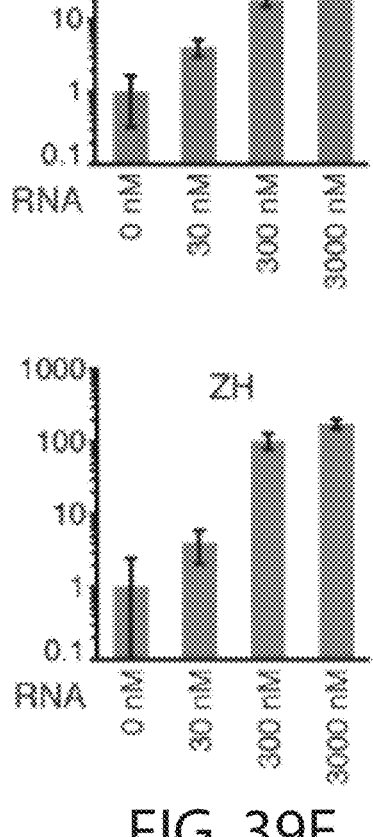

The colorimetric dynamics of the 240 reactions were captured using a plate reader and could be tracked by eye (FIGS. 39B-39C). Each of the 24 sensors was triggered in the presence of their target (3000 nM), with maximum induction during the first 90 minutes ranging between 4 to 77 fold. Remarkably, this phase of the screen was completed in less than 12 hours. Four matching sets (D, E, G, H) of the Sudan and Zaire sensors were then selected to test specificity and found a high degree of strain-specific discrimination (FIG. 39D), as well as sensitivity down to a concentration of 30 nM trigger RNA for both strains (FIG. 39E).

Figure 40A:
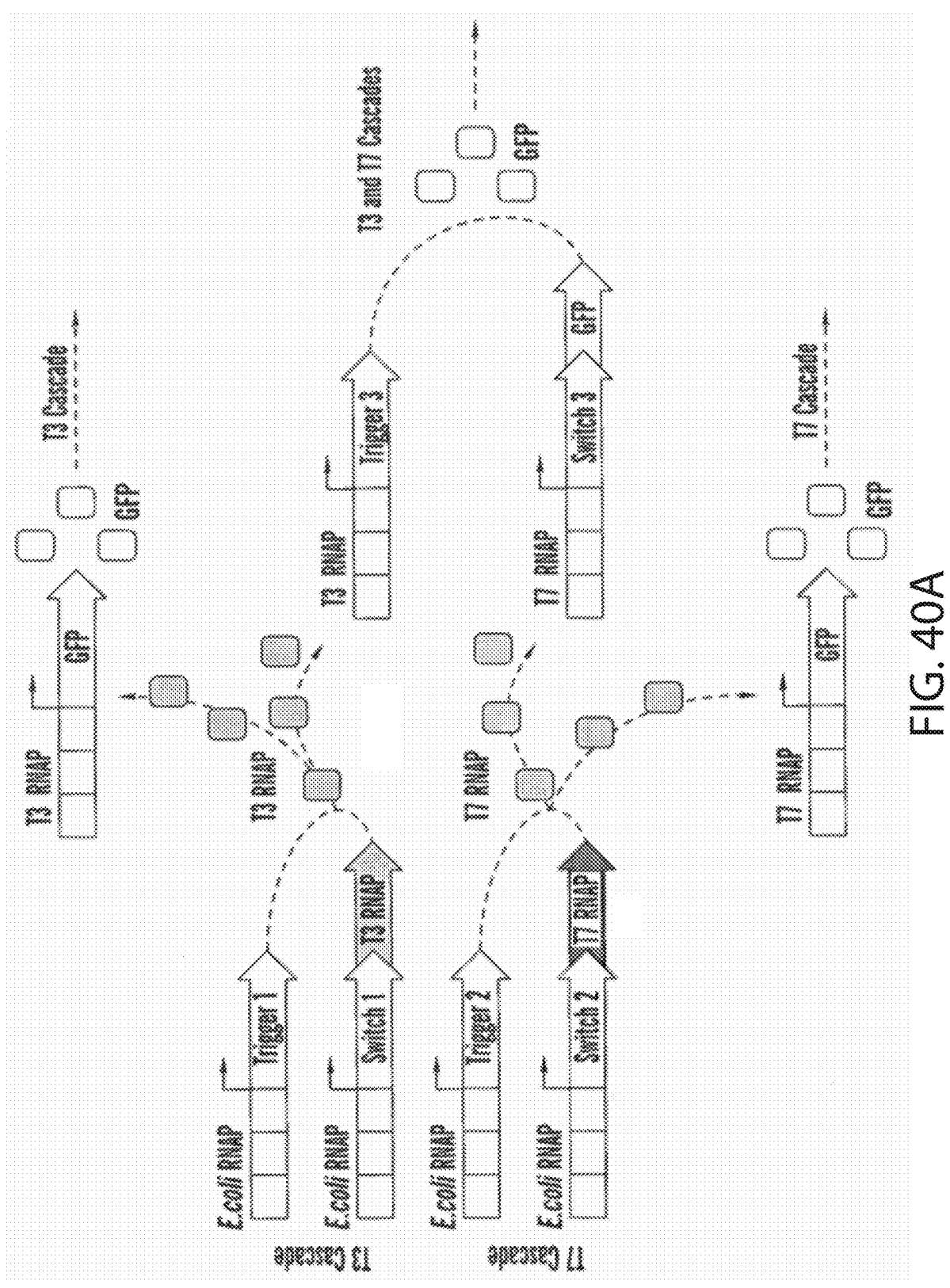
FIGS. 40A-40D demonstrate paper-based converging transcriptional cascade.
Figures 40B, 40C, 40D:
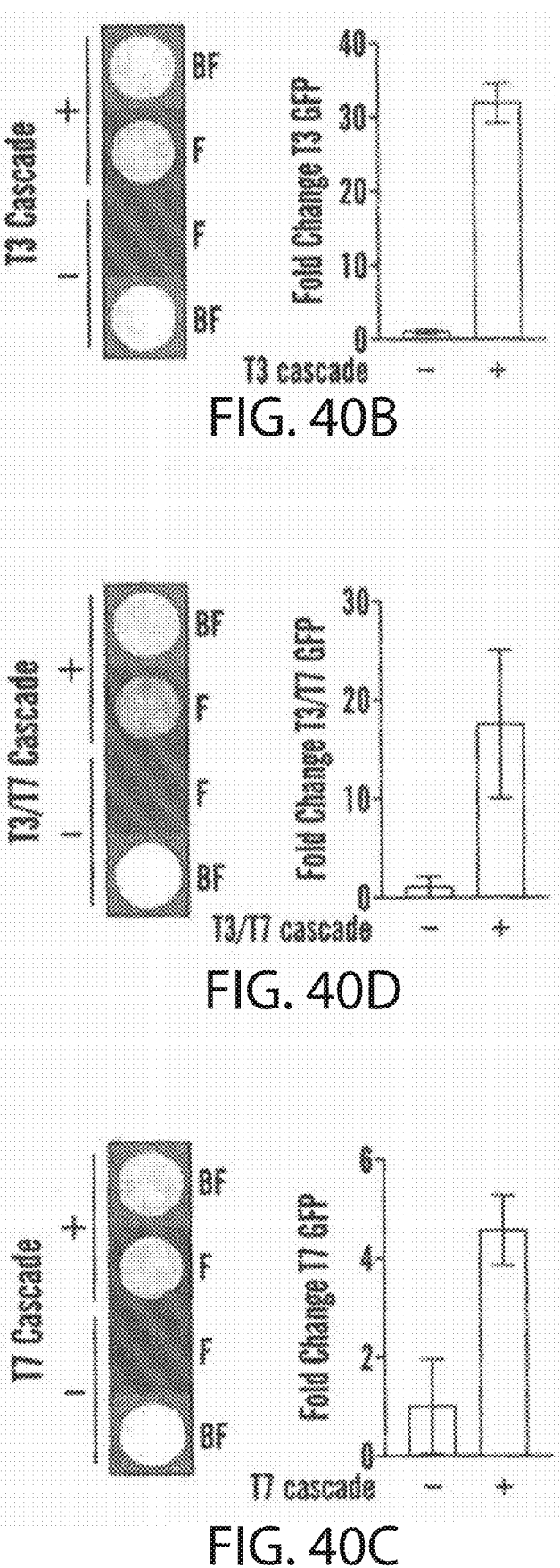

As a demonstration of the capacity of the paper-based system for the prototyping and testing of more complex synthetic gene circuits, a converging transcription cascade was assembled that can convert the transcription activity of the native E. coli RNAP in a cell extract, into T3 and/or T7 RNAPs (FIG. 40A). To this point the paper-based system has been validated using over 45 toehold switches, each with a unique combination of inputs and measureable outputs. Here toehold switches were assembled to create a series of molecular reactions that leads to the production of novel transcriptional tools. In the presence of DNA encoding the toehold switch and trigger for the T3 module, T3 RNAP is transcribed and translated, which activates T3-mediated transcription and translation of GFP from an otherwise passive component (FIG. 40B). Alternatively, in the presence of DNA encoding the toehold switch and trigger for the T7 module, T7 RNAP is transcribed, translated and similarly leads to the expression of GFP from a T7-mediated construct (FIG. 40C). If both the T3 and T7 toehold switch modules are combined, E. coli RNAP generates both T3 and T7 RNAPs. This converging transcription activity leads to their respective trigger and toehold switch RNAs, producing a third route to GFP expression (FIG. 40D). This work shows that the platform can sustain multiple rounds of transcription and translation, and be utilized to construct, test and debug complex circuits in a modular fashion.

Methods

TetR-based inducible synthetic gene circuits. The TetR-based GFP and mCherry expression circuits were constructed by inserting GFP or mCherry downstream of the TetR-repressed pLtetO promoter in pZE11 (Lutz and Bujard 1997). To provide constitutive tetR expression, tetR was cloned downstream of the constitutive PlacIQ promoter, and this expression cassette was inserted into pZE11-gfp and pZE11-mcherry using XhoI and AatII.

Figures 37A, 37B, 37C, 37D:
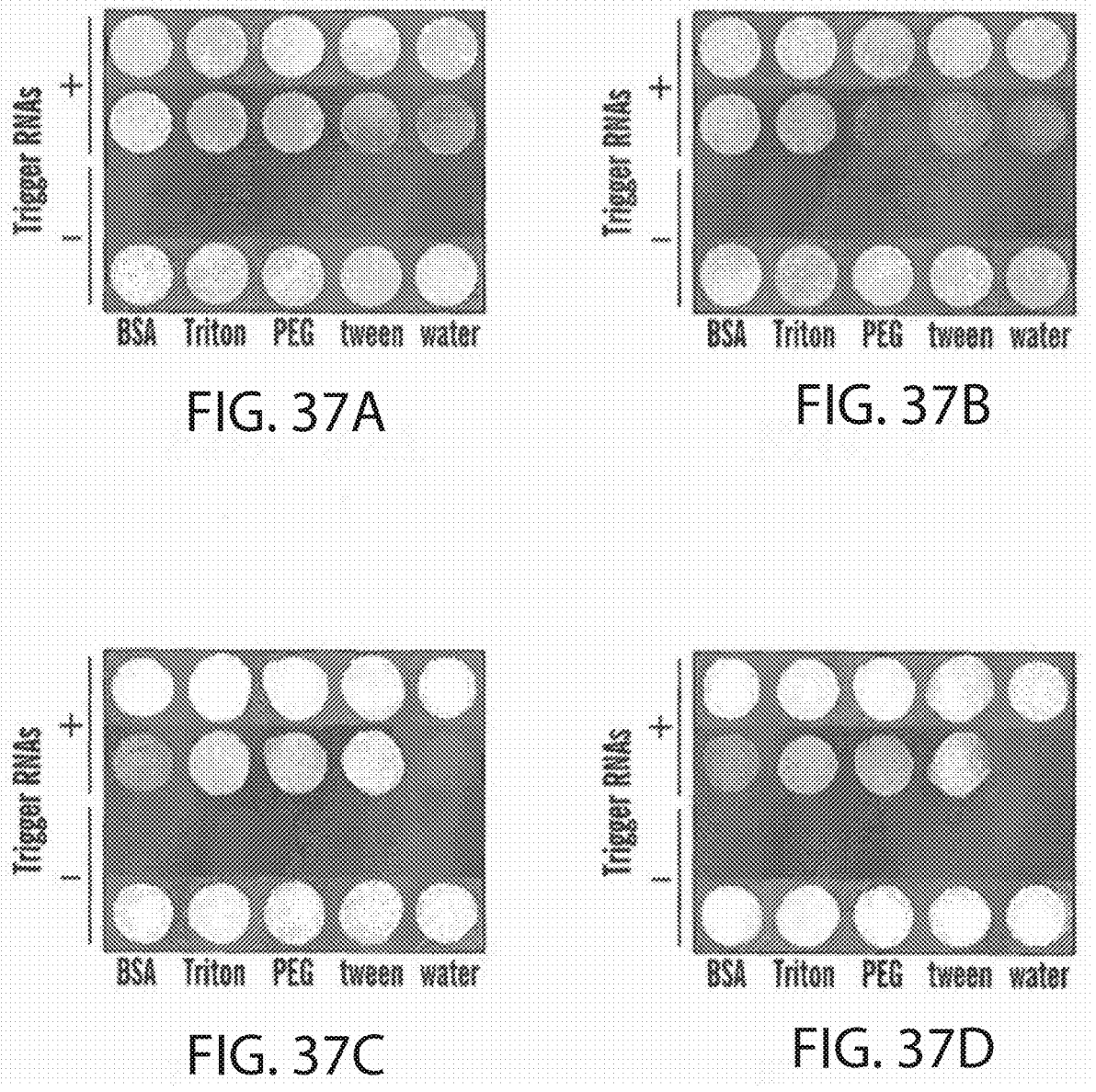
FIGS. 37A-37D is a set of images showing that blocking paper and quartz microfiber improves the efficiency of GFP expression.

Preparation of matrix materials. While the paper-based reactions were successful, non-specific interactions between the components of the cell-free system and the cellulose matrix of paper could be impeding the activity of the reactions. Cellulose holds a pH-dependent charge (Budd, J. and Herrington, T. M., Colloids and Surfaces. Volume 36, Issue 3, 1989, Pages 273-288) and thus it seemed likely that components from the complex biomolecular systems would adsorb to the high surface area of cellulose fibers, reducing reaction efficiency. Methods to improve performance by inhibiting these non-specific interactions with paper were tested. In one approach, the filter paper was treated with bovine serum albumin (BSA) and/or other blocking reagents. An overall improvement in fluorescent output from treated paper was found, with 5% BSA yielding the greatest increase (FIGS. 37A-37B). For quartz microfiber, an alternate substrate, the performance enhancement of blocking with the surfactant Tween-20 was even more pronounced (FIGS. 37C-37D).

Cell-free reactions. Cell-free reactions were generally assembled (4° C.) as described in the instructions of the respective manufacturers. Briefly, for S30 and S30T7 reactions (Promega, L1020 and L1110), cell extracts and premix containing amino acids were combined at a ratio of 0.33 and 0.51, respectively. The volume was then brought up with RNase inhibitor (Roche; 0.005), plasmid DNA constructs comprising the gene circuits and nuclease-free ddH$_2$O. For TetO-based gene circuits, reactions were supplemented with pre-run cell-free reactions expressing constitutive tetR (0.05) to reduce promoter leakage. For the PT7 cell-free system (NEB, E6800L), solution A (0.4) and B (0.3) were combined together, with the remaining volume comprised of RNase inhibitor (Roche; 0.005), linear DNA constructs and nuclease-free ddH2O. Hela cell cell-free systems (Thermo Scientific, 88881) were assembled by combining Hela cell lysate (0.5), accessory proteins (0.1) and reaction mix (0.2) with RNase inhibitor (Roche; 0.005), plasmid DNA constructs comprising the gene circuits and nuclease-free ddH2O. Long-term storage of freeze-dried pellets was done under nitrogen gas and silica gel desiccation packages.

Figure 16G:
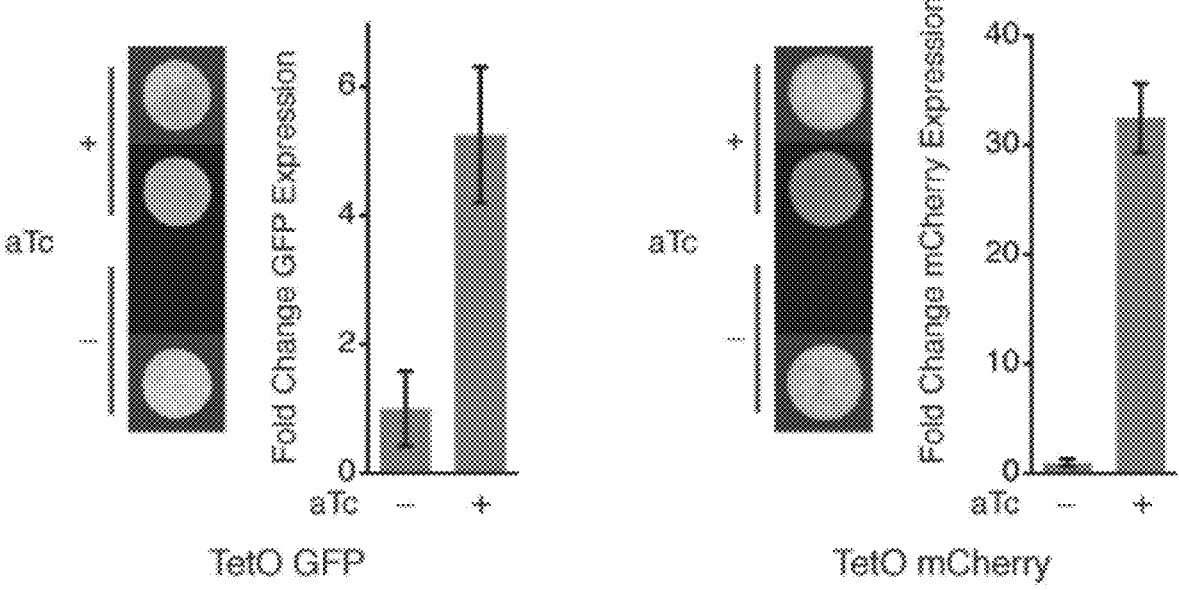
FIG. 16G is a set of images and fold change measurement of GFP and mCherry from the TetO promoter, +/−aTc inducer, from freeze-dried S30 reactions. aTc concentration used 11 uM.

The concentration for the gene circuits were as follows: FIGS. 16B & 16C: T7_GFP plasmid DNA 5 ng/μl (pBR939b_T7_GFP, Anderson, 2007); FIG. 16E: PN25-GFP plasmid DNA 30 ng/μl and T7_GFP plasmid DNA 30 ng/μl; FIG. 16G: Tet-O GFP and TetO-mCherry plasmid DNA 30 ng/μl; FIG. 17: linear DNA 33 nM, RNA triggers at 5 tM;

FIG. 18: linear DNA 33 nM, RNA triggers at 5 μM or as specified; FIGS. 19B & 19C: mCherry and GFP mRNA sensors linear DNA 33 nM, respective mRNAs at 2.5 tM; FIGS. 16D & 16E: antibiotic resistance gene mRNA sensors for spectinomycin, chloramphenicol, kanamycin and ampicillin linear DNA 33 nM, respective mRNAs at 3 μM or as specified;

FIG. 19F: pT7CFE1_GFP plasmid DNA (Thermo Scientific) 30 ng/μl, pcDNA3.1 FLIPglu-30uDeltal3V plasmid DNA (Takanaga 2010, addgene:18015) 30 ng/μl; FIG. 39: PCR product was not gel-purified and therefore used a 5×linear DNA concentration of 150 ng/μl to ensure adequate sensor product, respective trigger RNAs at 3 μM or as specified; FIG. 40: T3 and T7 cascade modules plasmid DNA 30 ng/μl (*E. coli* RNAP_trigger 1, Ecoli RNAP_switch_1_T3RNAP, *E. coli* RNAP_trigger 2, *E. coli* RNAP_switch_2_T7RNAP), T3_GFP and T7_GFP plasmid DNA 40 ng/μl, T3 RNAP_trigger_3 and T7 RNAP_switch 3_GFP plasmid DNA 40 ng/μl.

Figures 1, 38A:
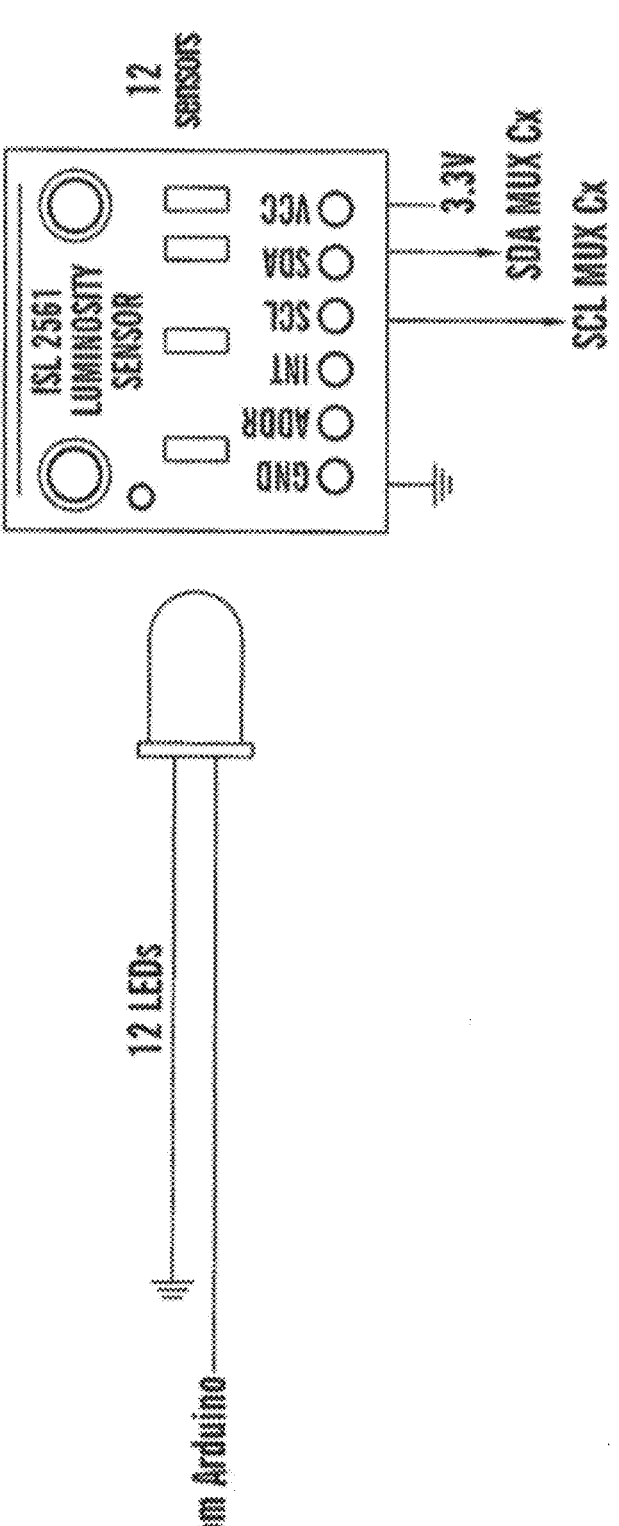
FIGS. 38A-38B show components used in the fabrication of an optical electronic reader.
Figures 2, 38A:
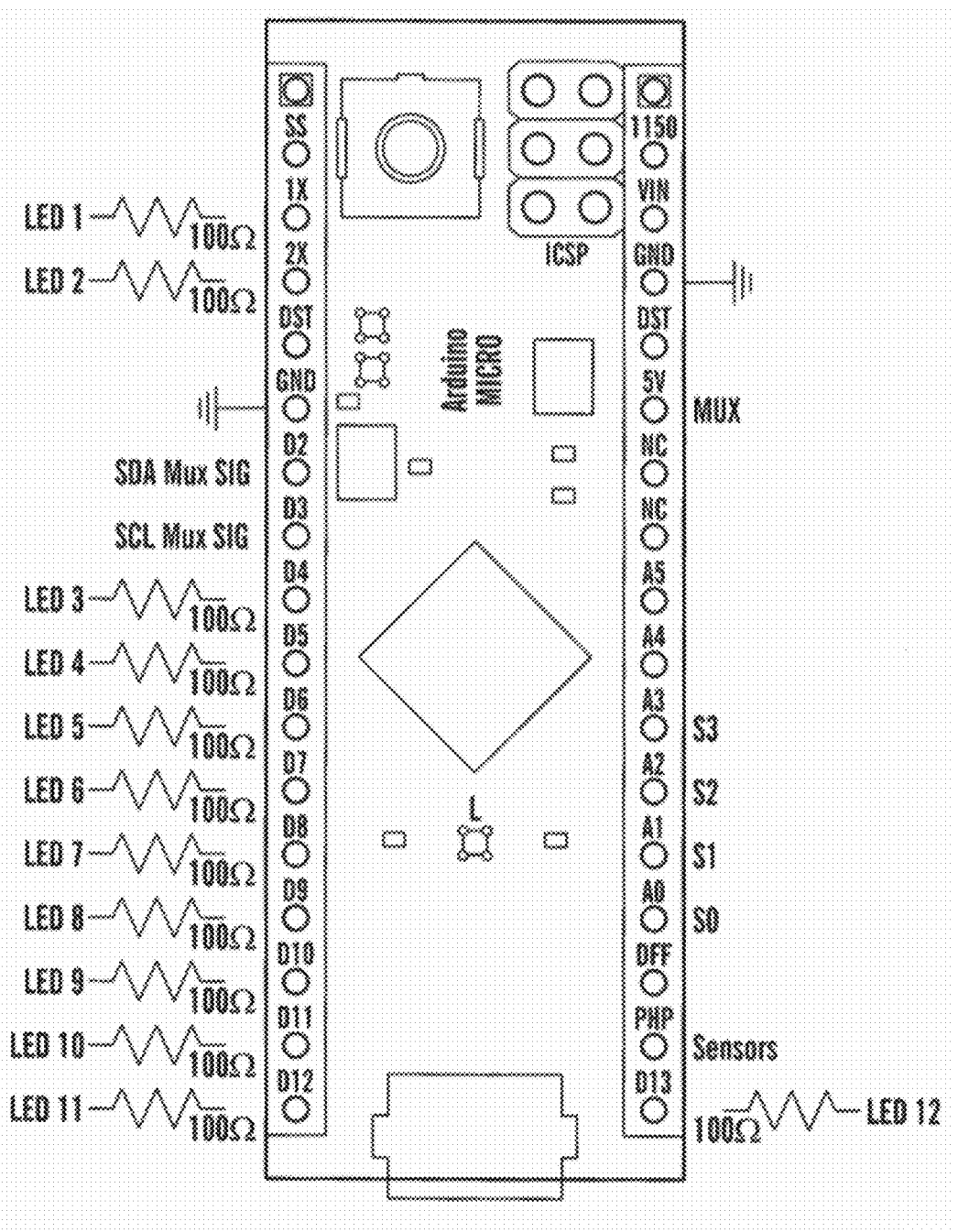
Figures 3, 38A:
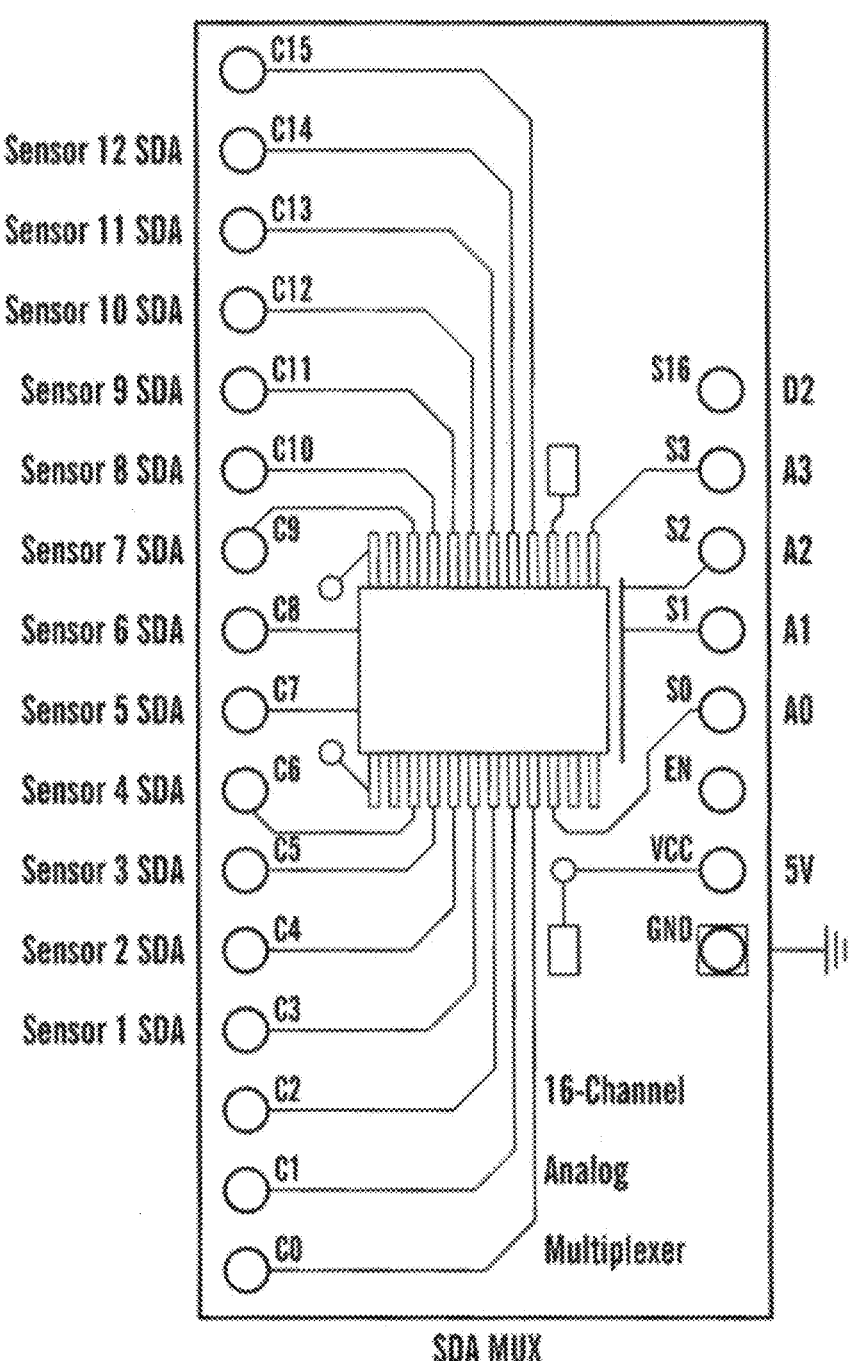
Figures 4, 38A:
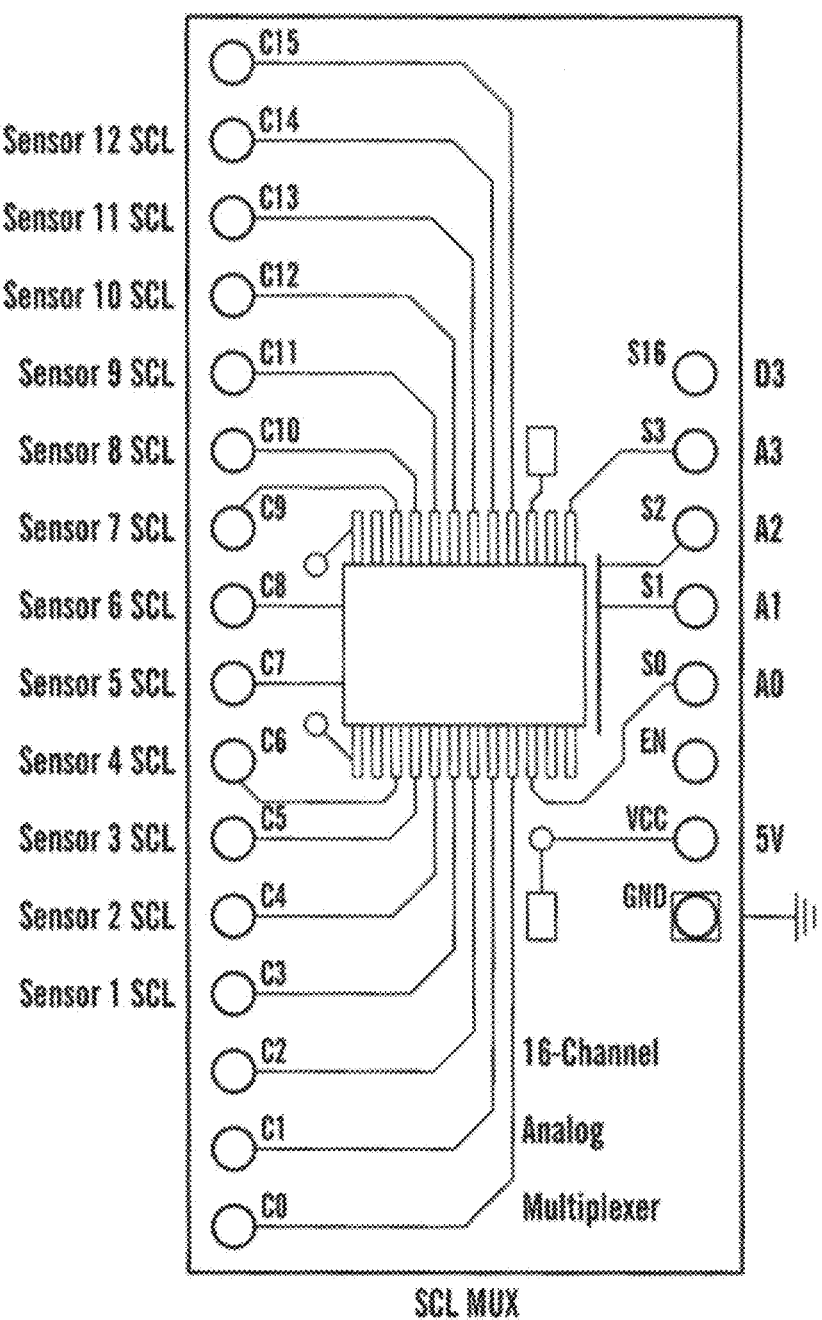
Figure 38B:
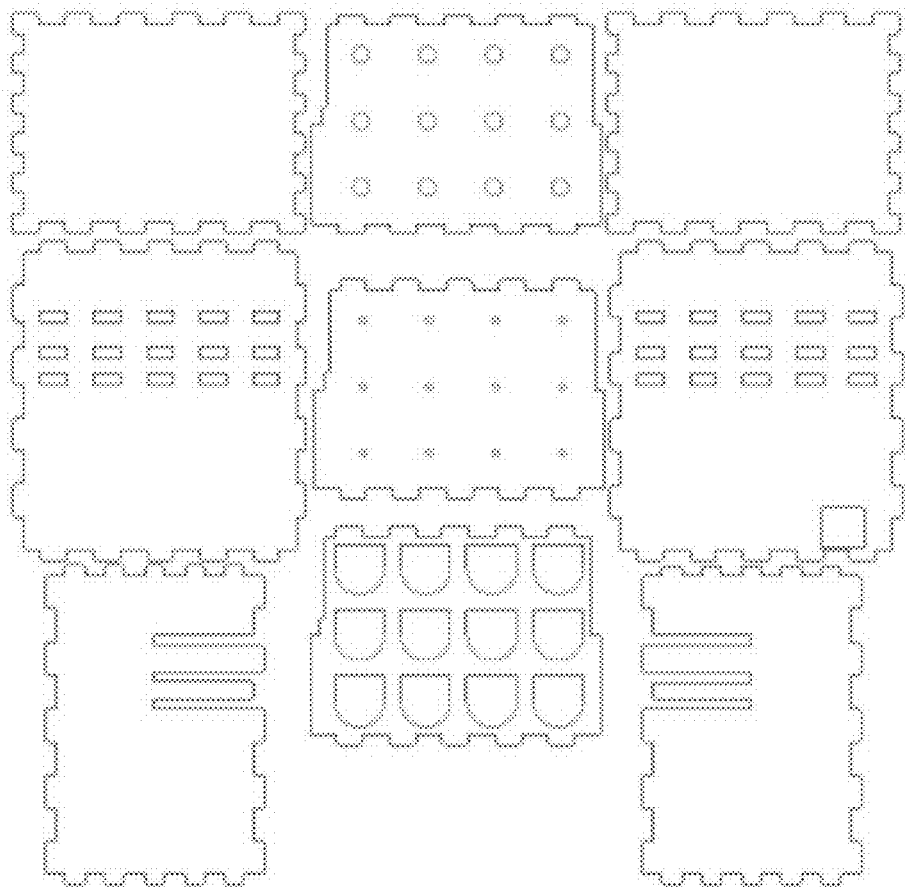

Preparation of reactions and incubation. Assembled cell-free reactions were applied (1.8 μl/disc) to 2 mm paper discs (Whatman, 1442-042), which were then flash frozen in liquid nitrogen and freeze-dried overnight. Paper discs were cut using a 2 mm biopsy punch. Similarly quartz microfiber (Spectrum, 884-66171) was cut and treated with cell-free reactions (3 μl/disc) prior to freeze-drying. Freeze-dried solution phase reactions (7 ul) were similarly flash frozen and place on the lyophilizer. After 24 hours, reactions were rehydrated with either nuclease-free ddH2O or inducer (activated switches) at the concentrations specified. Cell-free reactions without synthetic gene networks were also included to provide the background signal for subtraction from control and treatment reactions. Rehydrated reactions were incubated at 37° C. using either a plate reader (BioTek NEO HTS) or the purpose-built electronic optical reader placed inside a tissue culture incubator. For the plate reader, paper discs were placed into black, clear bottom 384 well plates and for the purpose-built reader, paper discs were placed into 2 mm holes cut into the removal acrylic chip (FIGS. 18H, 38B).

Microscopy and image processing. Images of paper discs were collected on a Zeiss Axio Zoom V16 Macroscope (magnification 7×) with an AxioCam MRm in a humidified glass chamber or through the bottom of a clear bottom 384-well plate. Collected images were then stitched together using Zeiss Zen software into large composite images for further processing in ImageJ. Experiments were arranged so that images of control and treatment paper-based reactions were collected together such that parameters could be adjusted for all samples simultaneously. Once optimized, images of individual paper discs were cropped and arrayed into figures. For GFP expression in S30 cell-free system, which exhibits a high level of autofluorescence, a Nuance camera was used to collect multispectral images at between 500 and 620 nM. Perkin Elmer Nuance 3.0.2 software was then used to unmix the spectral signature of the GFP from that of the cell extract. A similar approach was used to create a 410 nm absorbance signature (420 to 720 nM) for image paper discs with p-nitrophenol, the chitinase cleavage product of 4-Nitrophenyl N,N'-diacetyl-beta-D-chitobioside. Images collected with the Nuance camera were scaled using bilinear transformation. For a few composite images, areas around the paper discs were masked to remove extraneous light.

Printed arrays. Patterns for printed arrays were generated using Adobe Illustrator and then printed onto chromatography paper (Whatman, 3001-861) using a Xerox 8570 printer (Carrilho et al., Anal Chem.2009, 81(16):7091-5). Once printed, the wax was reflowed using a hot plate (120° C.) so that the wax was present through entire thickness of the paper, creating hydrophobic barriers to contain each reaction.

Electronic optical reader. The portable device consists of four layers housed within a laser-cut acrylic box (FIG. 18H). The top layer holds 12 LEDs (Digi-Key, 365-1190-ND), which have a very narrow viewing angle and an emission of 570 nM to match the absorbance maximum of the product of the LacZ reaction. The LEDs were placed in close proximity to the chip in the middle layer, which holds 12 paper discs within 2 mm apertures. The apertures prevented transmission of stray light and were coaxial with the LEDs in the top layer, and the array of 12 TSL2561 sensors (Adafruit, 439) in the third layer below. The bottom layer contains the Arduino Micro and associated electronics such as the multiplexers (Sparkfun, BOB-09056), breadboard, resistors and connectors. To prevent cross talk between reads, reactions were read in series by sequentially activating each LED and sensor pair. The read frequency and pattern of the reader can be easily adjusted by modifying and uploading alternative sketches to the Arduino Micro. Both the raw data and the data processed using the per disc formula: 100-(100*(Current/Max)), were calculated for each time point and sent to a laptop. A diagram of the circuit and an overview of the laser cut parts can be found in the supplemental figures (FIGS. 38A-38B).

Calculation of fold change. Fluorescence or absorbance data from the plate reader were first smoothed to reduce measurement noise using a moving three-point average of the time point and the data both preceding and following that read. Background signal was subtracted from each well using the average of control blank reactions that contained the relevant cell-free system alone. The minimum value of each well was then adjusted to zero. For fluorescence data, fold change calculations were done by dividing the wells at each time point by the average signal from the corresponding uninduced control wells. For absorbance measurements, fold change values reflect the difference in the rate of color change between induced and uninduced wells. This was done by calculating the rate of change using slope; therefore for each 10 minute time point, the rate reported was calculated as follows: slope=(T2-T1)/10, where T is the normalized data at a time point (T1) and the time point 10 minutes later (T2). Fold change was then calculated as with the fluorescence data. Experiments were run in either triplicate or quadruplicate. Due to high autofluorescence of the S30 reactions, a few experiments exhibited high variability and were accordingly subjected to the Modified Thompson Tau Test to identify outliers to be discarded (Anbarasi et al., Outlier Detection for Multidimensional Medical Data International Journal of Computer Science and Information Technologies 2011, Vol. 2 (1), 512-516; Byrd et al., Remote Sensing of Environment 2014, 149: 166-180). Briefly, the Tau test was performed by calculating the difference (Delta) between a measured value (replicate) and the mean of the group. Using the Modified Thompson Tau value for quadruplicate data (1.4250), the test was performed by multiplying the standard deviation of the group by this Tau value. If the resulting number was smaller than the Delta calculated for a measured value, that replicate was considered an outlier and not included in the analysis.

DISCUSSION

A method has been developed for embedding synthetic gene networks into paper and other materials, creating a much-needed path for moving synthetic biology out of the lab and into the field. Here a number of purpose-built synthetic gene networks responsive to synthetic RNA, mRNA and small molecules have been constructed for this approach. This includes paper-based toehold switches that routinely generate networks with greater than 20-fold and as high as 350-fold induction (FIGS. 17B, 18C, 29A). As demonstrated with the glucose sensor, this paper-based approach also promises to easily convert existing constructs designed for basic research and biotechnology into portable and readily accessible molecular tools (FIG. 19G-19H).

The in vitro nature of these reactions affords other benefits. For instance, without having to contend with maintaining the plasmid over generations of cell division, complex genetically encoded networks can be assembled without the need for coordinating selective antibiotic pressures. Moreover, paper-based reactions can also serve as a mock cell, allowing for linear PCR products to be screened directly for function without sequencing, assembly into circularized plasmids or possibly even purification of fragments. These features were taken advantage of in the paper disc arrays described herein looking at toehold orthogonality as well as Ebola sensor prototyping and complex circuit testing (FIGS. 17D-17E, 32, 39, 40), which allowed us to rapidly screen for gene circuit performance.

The paper-based cell extracts also offer a unique opportunity for molecular biologists to work with difficult-to-culture organisms. By generating cell extracts from engineered cell lines, pathogens or other specialized organisms (i.e., extremophiles, symbionts), these reactions could serve as a proxy for biology that is otherwise inaccessible to the broad research community. Similarly, the incorporation of human cell extracts into the paper-based scheme is an exciting feature that leads to the prospect of diagnostic and synthetic biology applications based on the thousands of human and mammalian transcription factors (Hughes, 2011), such as nuclear receptors, with complex and nuanced regulatory features, including small molecule-responsive regulation (Pardee et al., 2009).

Using the technology described herein, the rational design of synthetic biology can be brought to in vitro diagnostics and sensing. Examples of existing technologies that could be implemented as part of the platform include isothermal nucleic acid sequence-based amplification of target RNA inputs (Yan et al., Mol Biosyst., 2014, 10:970-1003) or concentration of pathogen through generic opsonin-mediated capture (Cooper et al, Lab Chip., 2014, 14:182-8; Kang et al., Nature Medicine 2014). Moreover, rather than competing with technically demanding and expensive lab-based techniques like ELISA, PCR and mass spectrometry, paper-based systems permits the creation of a new, low-cost generation of sensors that could be embedded ubiquitously into daily life (including clothing). Importantly, toehold switch reactions can be run in a variety of porous materials, including cloth, lab membranes and porous alumina.

Unlike antibody-based diagnostics, toehold switch mRNA sensors offer a sequence-based method of detection that means research and clinical tools can be designed rationally, lowering development costs and allowing for significantly shorter design-to-production cycles. Here novel mRNA sensors were presented, including 24 Ebola sensors constructed in less than 12 hours. The DNA input cost for the Ebola series was $21 USD/sensor. These features compare highly favorably to custom commercial antibody production, where development time is typically two to six months and development costs range from $4,000 to $30,000 USD. Further, sensors can be designed from sequence information alone, which is ideal for emerging pathogens (FIG. 39), and the acquisition of other relevant clinical information, such as the presence of drug-resistance genes (FIGS. 19D-19E) or other indicators of pathogenesis, such as biofilm-specific RNAs (Dotsch et al., PLoS One., 2012, 7(2):e31092). Coupled to an electronic reader, these paper-based systems also offer the potential for quantitative diagnostics (FIGS. 18I, 19E), a much-needed feature that is for the most part not available with RDTs (Cordary, Am. J. Trop. Med. Hyg., 2012, 87, 223-230). Moreover, the added sensitivity (2.5-3.5×) of the purpose-built, electronic reader could be considered a hardware enhancement of the designed gene circuits (FIGS. 19E, 34D).

Paper-based synthetic gene networks are also potentially less expensive to manufacture than most of the standard of care options currently available. At the moment, the cost of a 1 μl paper-based sensor would be between 35 ¢-65 ¢ using commercial cell-free expression systems. However, these systems can be readily produced in house, reducing the cost to as little as 2 ¢-4 ¢ per sensor (which can be found on the world wide web at openwetware.org/wiki/Biomolecular_Breadboards.Protocols:cost_estimate). This compares to $0.45-$1.40 for a single RDT reaction and $1.50-$4.00 (reagents only) for PCR (Cordary, Am. J. Trop. Med. Hyg., 2012, 87, 223-230). Transcription- and translation-based detection is also competitive with regards to time to detection. As an example, detection of mRNA from the ampicillin resistance gene was recorded as early as 20 minutes for high concentrations of mRNA and about 40 minutes for the 3 nM treatment (FIGS. 19E, 35). This compares favorably to RDTs, which can detect a single antigen in ~20 minutes, or PCR, which can take 1.5 to 2 hours and is largely confined to laboratory settings (Cordary, Am. J. Trop. Med. Hyg., 2012, 87, 223-230).

The construction and testing of a converging transcription cascade on freeze-dried paper discs (FIG. 40) further underscores the potential of this approach to host complex network reactions for both laboratory and field applications. While perhaps not at first obvious, for each of the three transcription cascade reactions to produce GFP (FIGS. 39B-39D), the system had to essentially cycle through two cycles of the central dogma. The first cycle converts the DNA of the cascade module(s) to RNA and then protein (RNAP), which sets off the second cycle that converts the DNA of dormant reporter to RNA and then protein (GFP). Thus, despite their small size, the paper discs have the transcription and translation capacity required for complex tasks. For synthetic biology applications, such a transcription cascade could be used to build more sophisticated networks with layers of outputs lying inactive unless triggered by a circuit producing the correct RNAP. Further, as the orthogonality (FIGS. 17D, 32) and Ebola screens showed (FIG. 39), the paper-based system has significant potential for increasing the pace at which genetically encoded tools can be built and tested. With this in mind, this technology can be extended to prototyping of engineered metabolic pathways and other complex gene circuits as a way to rapidly vet combinatorial designs before moving to cellular hosts. Thus, ready-to-use paper-based systems could not only make tools currently only available in laboratory readily fieldable, but also improve the development of new tools and the accessibility of these molecular tools to educational programs for the next generation of practitioners.

Paper-based synthetic gene networks can significantly expand the role of synthetic biology in the clinic, global health, industry, research and education.

What is claimed is:

1. A method of detecting the presence or absence of a trigger RNA in a sample, comprising:
   (i) providing a shelf-stable composition comprising a cell-free system comprising components for a coupled transcription/translation reaction, wherein said cell-free system is lyophilized on a porous substrate and is substantially free of water, and wherein said cell-free system is able to perform said coupled transcription/translation reaction upon re-hydration of said cell-free system, wherein said composition comprises a switch RNA sensor encoding a fluorescent reporter protein capable of producing a detectable fluorescent signal, wherein the switch RNA sensor is a toehold switch sensor comprising a hairpin structure, wherein the toehold switch RNA sensor comprises, in order of, from its 5' to its 3', a toehold region, a first stem domain of the hairpin structure, a loop domain of the hairpin structure having a ribosome binding site (RBS), a second stem domain of the hairpin structure having a translation initiation codon, and a gene coding for the flourescent reporter protein;
   (ii) contacting said composition with said sample in the presence of water under conditions for permitting hybridization of the trigger RNA with the toehold switch RNA sensor, the hybridization of the trigger RNA with the toehold switch RNA sensor unwinding the hairpin structure of the toehold switch RNA sensor to a single-strand RNA and permitting that the fluorescent reporter protein is translated from the toehold switch sensor by the coupled transcription/translation reaction to said composition if the trigger RNA is present in the sample, wherein the trigger RNA comprises a sequence complementary to both the toehold region and a sequence of the first stem domain of the hairpin structure which is adjacent to the toehold region; and
   (iii) detecting said fluorescent signal from the flourescent reporter protein in said composition after step (ii), wherein detection of said fluorescent signal from the flourescent reporter protein in said composition after step (ii) indicates the presence of said trigger RNA in the sample.

2. The method of claim 1, further comprising a step of contacting said composition with a barrier to prevent water evaporation or enclosing said composition in an enclosure after step (ii).

3. The method of claim 1, wherein the cell-free system comprises a whole cell extract or recombinant protein transcription/translation system.

4. The method of claim 1, wherein the porous substrate comprises paper, quartz microfiber, cellulose acetate, silk, or aluminum oxide.

5. The method of claim 1, wherein the cell free system is partially or completely embedded in the porous substrate.

6. The method of claim 1, wherein the porous substrate is paper, wherein the fluorescent reporter protein is a Green Fluorescent Protein (GFP), and wherein said fluorescent signal is a GFP signal.

7. The method of claim 1, wherein the trigger RNA is mRNA of an antibiotic resistance gene.

8. The method of claim 7, wherein the antibiotic resistance gene is selected from a kanamycin resistance gene, a spectinomycin resistance gene, a chloramphenicol resistance gene and an ampicillin resistance gene.

9. The method of claim 1, wherein the fluorescent protein is selected from GFP, Venus, mCherry and cerulean.

10. A method of detecting the presence or absence of a trigger RNA in a sample, comprising:
   (i) providing a shelf-stable composition comprising a cell-free system comprising components sufficient for a coupled transcription/translation reaction, wherein said cell-free system is lyophilized on a porous substrate and is substantially free of water, and wherein said cell-free system is able to perform said coupled transcription/translation reaction upon re-hydration of said cell-free system, wherein said composition comprises a switch RNA sensor encoding an enzymatic reporter protein capable of producing a color product when the enzymatic reporter protein interacts with its substrate, wherein the switch RNA sensor is a toehold switch sensor comprising a hairpin structure, wherein the toehold switch RNA sensor comprises, in order of, from its 5' to its 3', a toehold region, a first stem domain of the hairpin structure, a loop domain of the hairpin structure having a ribosome binding site (RBS), a second stem domain of the hairpin structure having a translation initiation codon, and a gene coding for the enzymatic reporter protein;
   (ii) contacting said composition with said sample in the presence of water and a substrate of the enzymatic reporter protein under conditions for permitting hybridization of the trigger RNA with the toehold switch RNA sensor, the hybridization of the trigger RNA with the toehold switch RNA sensor unwinding the hairpin structure of the toehold switch RNA sensor to a single-strand RNA and permitting the enzymatic reaction protein is translated from the toehold switch sensor by the coupled transcription/translation reaction to said composition if the trigger RNA is present in the sample, wherein the trigger RNA comprises a sequence complementary to both the toehold region and a sequence of the first stem domain of the hairpin structure which is adjacent to the toehold region; and
   (iii) detecting said color product producing by interacting the enzymatic reporter protein with its substrate in said composition after step (ii), wherein detection of said color product producing by interacting the enzymatic reporter protein with its substrate in said composition after step (ii) indicates the presence of said trigger RNA in the sample.

11. The method of claim 10, wherein the trigger RNA is mRNA of an antibiotic resistance gene.

12. The method of claim 11, wherein the antibiotic resistance gene is selected from a kanamycin resistance gene, a spectinomycin resistance gene, a chloramphenicol resistance gene and an ampicillin resistance gene.

13. The method of claim 10, wherein the enzyme is selected from chitinase, β-galactosidase, glucose oxidase, and luciferase.

\* \* \* \* \*